US007919223B2

(12) United States Patent
Echigo et al.

(10) Patent No.: US 7,919,223 B2
(45) Date of Patent: Apr. 5, 2011

(54) COMPOUND FOR RESIST AND RADIATION-SENSITIVE COMPOSITION

(75) Inventors: Masatoshi Echigo, Kanagawa (JP); Dai Oguro, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 625 days.

(21) Appl. No.: 11/722,636

(22) PCT Filed: Dec. 26, 2005

(86) PCT No.: PCT/JP2005/023733
§ 371 (c)(1),
(2), (4) Date: Jun. 22, 2007

(87) PCT Pub. No.: WO2006/068267
PCT Pub. Date: Jun. 29, 2006

(65) Prior Publication Data
US 2008/0113294 A1 May 15, 2008

(30) Foreign Application Priority Data

| Dec. 24, 2004 | (JP) | 2004-374003 |
| Mar. 17, 2005 | (JP) | 2005-076319 |
| May 16, 2005 | (JP) | 2005-142162 |
| Jul. 4, 2005 | (JP) | 2005-194941 |

(51) Int. Cl.
*G03F 7/004* (2006.01)
(52) U.S. Cl. ............... 430/270.1; 430/192; 430/905
(58) Field of Classification Search .............. 430/192, 430/270.1, 905
See application file for complete search history.

(56) References Cited

U.S. PATENT DOCUMENTS

| 5,340,688 | A | 8/1994 | Kawabe et al. | |
| 6,773,862 | B2 * | 8/2004 | Shirakawa et al. | 430/270.1 |
| 6,824,948 | B1 * | 11/2004 | Aoai et al. | 430/281.1 |
| 7,504,196 | B2 * | 3/2009 | Shiono et al. | 430/270.1 |
| 2003/0203305 | A1 | 10/2003 | Yasunami et al. | 430/270.1 |
| 2003/0211421 | A1 | 11/2003 | Hanabata et al. | |
| 2007/0059632 | A1 * | 3/2007 | Oguro et al. | 430/281.1 |
| 2008/0153031 | A1 * | 6/2008 | Echigo et al. | 430/281.1 |

FOREIGN PATENT DOCUMENTS

| EP | 0 747 768 | 12/1996 |
| JP | 02-252724 | 10/1990 |
| JP | 04-301851 | 10/1992 |
| JP | 05-022410 | 1/1993 |
| JP | 06-118649 | 4/1994 |
| JP | 07-134413 | 5/1995 |
| JP | 08-310985 | 11/1996 |
| JP | 09-211862 | 8/1997 |
| JP | 09-236919 | 9/1997 |
| JP | 10-282649 | 10/1998 |
| JP | 11-072916 | 3/1999 |
| JP | 11-143074 | 5/1999 |
| JP | 11-167199 | 6/1999 |
| JP | 11-258796 | 9/1999 |
| JP | 11-322656 | 11/1999 |
| JP | 2000-305270 | 11/2000 |
| JP | 20010312055 | * 9/2001 |
| JP | 2001-312055 | 11/2001 |
| JP | 2002-049152 | 2/2002 |
| JP | 2002-099088 | 4/2002 |
| JP | 2002-099089 | 4/2002 |
| JP | 2002-328466 | 11/2002 |
| JP | 2002-363123 | 12/2002 |
| JP | 2003-183227 | 7/2003 |
| JP | 2004-137262 | 5/2004 |
| JP | 2004-191913 | 7/2004 |
| JP | 2004-341482 | 12/2004 |
| JP | 2005-091909 | 4/2005 |
| JP | 2005-266741 | 9/2005 |
| JP | 2005-309421 | 11/2005 |
| JP | 2005-328638 | 11/2005 |
| WO | WO 2005/029189 A1 | 3/2005 |
| WO | WO 2005/081062 A1 | 9/2005 |
| WO | WO 2005/101127 A1 | 10/2005 |

OTHER PUBLICATIONS

Extended European Search Report dated Aug. 20, 2010, including Supplementary European Search Report and European Search Opinion, for Application No. 05842247.8-1226.

* cited by examiner

*Primary Examiner* — John S Chu
(74) *Attorney, Agent, or Firm* — Antonelli, Terry, Stout & Kraus, LLP.

(57) ABSTRACT

A radiation-sensitive composition containing 1 to 80% by weight of a solid component and 20 to 99% by weight of a solvent. The solid component contains a compound B which has (a) a structure derived from a polyphenol compound A by introducing an acid-dissociating group to at least one phenolic hydroxyl group of the polyphenol compound A which is synthesized by a condensation between a di- to tetrafunctional aromatic ketone or aromatic aldehyde each having 5 to 36 carbon atoms with a compound having 1 to 3 phenolic hydroxyl groups and 6 to 15 carbon atoms, and (b) a molecular weight of 400 to 2000. The composition containing the compound B is useful as an acid-amplified, non-polymeric resist material, because it is highly sensitive to radiation such as KrF excimer lasers, extreme ultraviolet rays, electron beams, and X-rays, and provides resist patterns with a high resolution, high heat resistance, and high etching resistance.

37 Claims, No Drawings

COMPOUND FOR RESIST AND RADIATION-SENSITIVE COMPOSITION

The present invention relates to a radiation-sensitive composition containing a specific compound, which is useful as an acid-amplified, non-polymeric resist material. The compound of the present invention is used as a radiation-sensitive material that is sensitive to radiations such as ultraviolet rays, KrF excimer lasers, extreme ultraviolet rays, electron beams and X-rays for forming masks, etc. in the production of electronics parts such as LSI and VLSI.

BACKGROUND ART

Conventionally known resist materials are generally polymeric materials capable of forming amorphous thin film. For example, a solution of polyhydroxystyrene derivative is applied on a substrate to form a thin resist film, which is then irradiated with ultraviolet rays, far ultraviolet rays, electron beams, X-rays, etc., to form line patterns having a line width of about 0.08 μm.

The known polymeric resist compounds generally have a molecular weight as large as about 10,000 to 100,000 and a broad molecular weight distribution, and their polymer chains are entangled with each other. Therefore, in a lithographic fine process using such polymeric resist compounds, the surface of the fine patterns is roughened, thereby making it difficult to control the dimension of patterns, reducing the product yield, and impairing the transistor characteristics. Therefore, it has been difficult to form patterns having a line width of 0.06 μm or less in the conventional lithographic techniques using the known polymeric resist materials. To produce finer patterns, there have been proposed various low-molecular resist materials with narrow molecular weight distributions.

Known non-polymeric resist materials include, for example, (1) positive- or negative-type resists derived from fullerenes (Patent Documents 1 to 5), (2) positive- or negative-type resists derived from calixarenes (Patent Documents 6 to 8), (3) positive-type resists derived from starburst-type compounds (Patent Documents 9 to 11), (4) positive-type resists derived from dendrimers (Non-Patent Document 1), (5) positive-type resists derived from dendrimer/calixarene (Patent Documents 12 to 13), (6) positive-type resists derived from highly branched starburst-type compounds, (7) positive-type resists derived from ester linkage-containing starburst-type compounds mainly constituted by a trimesic acid structure (Patent Document 14), (8) positive-type resists derived from calix resorcinarenes (Patent Document 15), (9) positive-type resists derived from nitrogen-containing branched polyphenols (Patent Document 16), and (10) positive-type resists derived from compounds having a spiroindane structure or spirobichroman structure (Patent Document 17).

The resist materials (1) are good in the etching resistance but not practical in the coating properties and sensitivity. The resist materials (2) are excellent in the etching resistance, but fail to form satisfactory patterns because of a poor solubility in a developing solution. The resist materials (3) have a low heat resistance, and therefore, may cause the distortion of patterned images during the heat treatment after exposure to light. The resist materials (4) are less practicable because a complicated production process is required and the distortion of patterned images due to their low heat resistance occurs during the heat treatment after exposure to light. The resist materials (5) are less practicable because a complicated production process is required and the raw materials are expensive. The resist materials (6) are less practicable because a complicated production process is required, the raw materials are expensive, and the use of metal catalysts, which are detrimental to the production of semiconductors, is needed. The resist materials (7) are less practicable because the distortion of patterned images due to their low heat resistance is likely to occur during the heat treatment after exposure to light and the adhesion to substrates is poor. The resist materials (8) are less practicable because they are less amorphous and the use of metal catalysts, which are detrimental to the production of semiconductors, is needed to require complicated operations for the purification. The resist materials (9) are less practicable because of their poor resolution. The resist materials (10) are less practicable because the distortion of patterned images due to their low heat resistance is likely to occur during the heat treatment after exposure to light and the adhesion to substrates is poor.

Also disclosed is the addition of a low-molecular compound to a photosensitive resin composition. There have been discloses a photosensitive resin composition which contains a photosensitive compound having a hydrophobic group selected from hydrocarbon groups and heterocyclic groups, a linking group, and a hydrophilic group protected by a protecting group which can be cleaved by the exposure to light (Patent Document 18), a resist composition containing a low-molecular dissolution inhibitor having a non-conjugated structure of two or more triphenylmethane radicals in addition to a group decomposable by an acid (Patent Document 19), and a resist resion composition containing a photosensitive compound having a fluorene structure (Patent Document 20). However, a composition containing the compound of the present invention, which will be described below, as a main component is not hitherto disclosed. Since any of the proposed resist compositions contain a resin, the patterns obtained have a large line edge roughness to make the compositions insufficient for use.

The use of known resist compounds as the main component involves any of the problems of having a low resolution due to a small solution contrast, having a poor film-forming property due to a high crystallizability, failing to exhibit a heat resistance withstanding the semiconductor process, being hardly soluble to safety solvents such as propylene glycol monomethyl ether acetate, propylene glycol monomethyl ether, ethyl lactate, butyl acetate, methyl 3-methoxypropionate and ethyl propionate which are acceptable to the production of semiconductor, and having a poor adhesion to substrate. Therefore, the sole use of known resist compounds has been difficult. For example, a resist composition containing a compound having a non-conjugated structure of two or more triphenylmethane radicals in addition to a group decomposable by an acid (Patent Document 21) and a resist composition containing various types of polyphenols as the main component (Patent Document 22) are unsatisfactory because of their low resolution.

The inventors have proposed, as a non-polymeric resist material for solving the above problems, a resist compound and resist composition mainly composed of a polyphenol compound which is produced by the condensation of phenol with an aromatic ketone or aromatic aldehyde (Patent Document 23). Using the resist compound and resist composition, fine patterns of a line width of 0.06 μm or less can be formed. However, it has been found that the solution contrast, heat resistance, etc. should be improved for producing still finer patterns.

[Patent Document 1] JP 7-134413A
[Patent Document 2] JP 9-211862A
[Patent Document 3] JP 10-282649A

[Patent Document 4] JP 11-143074A
[Patent Document 5] JP 11-258796A
[Patent Document 6] JP 11-72916A
[Patent Document 7] JP 11-322656A
[Patent Document 8] JP 9-236919A
[Patent Document 9] JP 2000-305270A
[Patent Document 10] JP 2002-99088A
[Patent Document 11] JP 2002-99089A
[Patent Document 12] JP 2002-49152A
[Patent Document 13] JP 2003-183227A
[Patent Document 14] JP 2002-328466A
[Patent Document 15] JP 2004-191913A
[Patent Document 16] JP 2004-341482A
[Patent Document 17] JP 2005-91909A
[Patent Document 18] JP 2002-363123A
[Patent Document 19] JP 2001-312055A
[Patent Document 20] JP 2004-137262A
[Patent Document 21] WO 2005/081062
[Patent Document 22] JP 2005-309421A
[Patent Document 23] WO2005/029189
[Non-Patent Document 1] Proceedings of SPIE vol. 3999 (2000) P1202-1206

DISCLOSURE OF THE INVENTION

Problems to be Solved by the Invention

An object of the present invention is to provide a compound sensitive to radiation such as KrF excimer lasers, extreme ultraviolet rays, electron beams and X-rays and a radiation-sensitive composition. Another object of the present invention is to provide a solvent-soluble, non-polymeric radiation-sensitive composition having a high sensitivity, high resolution, high heat resistance, and high etching resistance, which can be produced by a simple process without using a metal catalyst.

Means for Solving the Problems

As a result of extensive research, the inventors have found that a composition containing a specific compound is useful for solving the above problems. Thus, the present invention relates to a radiation-sensitive composition containing 1 to 80% by weight of a solid component and 20 to 99% by weight of a solvent, wherein the radiation-sensitive composition contains a compound B which satisfies the following requirements of:
(a) having a structure derived from a polyphenol compound A by introducing an acid-dissociating group to at least one phenolic hydroxyl group of the polyphenol compound A which is synthesized by a condensation between a di- to tetrafunctional aromatic ketone or aromatic aldehyde each having 5 to 36 carbon atoms with a compound having 1 to 3 phenolic hydroxyl groups and 6 to 15 carbon atoms, and
(b) having a molecular weight of 400 to 2000, and wherein a total content of the compound B and a solubilizer C is 50 to 99.999% by weight of a total weight of the solid component.

BEST MODE FOR CARRYING OUT THE INVENTION

The present invention is described below in more detail.
The radiation-sensitive composition of the present invention contains 1 to 80% by weight of a solid component which is composed of a compound B and a solubilizer C and 20 to 99% by weight of a solvent. The total content of the compound B and solubilizer C is 50 to 99.999% by weight of the total weight of the solid component.

The compound B has a structure derived from a polyphenol compound A by introducing an acid-dissociating group to at least one phenolic hydroxyl group of the polyphenol compound A which is produced by the condensation reaction of a di- to tetrafunctional aromatic ketone or aromatic aldehyde having 5 to 36 carbon atoms with a compound having 1 to 3 phenolic hydroxyl groups and 6 to 15 carbon atoms. The molecular weight of the polyphenol compound A is 400 to 2000. The aromatic ketone or aromatic aldehyde is preferably trifunctional or tetrafunctional.

Examples of the aromatic ketone or aromatic aldehyde include dicarbonyl compounds, tricarbonyl compounds and tetracarbonyl compounds, each having a structure selected from biphenyl structure, naphthalene structure, terphenyl structure, phenanthrene structure, pyrene structure, fluorene structure, acenaphthene structure, benzophenone structure, xanthene structure, anthraquinone structure, and thioxanthene structure.

Examples of the difunctional aromatic ketone or aromatic aldehyde include diformylbenzene, diacetylbenzene, dibenzoylbenzene, diformyltoluene, diacetyltoluene, dibenzoyltoluene, diformylxylene, diacetylxylene, dibenzoylxylene, diformylnaphthalene, diacetylnaphthalene, dibenzoylnaphthalene, diformylbiphenyl, diacetylbiphenyl, dibenzoylbiphenyl, diformylterphenyl, diacetylterphenyl, dibenzoylterphenyl, diformylanthracene, diacetylanthracene, dibenzoylanthracene, diformylphenanthrene, diacetylphenanthrene, dibenzoylphenanthrene, diformylpyrene, diacetylpyrene, dibenzoylpyrene, diformylindacene, diacetylindacene, dibenzoylindacene, diformylphenalene, diacetylphenalene, dibenzoylphenalene, diformylacenaphthylene, diacetylacenaphthylene, dibenzoylacenaphthylene, diformylphenalene, diacetylphenalene, dibenzoylphenalene, diformylnaphthacene, diacetylnaphthacene, dibenzoylnaphthacene, diformylpentacene, diacetylpentacene, dibenzoylpentacene, diformyltriphenylene, diacetyltriphenylene, dibenzoyltriphenylene, diformylpyridine, diacetylpyridine, dibenzoylpyridine, diformylimidazole, diacetylimidazole, dibenzoylimidazole, diformylfuran, diacetylfuran, dibenzoylfuran, diformylthiazole, diacetylthiazole, dibenzoylthiazole, diformylflavone, diacetylflavone, dibenzoylflavone, diformylisoflavone, diacetylisoflavone, and dibenzoylisoflavone.

The difunctional aromatic ketone or aromatic aldehyde preferably has a naphthalene structure having 10 to 20 carbon atoms, more preferably has a naphthalene structure having 10 to 17 carbon atoms, still more preferably has a naphthalene structure having 10 to 14 carbon atoms, and particularly preferably has a naphthalene structure having 10 to 12 carbon atoms.

The difunctional aromatic ketone or aromatic aldehyde preferably has a terphenyl structure having 18 to 28 carbon atoms, more preferably has a terphenyl structure having 18 to 24 carbon atoms, still more preferably has a terphenyl structure having 18 to 20 carbon atoms, and particularly preferably has a terphenyl structure having 18 to 19 carbon atoms.

Examples of the difunctional aromatic ketone or aromatic aldehyde having the naphthalene structure include naphthalenedicarbaldehyde, methylnaphthalenedicarbaldehyde, dimethylnaphthalenedicarbaldehyde, trimethylnaphthalenedicarbaldehyde, diacetylnaphthalene, diacetylmethylnaphthalene, diacetyldimethylnaphthalene, and diacetyltrimethylnaphthalene.

Examples of the difunctional aromatic ketone or aromatic aldehyde having the terphenyl structure include terphenyldicarbaldehyde (for example, m-terphenyl-4,4"-dicarbaldehyde, p-terphenyl-4,4"-dicarbaldehyde and o-terphenyl-4,4"-dicarbaldehyde), methylterphenyldicarbaldehyde, dimethylterphenyldicarbaldehyde, trimethylterphenyldicarbaldehyde, diacetylterphenyl, diacetylmethylterphenyl, diacetyldimethylterphenyl, diacetyltrimethylterphenyl, ethylterphenyldicarbaldehyde, propylterphenyldicarbaldehyde, butylterphenyldicarbaldehyde, pentylterphenyldicarbaldehyde, hexylterphenyldicarbaldehyde, heptylterphenyldicarbaldehyde, octylterphenyldicarbaldehyde, nonylterphenyldicarbaldehyde, decanylterphenyldicarbaldehyde, cyclopropylterphenyldicarbaldehyde, cyclobutylterphenyldicarbaldehyde, cyclopentylterphenyldicarbaldehyde, cyclohexylterphenyldicarbaldehyde, cycloheptylterphenyldicarbaldehyde, cyclodecylterphenyldicarbaldehyde, phenylterphenyldicarbaldehyde, tolylterphenyldicarbaldehyde, xylylterphenyldicarbaldehyde, and naphthylterphenyldicarbaldehyde.

Of the above difunctional aromatic ketones or aromatic aldehydes, preferred are naphthalene-2,5-dicarbaldehyde, naphthalene-2,6-dicarbaldehyde, naphthalene-2,7-dicarbaldehyde, 2,5-acetylnaphthalene, 2,6-acetylnaphthalene, 2,7-acetylnaphthalene, m-terphenyl-4,4"-dicarbaldehyde, p-terphenyl-4,4"-dicarbaldehyde, and o-terphenyl-4,4"-dicarbaldehyde; more preferred are naphthalene-2,6-dicarbaldehyde, naphthalene-2,7-dicarbaldehyde, m-terphenyl-4,4"-dicarbaldehyde, and p-terphenyl-4,4"-dicarbaldehyde; and still more preferred is naphthalene-2,6-dicarbaldehyde.

Examples of the trifunctional aromatic ketone or aromatic aldehyde include triformylbenzene, triacetylbenzene, tribenzoylbenzene, triformyltoluene, triacetyltoluene, tribenzoyltoluene, triformylxylene, triacetylxylene, tribenzoylxylene, triformylnaphthalene, triacetylnaphthalene, tribenzoylnaphthalene, triformylbiphenyl, triacetylbiphenyl, tribenzoylbiphenyl, triformylterphenyl, triacetylterphenyl, tribenzoylterphenyl, triformylanthracene, triacetylanthracene, tribenzoylanthracene, triformylphenanthrene, triacetylphenanthrene, tribenzoylphenanthrene, triformylpyrene, triacetylpyrene, tribenzoylpyrene, triformylindacene, triacetylindacene, tribenzoylindacene, triformylphenalene, triacetylphenalene, tribenzoylphenalene, triformylacenaphthylene, triacetylacenaphthylene, tribenzoylacenaphthylene, triformylphenalene, triacetylphenalene, triformylnaphthacene, triacetylnaphthacene, tribenzoylnaphthacene, triformylpentacene, triacetylpentacene, tribenzoylpentacene, triformyltriphenylene, triacetyltriphenylene, tribenzoyltriphenylene, triformylpyritholine, triacetyl pyritholine, tribenzoyl pyritholine, triformylimidazole, triacetylimidazole, tribenzoylimidazole, triformylfuran, triacetylfuran, tribenzoylfuran, triformylthiazole, triacetylthiazole, tribenzoylthiazole, triformylflavone, triacetylflavone, tribenzoylflavone, triformylisoflavone, triacetylisoflavone, and tribenzoylisoflavone.

Of the above trifunctional aromatic ketone or aromatic aldehyde, more preferred are triformylbenzene, triacetylbenzene, triformylnaphthalene, triacetylnaphthalene, triformylbiphenyl, and triacetylbiphenyl; still more preferred are triformylbenzene and triformylnaphthalene; and particularly preferred is triformylbenzene.

Examples of the tetrafunctional aromatic ketone or aromatic aldehyde include tetraformylbenzene, tetraacetylbenzene, tetrabenzoylbenzene, tetraformylnaphthalene, tetraacetylnaphthalene, tetrabenzoylnaphthalene, tetraformylbiphenyl, tetraacetylbiphenyl, tetrabenzoylbiphenyl, tetraformylterphenyl, tetraacetylterphenyl, tetrabenzoylterphenyl, tetraformylanthracene, tetraacetylanthracene, tetrabenzoylanthracene, tetraformylphenanthrene, tetraacetylphenanthrene, tetrabenzoylphenanthrene, tetraformylpyrene, tetraacetylpyrene, tetrabenzoylpyrene, tetraformylindacene, tetraacetylindacene, tetrabenzoylindacene, tetraformylphenalene, tetraacetylphenalene, tetrabenzoylphenalene, tetraformylacenaphthylene, tetraacetylacenaphthylene, tetrabenzoylacenaphthylene, tetraformylphenalene, tetraacetylphenalene, tetrabenzoylphenalene, tetraformylnaphthacene, tetraacetylnaphthacene, tetrabenzoylnaphthacene, tetraformylpentacene, tetraacetylpentacene, tetrabenzoylpentacene, tetraformyltetraphenylene, tetraacetyltetraphenylene, tetrabenzoyltetraphenylene, tetraformyl pyritetrane, tetraacetyl pyritetrane, tetrabenzoyl pyritetrane, tetraformylimidazole, tetraacetylimidazole, tetrabenzoylimidazole, tetraformylfuran, tetraacetylfuran, tetrabenzoylfuran, tetraformylthiazole, tetraacetylthiazole, tetrabenzoylthiazole, tetraformylflavone, tetraacetylflavone, tetrabenzoylflavone, tetraformylisoflavone, tetraacetylisoflavone, and tetrabenzoylisoflavone.

Of the above tetrafunctional aromatic ketone or aromatic aldehyde, more preferred are tetraformylbenzene, tetraacetylbenzene, tetraformylnaphthalene, tetraacetylnaphthalene, tetraformylbiphenyl, tetraacetylbiphenyl, tetraformylterphenyl, and tetraacetylterphenyl and still more preferred are tetraformylbenzene and tetraformylnaphthalene.

The di- to tetrafunctional aromatic ketone or aromatic aldehyde having 5 to 36 carbon atoms may be produced by any of known methods, for example, by a method of reducing methyl naphthalenedicarboxylate or methyl benzenetricarboxylate with a reducing agent; a method of reducing naphthalenedinitrile or benzenetrinitrile with a reducing agent or hydrogen in the presence of a catalyst; a method of oxidizing pendant methyl group of an alkyl aromatic compound such as dimethylnaphthalene and trimesine in air; a method of oxidizing a chlorinated aromatic compound which is obtained by photo-chlorinating the pendant group of an alkyl aromatic compound such as dimethylnaphthalene and trimesine a method of oxidizing an aromatic carboxylic acid halide such as naphthalenedicarboxylyl halide and trimesyl halide with an oxidizing agent; and a method of oxidizing dihydroxymethylnaphthalene and trihydroxymethylbenzene with an oxidizing agent.

The compound B preferably has a conjugated structure which is constituted by at least two benzene rings and/or a nonbonding electron pair of hetero atom. With such conjugated structure, the compound B, irrespective of its low molecular weight, has a good film-forming property, high etching resistance, high heat resistance, small outgas amount upon the irradiation with radiations, high sensitivity due to sensitizing effect. The sensitizing effect is attributable to an efficient transfer of a partial energy of radiations such as electron beams absorbed by the conjugated structure. If the aromatic ketone or aromatic aldehyde is trifunctional or tetrafunctional, the compound B acquires the film-forming property, heat resistance, etc. without the conjugated structure.

Examples of the conjugated structure include biphenyl structure, naphthalene structure, fluorene structure, anthracene structure, phenanthrene structure, pyrene structure, benzopyrene structure, acenaphthene structure, acenaphthylene structure, 1-ketoacenaphthene structure, benzophenone structure, xanthene structure, thioxanthene structure, flavone structure, isoflavone structure, indane structure, indene structure, indacene structure, phenalene structure, biphenylene structure, coronene structure, chrysene structure, trinaphthylene structure, hexaphene structure, hexacene structure, rubicene structure, fluoranthene structure, acephenanthrylene structure, perylene structure, picene structure, pentaphene structure, heptaphene structure, heptacene structure, pyranthrene structure, phenacene structure, naphthacene structure, pentacene structure, aceanthrene structure, acephenanthrene structure, azulene structure, triphenylene structure, p-terphenyl structure, m-terphenyl structure, 1,3,5-triphenylbenzene structure, 1,2,3-triphenylbenzene structure, 1,2,4-triphenylbenzene structure, phenylnaphthalene structure, binaphthalene structure, and ovalene structure, with at least one structure selected from biphenyl structure, naphthalene structure, anthracene structure, phenanthrene structure, pyrene structure, fluorene structure, acenaphthene structure, 1-ketoacenaphthene structure, benzophenone structure, xanthene structure, and thioxanthene structure being preferred because they can be introduced into the compound B using starting compounds of relatively low costs. More preferred are naphthalene structure and/or terphenyl structure, and particularly preferred is naphthalene structure.

The aromatic aldehyde is preferable to the aromatic ketone, because the aromatic aldehyde has a higher reactivity and less produces by-products to enable the production of the polyphenol compound A in higher yields.

Examples of the compound having 6 to 15 carbon atoms and phenolic hydroxyl groups include phenol, ($C_{1-6}$ alkyl)phenol (cresols such as o-cresol, m-cresol and p-cresol), dialkylphenol (for example, 2,3-dimethylphenol, 2,5-dimethylphenol, 2,6-dimethylphenol, 2-ethyl-5-methylphenol, and thymol), trialkylphenol (for example, 2,3,6-trimethylphenol), alkoxyphenol (anisol such as 2-methoxyphenol), arylphenol (phenylphenol such as 3-phenylphenol), cycloalkylphenol (for example, 3-cyclohexylphenol), halogenated phenols (for example, chlorophenol, dichlorophenol, chlorocresol, bromophenol, and dibromophenol), other phenols (for example, naphthol and 5,6,7,8-tetrahydronaphthol), and polyphenols (for example, catechol, alkylcatechol, chlorocatechol, resorcinol, alkylresorcinol, hydroquinone, alkylhydroquinone, chlororesorcinol, chlorohydroquinone, pyrogallol, alkylpyrogallol, phloroglucinol, and 1,2,4-trihydroxyphenol). Preferred are 2,5-xylenol, 2,6-xylenol, thymol and 2,3,6-trimethylphenol, more preferred are 2,6-xylenol and 2,3,6-trimethylphenol, and still more preferred is 2,3,6-trimethylphenol. The above compounds may be used alone or in combination of two or more. The purity is not critical, and generally 95% by weight or more, preferably 99% by weight or more.

The acid-dissociating group is selected from those employed in the hydroxystyrene resins and (meth)acrylic acid resins which are used in the chemical-amplified resist composition for KrF and ArF. Examples thereof include substituted methyl groups, 1-substituted ethyl groups, 1-substituted n-propyl groups, 1-branched alkyl groups, silyl groups, acyl groups, 1-substituted alkoxymethyl groups, cyclic ether groups, and alkoxycarbonyl groups. The acid-dissociating group is preferably free from a crosslinkable functional group.

The molecular weight of the compound B is 400 to 2000, preferably 500 to 1600, and more preferably 550 to 1600. Within the above range, the resolution is improved while maintaining the film-forming property necessary for the resists.

In a preferred embodiment of the present invention, the compound B is preferably represented by the following formula 1:

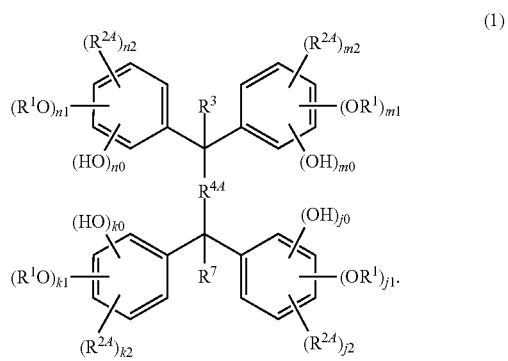

In the formula 1, $R^1$ is an acid-dissociating group selected from substituted methyl groups, 1-substituted ethyl groups, 1-substituted n-propyl groups, 1-branched alkyl groups, silyl groups, acyl groups, 1-substituted alkoxymethyl groups, cyclic ether groups and alkoxycarbonyl groups.

Example of the substituted methyl group include methoxymethyl group, methylthiomethyl group, ethoxymethyl group, n-propoxymethyl group, isopropoxymethyl group, n-butoxymethyl group, t-butoxymethyl group, 2-methylpropoxymethyl group, ethylthiomethyl group, methoxyethoxymethyl group, phenyloxymethyl group, 1-cyclopentyloxymethyl group, 1-cyclohexyloxymethyl group, benzylthiomethyl group, phenacyl group, 4-bromophenacyl group, 4-methoxyphenacyl group, piperonyl group, methoxycarbonylmethyl group, ethoxycarbonylmethyl group, n-propoxycarbonylmethyl group, isopropoxycarbonylmethyl group, n-butoxycarbonylmethyl group, tert-butoxycarbonylmethyl group, and the following groups represented by the formulae 2-1 to 2-13.

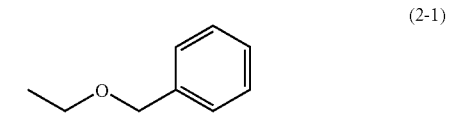

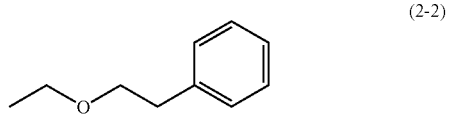

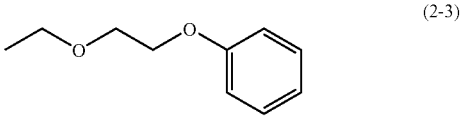

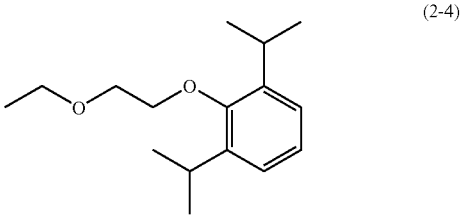

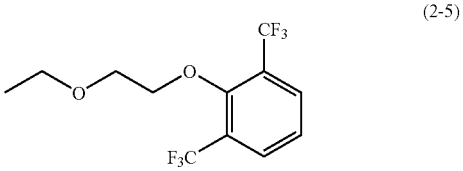

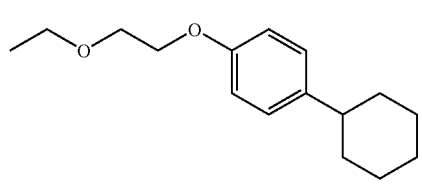 (2-6)

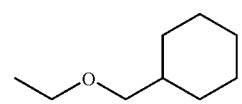 (2-7)

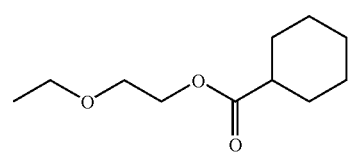 (2-8)

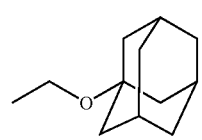 (2-9)

 (2-10)

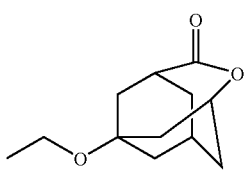 (2-11)

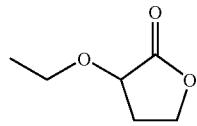 (2-12)

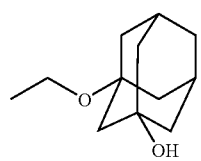 (2-13)

Examples of the 1-substituted ethyl group include 1-methoxyethyl group, 1-methylthioethyl group, 1,1-dimethoxyethyl group, 1-ethoxyethyl group, 1-ethylthioethyl group, 1,1-diethoxyethyl group, n-propoxyethyl group, isopropoxyethyl group, n-butoxyethyl group, t-butoxyethyl group, 2-methylpropoxyethyl group, 1-phenoxylethyl group, 1-phenylthioethyl group, 1,1-diphenoxylethyl group, 1-cyclopentyloxyethyl group, 1-cyclohexyloxyethyl group, 1-phenylethyl group, 1,1-diphenylethyl group, and the following groups represented by the formulae 3-1 to 3-13.

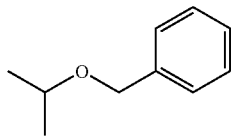 (3-1)

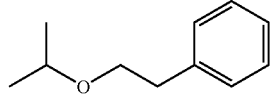 (3-2)

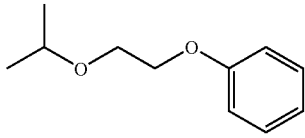 (3-3)

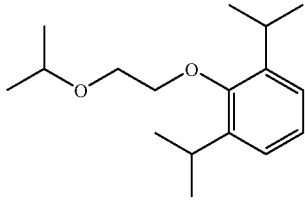 (3-4)

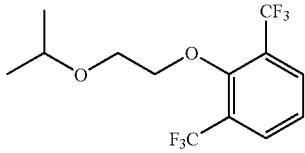 (3-5)

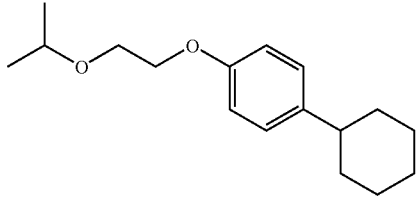 (3-6)

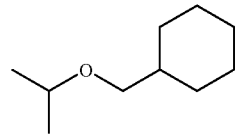 (3-7)

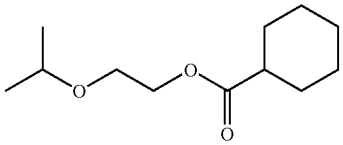 (3-8)

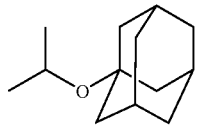 (3-9)

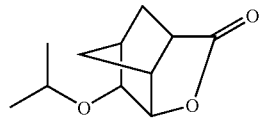 (3-10)

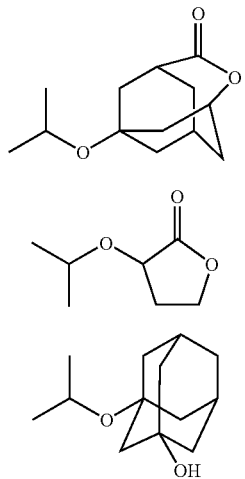

(3-11)

(3-12)

(3-13)

Examples of the 1-substituted n-propyl group include 1-methoxy-n-propyl group and 1-ethoxy-n-propyl group.

Examples of the 1-branched alkyl group include isopropyl group, sec-butyl group, tert-butyl group, 1,1-dimethylpropyl group, 1-methylbutyl group, 1,1-dimethylbutyl group, 2-methyladamantyl group, and 2-ethyladamantyl group.

Examples of the silyl group include trimethylsilyl group, ethyldimethylsilyl group, methyldiethylsilyl group, triethylsilyl group, tert-butyldimethylsilyl group, tert-butyldiethylsilyl group, tert-butyldiphenylsilyl group, tri-tert-butylsilyl group, and triphenylsilyl group.

Examples of the acyl group include acetyl group, phenoxylacetyl group, propionyl group, butyryl group, heptanoyl group, hexanoyl group, valeryl group, pivaloyl group, isovaleryl group, lauroyl group, adamantyl group, benzoyl group, and naphthoyl group.

Examples of the 1-substituted alkoxymethyl group include 1-cyclopentylmethoxymethyl group, 1-cyclopentylethoxymethyl group, 1-cyclohexylmethoxymethyl group, 1-cyclohexylethoxymethyl group, 1-cyclooctylmethoxymethyl group, and 1-adamantylmethoxymethyl group.

Examples of the cyclic ether group include tetrahydropyranyl group, tetrahydrofuranyl group, tetrahydrothiopyranyl group, tetrahydrothiofuranyl group, 4-methoxytetrahydropyranyl group, and 4-methoxytetrahydrothiopyranyl group.

Examples of the alkoxycarbonyl group include methoxycarbonyl group, ethoxycarbonyl group, n-propoxycarbonyl group, isopropoxycarbonyl group, n-butoxycarbonyl group, and tert-butoxycarbonyl group.

Of the above acid-dissociating groups, preferred are the substituted methyl groups, substituted ethyl groups, 1-substituted alkoxymethyl groups, cyclic ether groups, and alkoxycarbonyl groups, more preferred are the substituted methyl groups and substituted ethyl groups in view of high sensitivity, still more preferred are 1-ethoxyethyl group and cyclohexyloxyethyl group, and particularly preferred is cyclohexyloxyethyl group in view of high resolution.

The acid-dissociating group $R^1$ of the formula 1 may be a group having a repeating unit represented by the following formula 4-1 and a terminal group represented by the following formula 4-2:

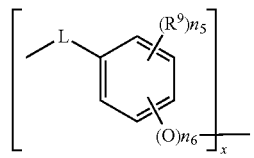

(4-1)

and

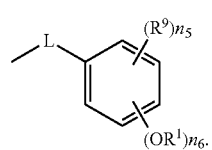

(4-2)

In the formula 4-1 and formula 4-2, $R^1$ is the same as defined above. L is a single bond, methylene group, ethylene group or carbonyl group. Two or more L groups may be the same or different. The subscript n5 is an integer of 0 to 4, n6 is an integer of 1 to 3, and x is an integer of 0 to 3, satisfying $1 \leq n5+n6 \leq 5$. Two or more subscripts n5, n6 or x may be the same or different. $R^9$ is a group selected from the group consisting of halogen atom, alkyl group, cycloalkyl group, aryl group, aralkyl group, alkoxy group, aryloxy group, alkenyl group, acyl group, alkoxycarbonyl group, alkyloyloxy group, aryloyloxy group, cyano group, and nitro group. The halogen atom may include chlorine atom, bromine atom and iodine atom; the alkyl group may include alkyl group having 1 to 4 carbon atoms such as methyl group, ethyl group, propyl group, n-propyl group, n-butyl group, isobutyl group, sec-butyl group, and tert-butyl group; the cycloalkyl group may include cyclohexyl group, norbornyl group, and adamantyl group; the aryl group may include phenyl group, tolyl group, xylyl group, and naphthyl group; the aralkyl group may include benzyl group, hydroxybenzyl group, and dihydroxybenzyl group; the alkoxy group may include alkoxy groups having 1 to 4 carbon atoms such as methoxy group, ethoxy group, hydroxyethoxy group, propoxy group, hydroxypropoxy group, isopropoxy group, n-butoxy group, isobutoxy group, sec-butoxy group, and tert-butoxy group; the aryloxy group may include phenoxyl group; the alkenyl group may include alkenyl groups having 2 to 4 carbon atoms such as vinyl group, propenyl group, allyl group, and butenyl group; the acyl group may include aliphatic acyl groups having 1 to 6 carbon atoms such as formyl group, acetyl group, propionyl group, butyryl group, valeryl group, isovaleryl group and pivaloyl group, and aromatic acyl groups such as benzoyl group and toluoyl group; the alkoxycarbonyl group may include alkoxycarbonyl groups having 2 to 5 carbon atoms such as methoxycarbonyl group, ethoxycarbonyl group, propoxycarbonyl group, isopropoxycarbonyl group, n-butoxycarbonyl group, isobutoxycarbonyl group, sec-butoxycarbonyl group, and tert-butoxycarbonyl group; the alkyloyloxy group may include acetoxy group, propionyloxy group, butyryloxy group, isobutyryloxy group, valeryloxy group, isovaleryloxy group, and pivaloyloxy group; and the aryloyloxy group may include benzoyloxy group. Two or more $R^9$ groups may be the same or different.

$R^{2A}$ is a group selected from the group consisting of halogen atom, alkyl group, cycloalkyl group, aryl group, aralkyl group, alkoxy group, aryloxy group, alkenyl group, acyl group, alkoxycarbonyl group, alkyloyloxy group, aryloyloxy group, cyano group, and nitro group. Two or more $R^{2A}$ may be the same or different. The halogen atom may include chlorine atom, bromine atom and iodine atom; the alkyl group may include alkyl groups having 1 to 4 carbon atoms such as methyl group, ethyl group, propyl group, n-propyl group, n-butyl group, isobutyl group, sec-butyl group, and tert-butyl group; cycloalkyl group may include cyclohexyl group, norbornyl group, and adamantyl group; the aryl group may include phenyl group, tolyl group, xylyl group, and naphthyl group; the aralkyl group may include benzyl group, hydroxybenzyl group, and dihydroxybenzyl group; the alkoxy group may include alkoxy groups having 1 to 4 carbon atoms such as methoxy group, ethoxy group, hydroxyethoxy group, propoxy group, hydroxypropoxy group, isopropoxy group, n-butoxy group, isobutoxy group, sec-butoxy group, and tert-butoxy group; the aryloxy group may include phenoxyl group; the alkenyl group may include alkenyl groups having 2 to 4 carbon atoms such as vinyl group, propenyl group, allyl group, and butenyl group; the acyl group may include aliphatic acyl groups having 1 to 6 carbon atoms such as formyl group, acetyl group, propionyl group, butyryl group, valeryl group, isovaleryl group and pivaloyl group, and aromatic acyl groups such as benzoyl group and toluoyl group; the alkoxycarbonyl group may include alkoxycarbonyl groups having 2 to 5 carbon atoms such as methoxycarbonyl group, ethoxycarbonyl group, propoxycarbonyl group, isopropoxycarbonyl group, n-butoxycarbonyl group, isobutoxycarbonyl group, sec-butoxycarbonyl group, and tert-butoxycarbonyl group; the alkyloyloxy group may include acetoxy group, propionyloxy group, butyryloxy group, isobutyryloxy group valeryloxy group, isovaleryloxy group, and pivaloyloxy group; and the aryloyloxy group may include benzoyloxy group.

$R^{2A}$ groups are preferably methyl groups on 2 and 5-positions, 2 and 6-positions, or 2, 3 and 5-positions with respect to the phenolic hydroxyl group, or preferably isopropyl group on 2-position and methyl group on 5-position each with respect to the phenolic hydroxyl group. Satisfying the above requirement, the crystallizability is controlled, the film-forming property is improved and the solution contrast is increased, to provide patterns excellent in the resolution and pattern shape.

The hydroxyl group in $R^{2A}$ may be substituted by the acid-dissociating group represented by $R^1$ as long as the effect of the present invention is adversely affected.

Each of $R^3$ and $R^7$ is a hydrogen atom or alkyl group having 1 to 6 carbon atoms. Examples of the alkyl group having 1 to 6 carbon atoms include linear, branched or cyclic alkyl groups such as methyl group, ethyl group, n-propyl group, isopropyl group, n-butyl group, isobutyl group, sec-butyl group, t-butyl group, pentyl group, hexyl group, and cyclohexyl group.

$R^{4A}$ is a divalent group having 10 to 28 carbon atoms which includes a biphenyl structure, terphenyl structure, naphthalene structure, phenanthrene structure, or pyrene structure. Alternatively, $R^{4A}$ together with $R^3$ and $R^7$ represents a tetravalent group having 10 to 28 carbon atoms which includes a fluorene structure or benzophenone structure.

$R^{4A}$ is preferably the following groups represented by the formulae 5-1 to 5-3:

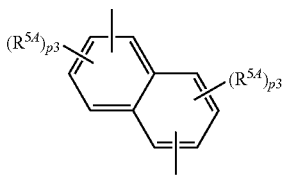

(5-1)

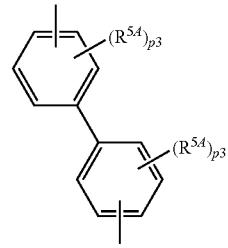

(5-2)

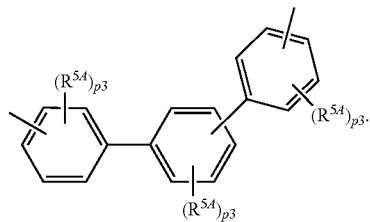

(5-3)

In the above formulae, $R^{5A}$ is independently an alkyl group having 1 to 10 carbon atoms, cycloalkyl group having 3 to 10 carbon atoms, or aryl group having 6 to 10 carbon atoms. Examples of the alkyl group having 1 to 10 carbon atoms include linear or branched alkyl groups such as methyl group, ethyl group, n-propyl group, isopropyl group, n-butyl group, isobutyl group, sec-butyl group, t-butyl group, pentyl group, hexyl group, heptyl group, octyl group, nonyl group, and decanyl group, with methyl group being preferred. Examples of the cycloalkyl group having 3 to 10 carbon atoms include cyclopropyl group, cyclobutyl group, cyclopentyl group, cyclohexyl group, cycloheptyl group, and cyclodecyl group, with cyclohexyl group being preferred. Examples of the aryl group having 6 to 10 carbon atoms include phenyl group, tolyl group, xylyl group, and naphthyl group, with phenyl group being preferred. The subscript p3 is an integer of 0 to 3. Two or more $R^{5A}$ groups or two or more subscripts p3 may be the same or different, respectively.

The tetravalent groups represented by $R^{4A}$ bonded to $R^3$ and $R^7$ are preferably the following groups represented by formulae 6-1 and 6-2:

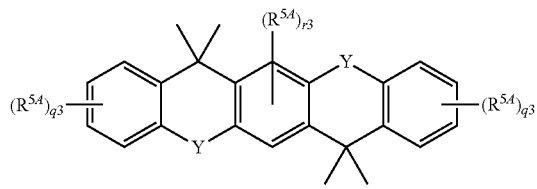

(6-1)

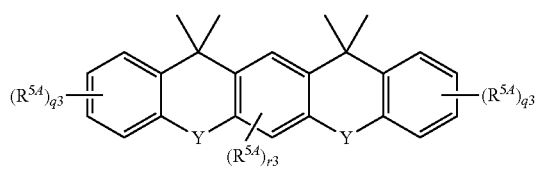

(6-2)

wherein $R^{5A}$ is the same as defined above; Y is a single bond or carbonyl group; q3 is an integer of 0 to 3; r3 is an integer of 0 to 2. Two or more $R^{5A}$, Y, q3 or r3 may be the same or different, respectively.

In the formula 1, each of k0, j0, m0, and n0 is an integer of 0 to 3, each of k1, j1, m1, and n1 is an integer of 0 to 3, and each of k2, j2, m2, and n2 is an integer of 0 to 4, satisfying $1\leq k0+k1+k2\leq 5$, $1\leq j0+j1+j2\leq 5$, $1\leq m0+m1+m2\leq 5$, $1\leq n0+n1+n2\leq 5$, $1\leq k1+j+m1+n1\leq 12$, $1\leq k0+k1\leq 3$, $1\leq j0+j1\leq 3$, $1\leq m0+m1\leq 3$, and $1\leq n0+n1\leq 3$.

Since the compound of the formula 1 is, irrespective of its low molecular weight, excellent in the film-forming property, heat resistance, dry-etching resistance and permeability to EUV, and low in the outgas, it is useful as the resist component of radiation-sensitive compositions. The radiation-sensitive composition containing the compound of the formula 1 is excellent in the resolution and sensitivity and provides patterns with small line edge roughness.

The compound of the formula 1 is preferably represented by the following formula 7-1 or 7-2.

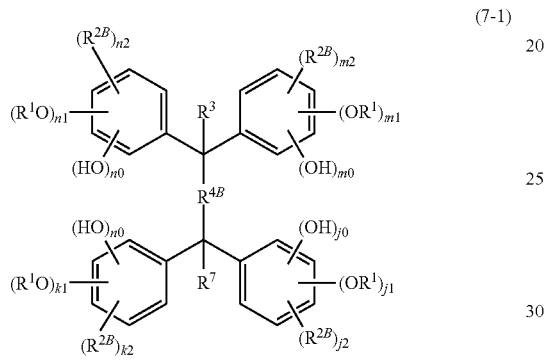

(7-1)

In the formula 7-1, $R^1$, $R^3$, $R^7$, k0, j0, m0, n0, k1, j1, m1, n1, k2, j2, m2, and n2 are the same as defined above; $R^{2B}$ is a group selected from the group consisting of halogen atom, alkyl group, aryl group, aralkyl group, alkoxy group, alkenyl group, acyl group, alkoxycarbonyl group, alkyloyloxy group, aryloyloxy group, cyano group and nitro group; $R^{4B}$ is a divalent group having 10 to 20 carbon atoms which includes a naphthalene structure. Tow or more $R^1$ or $R^{2B}$ may be the same or different, respectively.

The naphthalene structure is rigid and imparts the heat resistance to resist materials. In addition, a high sensitivity is achieved because the energy transfer to the acid generator is made more efficient by the sensitizing effect of its broad Π-conjugated structure. The naphthalene structure well transmits EUV because of its high carbon density, little outgases upon exposure to high energy rays, and exhibit a good dry-etching resistance.

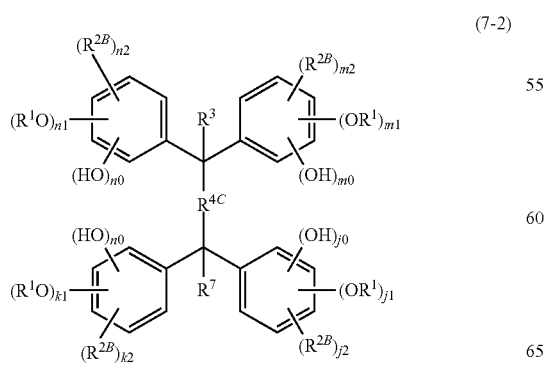

(7-2)

In the formula 7-2, $R^1$, $R^{2B}$, $R^3$, $R^7$, k0, j0, m0, n0, k1, j1, m1, n1, k2, j2, m2, and n2 are the same as defined above; and $R^{4C}$ is a divalent group having 18 to 28 carbon atoms which includes a terphenyl structure.

The terphenyl structure is rigid and imparts the heat resistance to resist materials. In addition, a high sensitivity is achieved because the energy transfer to the acid generator is made more efficient by the sensitizing effect of its broad Π-conjugated structure. The terphenyl structure well transmits EUV because of its high carbon density, little outgases upon exposure to high energy rays, and exhibit a good dry-etching resistance.

The compound of the formula 7-1 to 7-2 is preferably represented by the following formula 8-1, 8-2, 8-3 or 8-4:

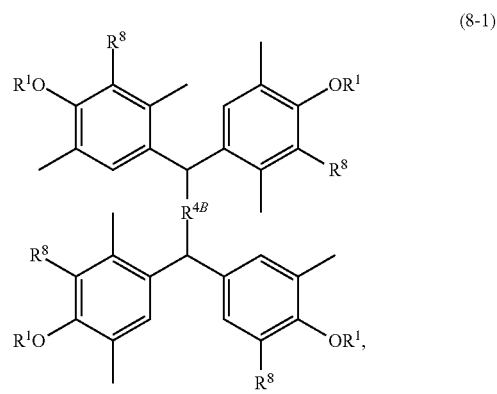

(8-1)

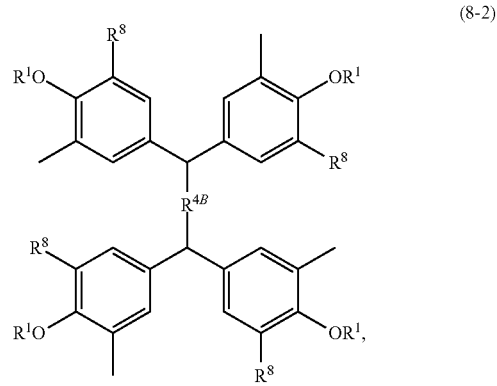

(8-2)

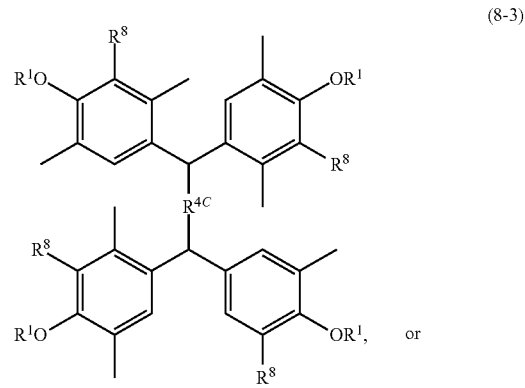

(8-3)

or

-continued

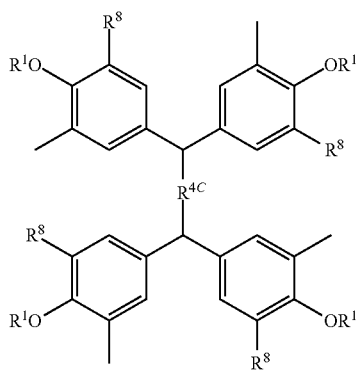

(8-4)

wherein $R^1$, $R^{4B}$, and $R^{4C}$ are the same as defined above, and $R^8$ is independently a hydrogen atom or methyl group. Two or more $R^8$ may be the same or different, but, at least one of them is methyl group.

The compound of the formula 7-1 is preferably represented by the following formula 9-1:

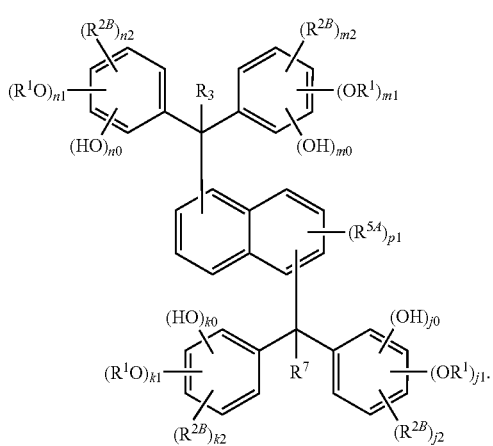

(9-1)

In the formula 9-1, $R^1$, $R^{2B}$, $R^3$, $R^7$, k0, j0, m0, n0, k1, j1, m1, n1, k2, j2, m2, and n2 are the same as defined above; $R^{5A}$ is independently an alkyl group having 1 to 10 carbon atoms, cycloalkyl group having 3 to 10 carbon atoms, or aryl group having 6 to 10 carbon atoms; and p1 is an integer of 0 to 6. Two or more $R^1$, $R^{2B}$ and $R^{5A}$ may be the same or different, respectively. Examples of the alkyl group having 1 to 10 carbon atoms include linear or branched alkyl group such as methyl group, ethyl group, n-propyl group, isopropyl group, n-butyl group, isobutyl group, sec-butyl group, t-butyl group, pentyl group, hexyl group, heptyl group, octyl group, nonyl group, and decanyl group. Examples of the cycloalkyl group having 3 to 10 carbon atoms include cyclopropyl group, cyclobutyl group, cyclopentyl group, cyclohexyl group, cycloheptyl group, and cyclodecyl group. Examples of the aryl group having 6 to 10 carbon atoms include phenyl group, tolyl group, xylyl group, and naphthyl group.

Further, the compound of the formula 7-1 is preferably represented by the following formula 9-2:

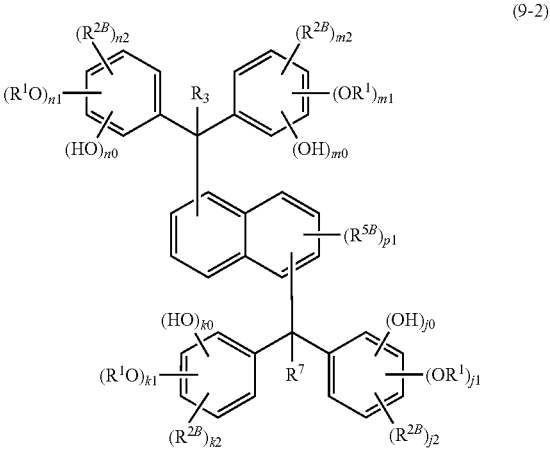

(9-2)

wherein $R^1$, $R^{2B}$, $R^3$, $R^7$, p1, k0, j0, m0, n0, k1, j1, m1, n1, k2, j2, m2, and n2 are the same as defined above; and $R^{5B}$ is an alkyl group having 1 to 6 carbon atoms. Two or more $R^1$, $R^{2B}$ and $R^{5B}$ may be the same or different, respectively.

The compound of the formula 9-1 is preferably represented by the following formula 10:

(10)

wherein $R^1$, $R^{2B}$, $R^3$, $R^{5A}$, $R^7$, p1, k0, j0, m0, n0, k1, j1, m1, n1, k2, j2, m2, and n2 are the same as defined above. The compound of the above formula is excellent in the sensitivity, heat resistance, and resolution. The compound can be produced from relatively cheap phenols and can be easily separated and purified.

The compound of the formula 10 is preferably represented by the following formula 10-2:

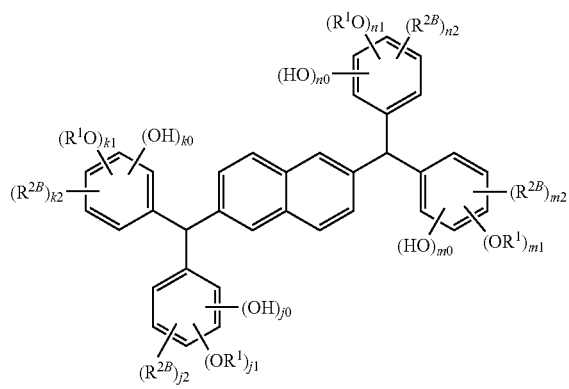
(10-2)

wherein $R^1$, $R^{2B}$, k0, j0, m0, n0, k1, j1, m1, n1, k2, j2, m2, and n2 are the same as defined above. The compound of the above formula is excellent in the sensitivity, heat resistance, and resolution. The compound can be produced from relatively cheap phenols and can be easily separated and purified.

The compound of the formula 10 is also preferably represented by the following formula 11:

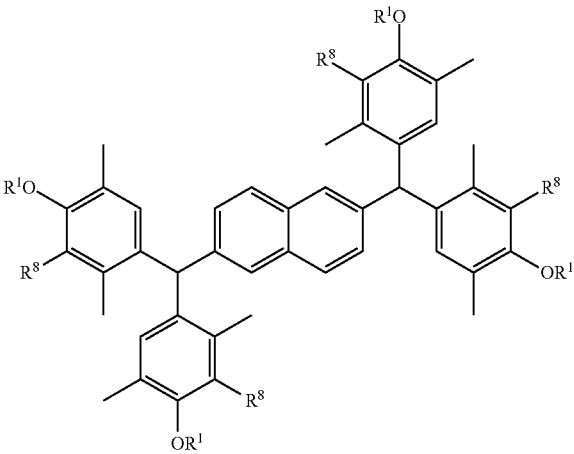
(11)

wherein $R^1$ and $R^8$ are the same as defined above. The compound of the above formula is excellent in the sensitivity, heat resistance, and resolution. The compound can be produced from relatively cheap phenols and can be easily separated and purified.

The compound of the formula 10 is also preferably represented by the following formulae 12-1 to 12-8:

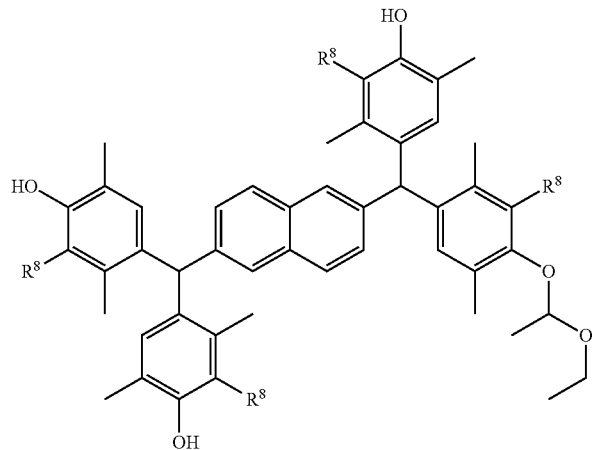
(12-1)

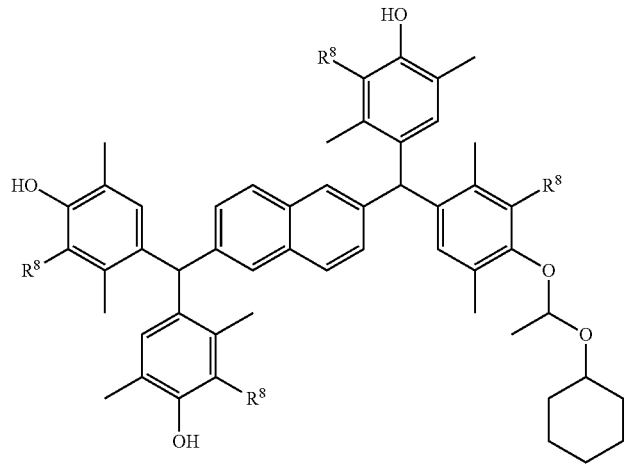
(12-2)

(12-3)
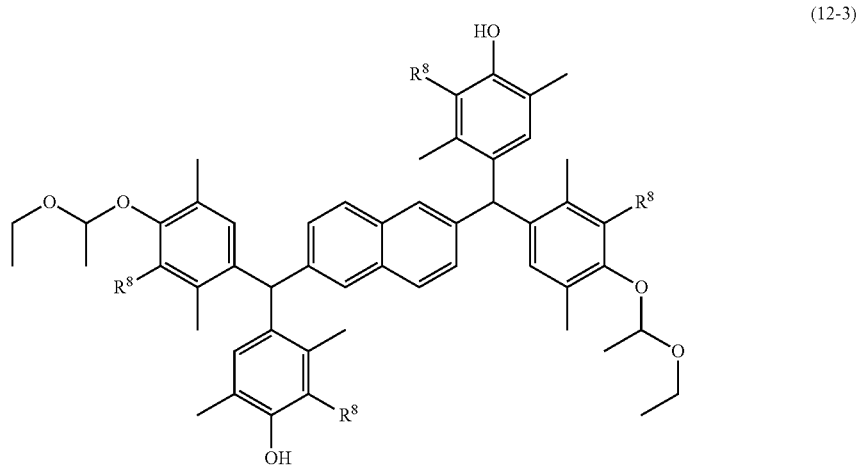
(12-4)
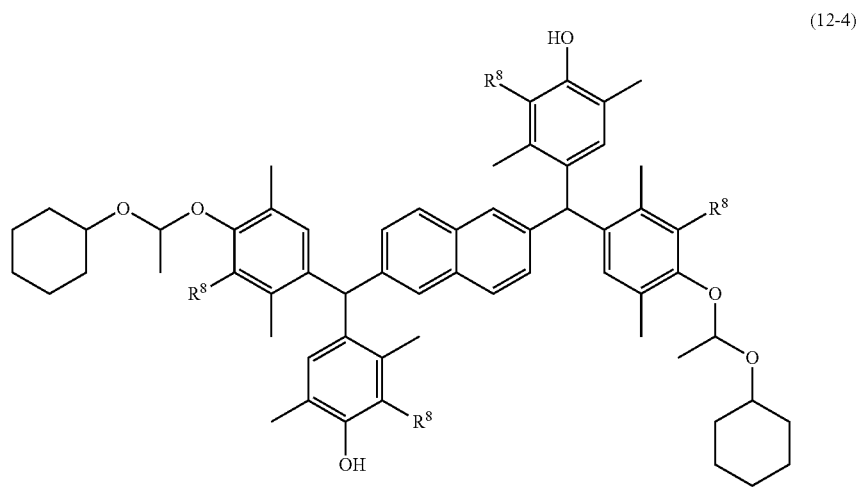
(12-5)
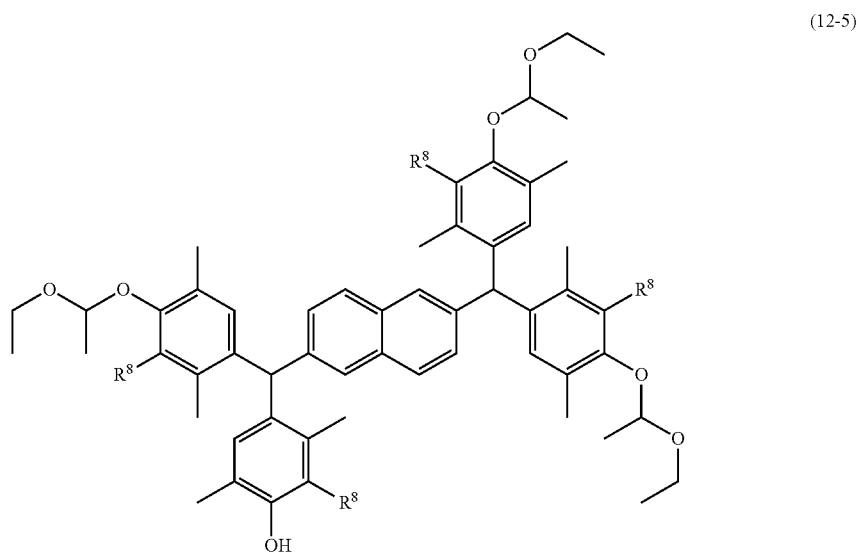

(12-6)
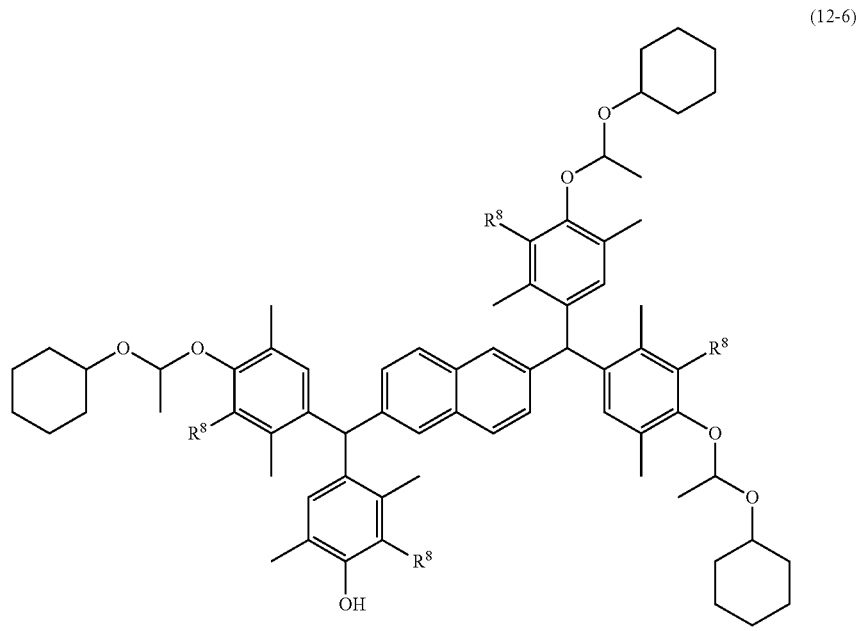
(12-7)
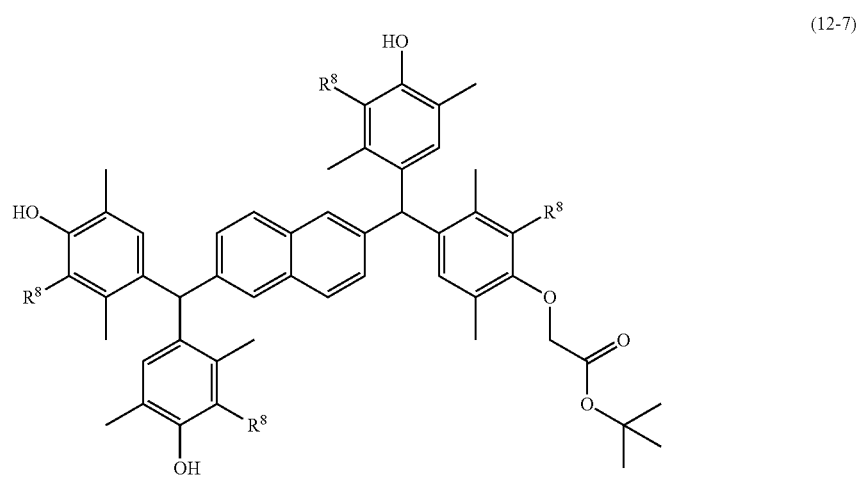
(12-8)
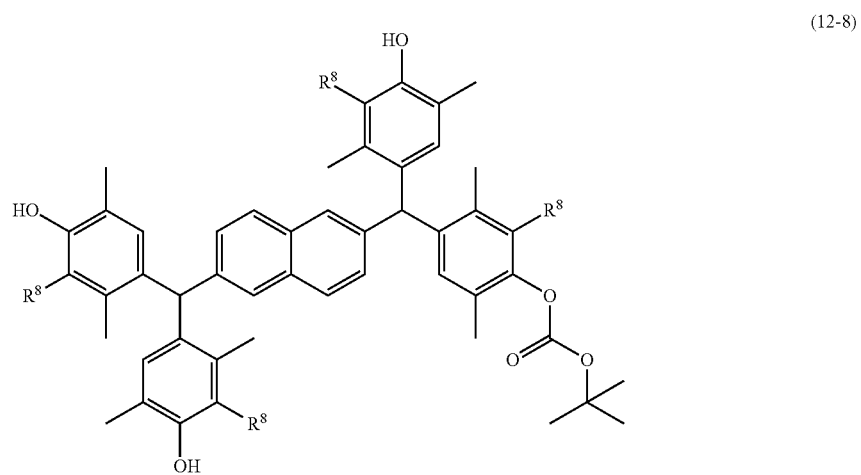

wherein $R^8$ is the same as defined above. The compounds of the above formulae are excellent in the resolution.

The compound of the formula 10 is also preferably represented by the following formula 13:

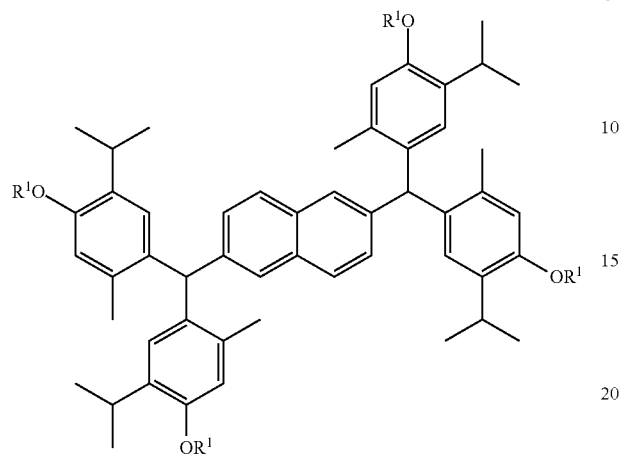

(13)

wherein $R^1$ is the same as defined above. The compound of the above formula is excellent in the sensitivity, heat resistance, and resolution. The compound can be produced from relatively cheap phenols and can be easily separated and purified.

The compound of the formula 10 is also preferably represented by the following formulae 14-1 to 14-8:

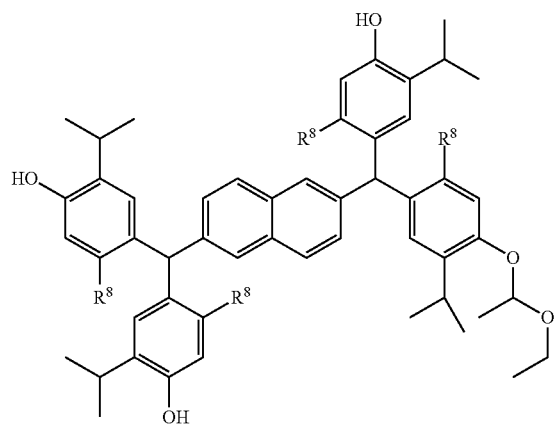

(14-1)

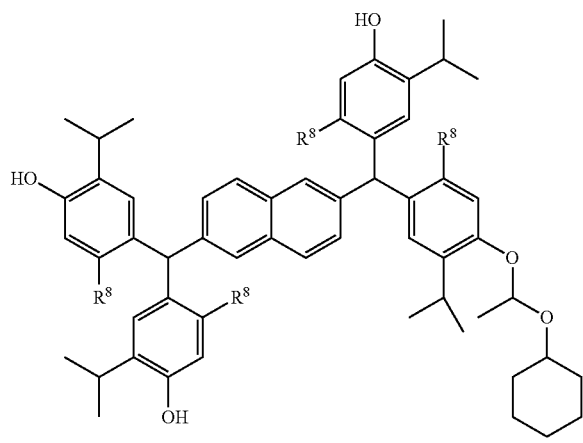

(14-2)

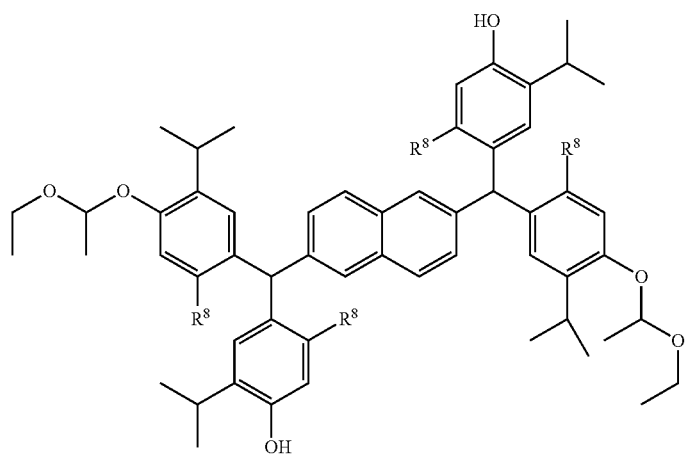

(14-3)

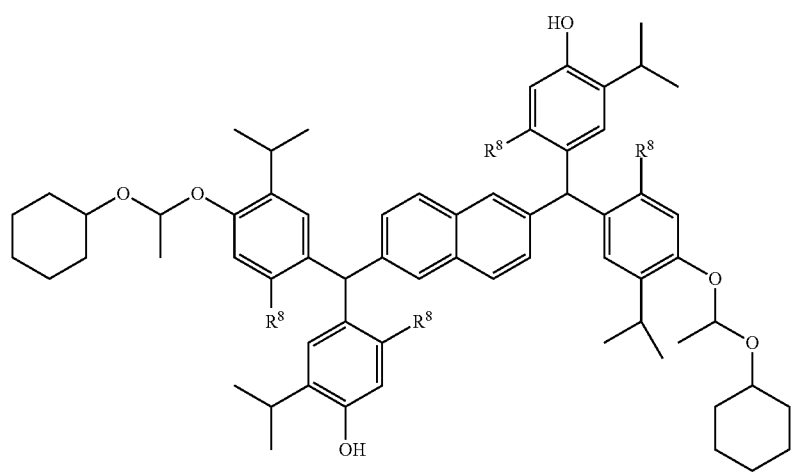
(14-4)
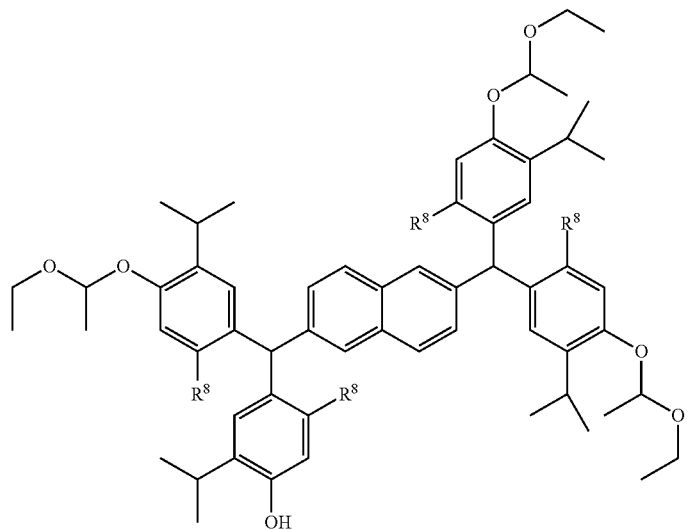
(14-5)
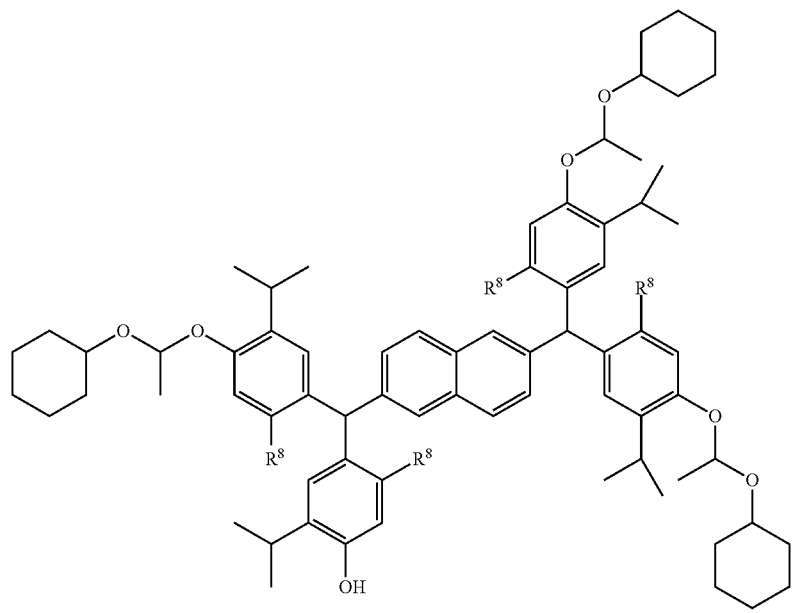
(14-6)

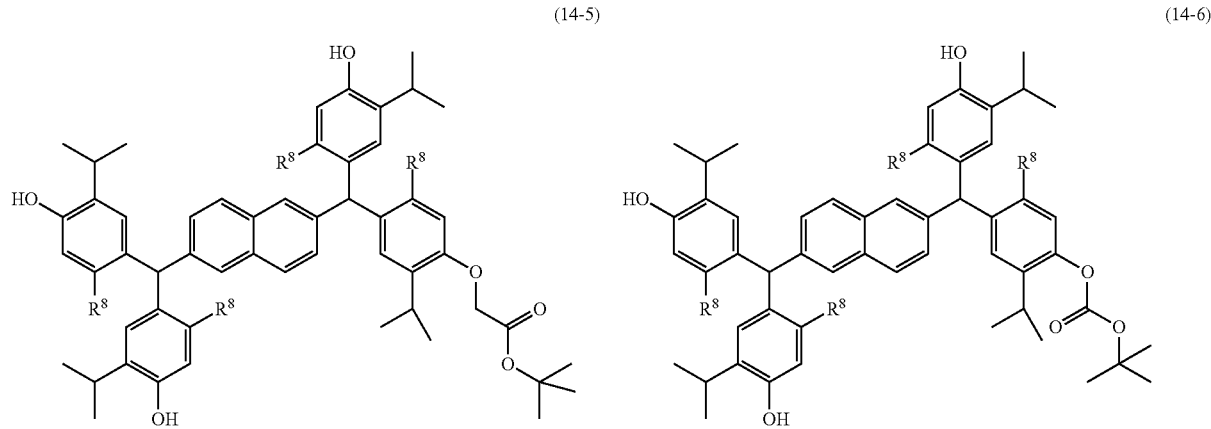

wherein $R^8$ is the same as defined above. The compounds of the above formulae are excellent in the resolution.

The compound of the formula 9-1 is preferably represented by the following formula 15:

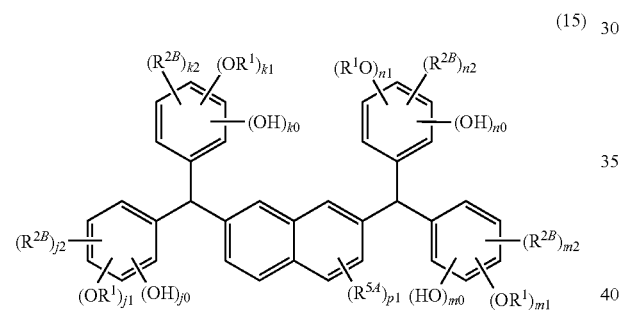

(15)

wherein $R^1$, $R^{2B}$, $R^3$, $R^{5A}$, $R^7$, p1, k0, j0, m0, n0, k1, j1, m1, n1, k2, j2, m2, and n2 are the same as defined above. The compound of the above formula is excellent in the sensitivity, heat resistance, and resolution. The compound can be produced from relatively cheap phenols and can be easily separated and purified.

The compound of the formula 15 is preferably represented by the following formula 16-2:

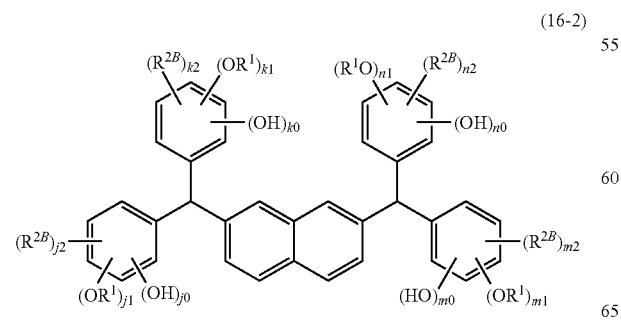

(16-2)

wherein $R^1$, $R^{2B}$, k0, j0, m0, n0, k1, j1, m1, n1, k2, j2, m2, and n2 are the same as defined above. The compound of the above formula is excellent in the sensitivity, heat resistance, and resolution. The compound can be produced from relatively cheap phenols and can be easily separated and purified.

The compound of the formula 15 is also preferably represented by the following formula 16:

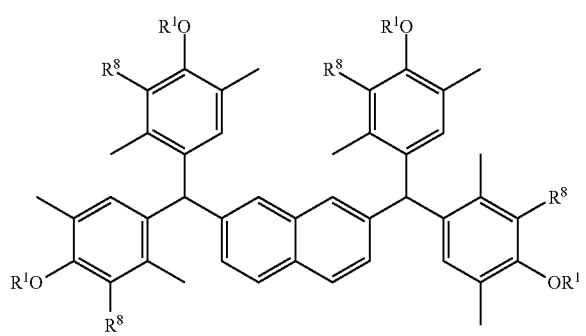

(16)

wherein $R^1$ and $R^8$ are the same as defined above. The compound of the above formula is excellent in the sensitivity, heat resistance, and resolution. The compound can be produced from relatively cheap phenols and can be easily separated and purified.

The compound of the formula 15 is also preferably represented by the following formulae 17-1 to 17-6:

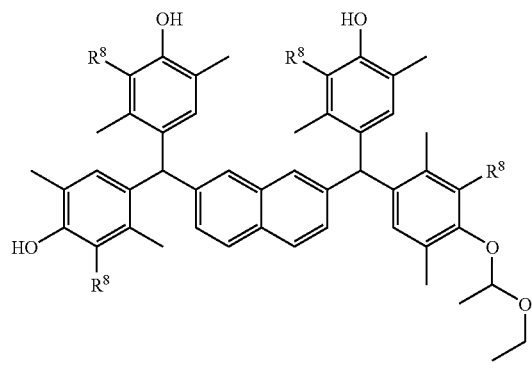
(17-1)
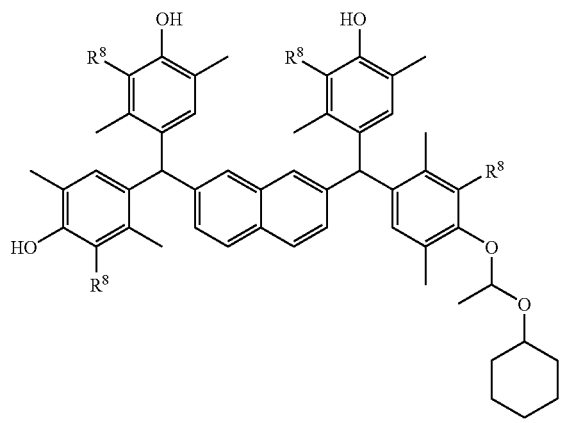
(17-2)
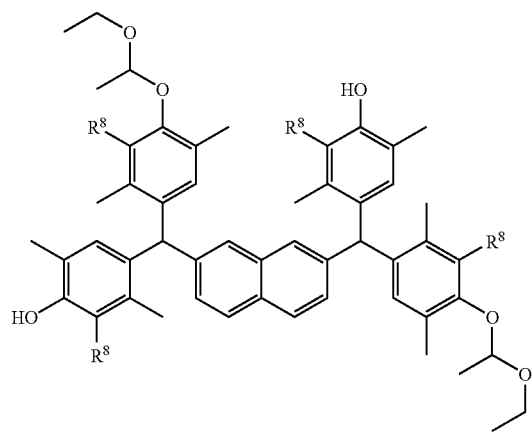
(17-3)
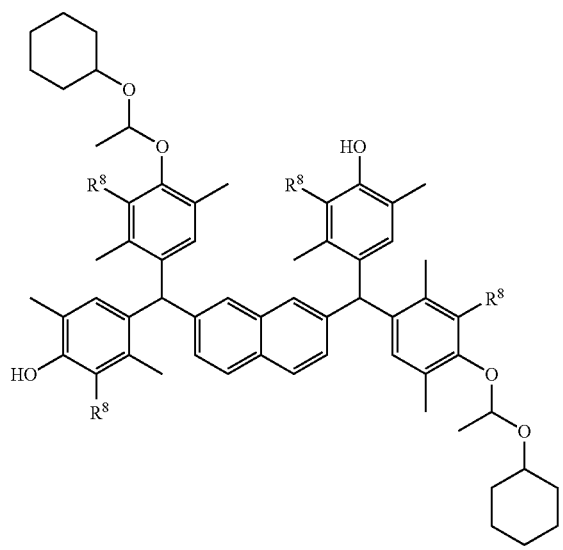
(17-4)
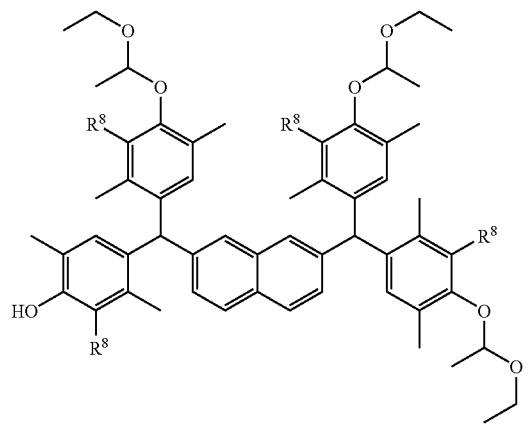
(17-5)
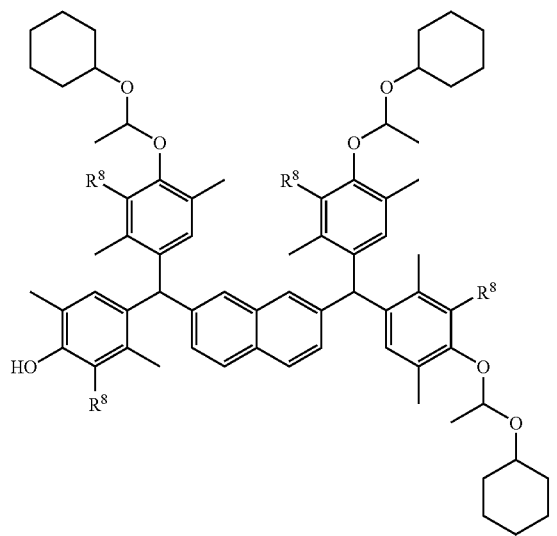
(17-6)

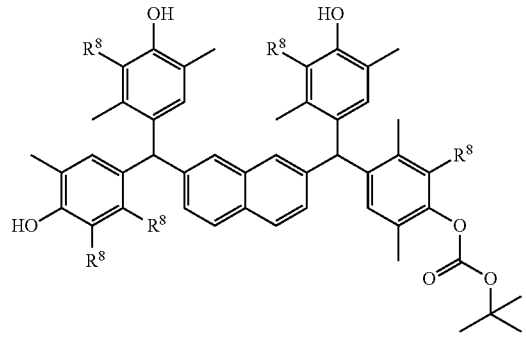

(17-7)

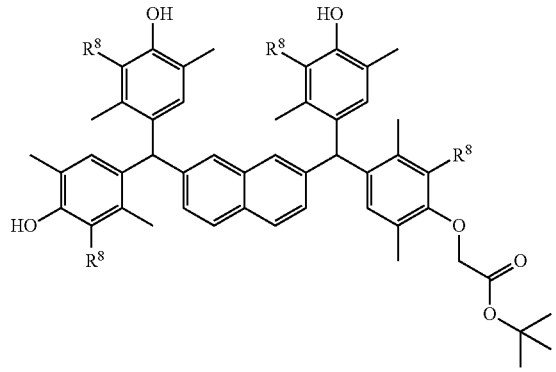

(17-8)

wherein $R^8$ is the same as defined above. The compounds of the above formulae are excellent in the resolution.

The compound of the formula 7-2 is preferably represented by the following formula 18-1:

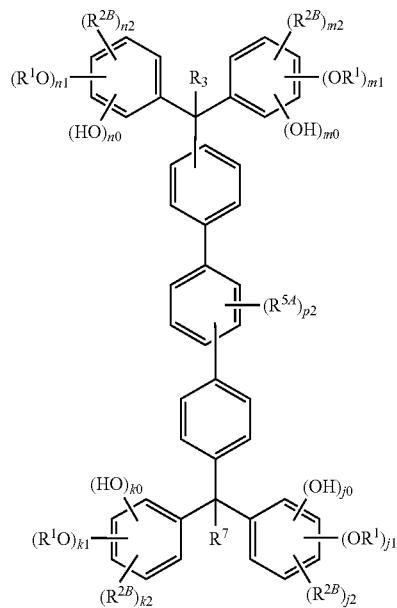

(18-1)

wherein $R^1$, $R^{2B}$, $R^3$, $R^{5A}$, $R^7$, k0, j0, m0, n0, k1, j1, m1, n1, k2, j2, m2, and n2 are the same as defined above; and p2 is an integer of 0 to 2. Two or more $R^1$, $R^{2B}$ or $R^{5A}$ may be the same or different, respectively.

The compound of the formula 7-2 is also preferably represented by the following formula 18-2:

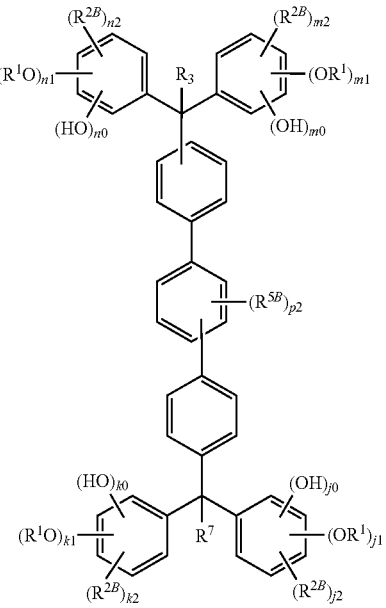

(18-2)

wherein $R^1$, $R^{2B}$, $R^3$, $R^{5B}$, $R^7$, p2, k0, j0, m0, n0, k1, j1, m1, n1, k2, j2, m2, and n2 are the same as defined above. Two or more $R^1$, $R^{2B}$ or $R^{5B}$ may be the same or different, respectively.

The compound of the formula 7-2 is also preferably represented by the following formula 19:

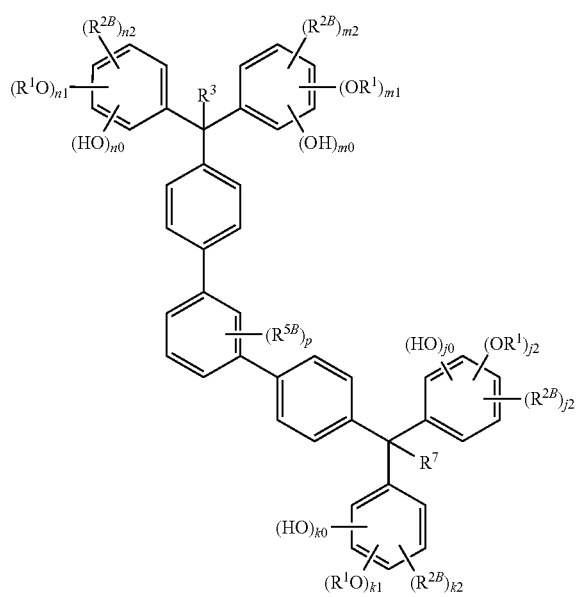

(19)

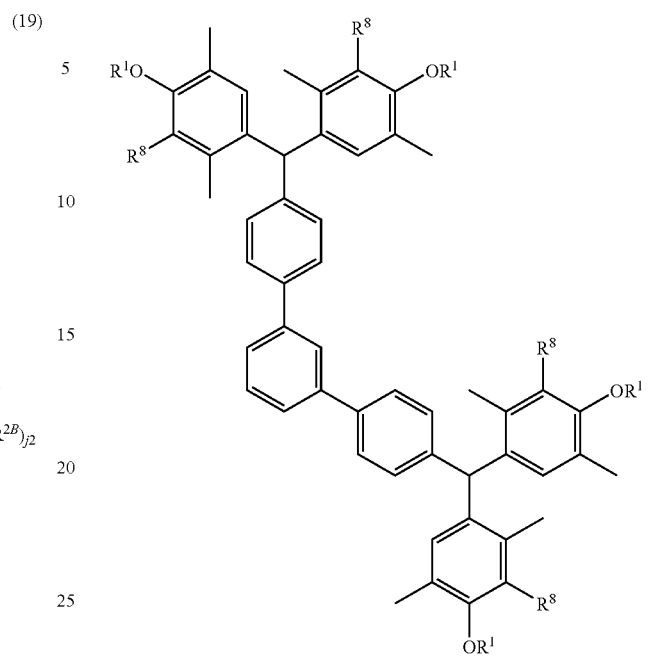

(20)

wherein $R^1$, $R^{2B}$, $R^3$, $R^{5B}$, $R^7$, p2, k0, j0, m0, n0, k1, j1, m1, n1, k2, j2, m2, and n2 are the same as defined above. The compound of the formula 19 is excellent in the sensitivity, heat resistance, and resolution. The compound can be produced from relatively cheap phenols and can be easily separated and purified.

The compound of the formula 19 is preferably represented by the following formula 20:

wherein $R^1$ and $R^8$ are the same as defined above. The compound of the above formula is excellent in the sensitivity, heat resistance, and resolution. The compound can be produced from relatively cheap phenols and can be easily separated and purified.

The compound of the formula 19 is also preferably represented by the following formulae 21-1 to 21-8:

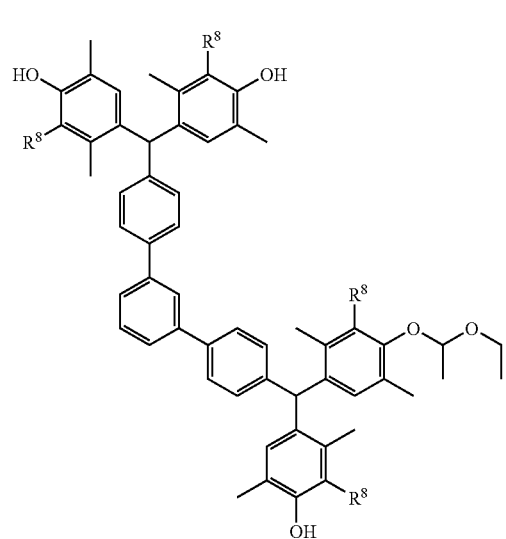

(21-1)

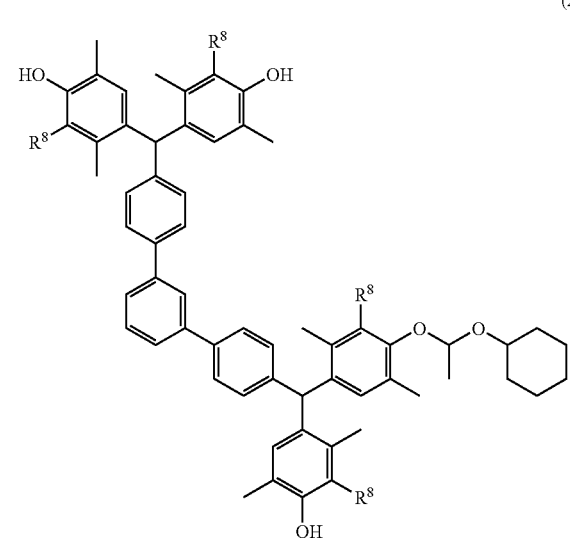

(21-2)

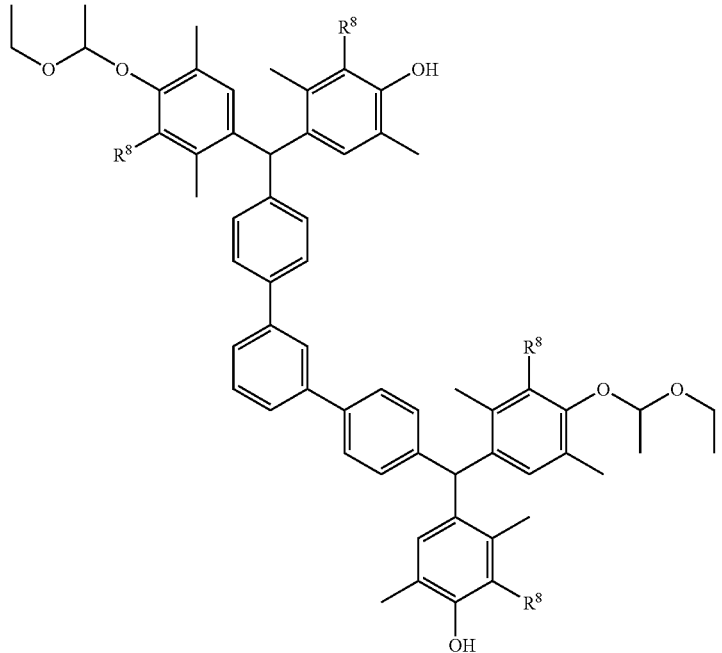
(21-3)
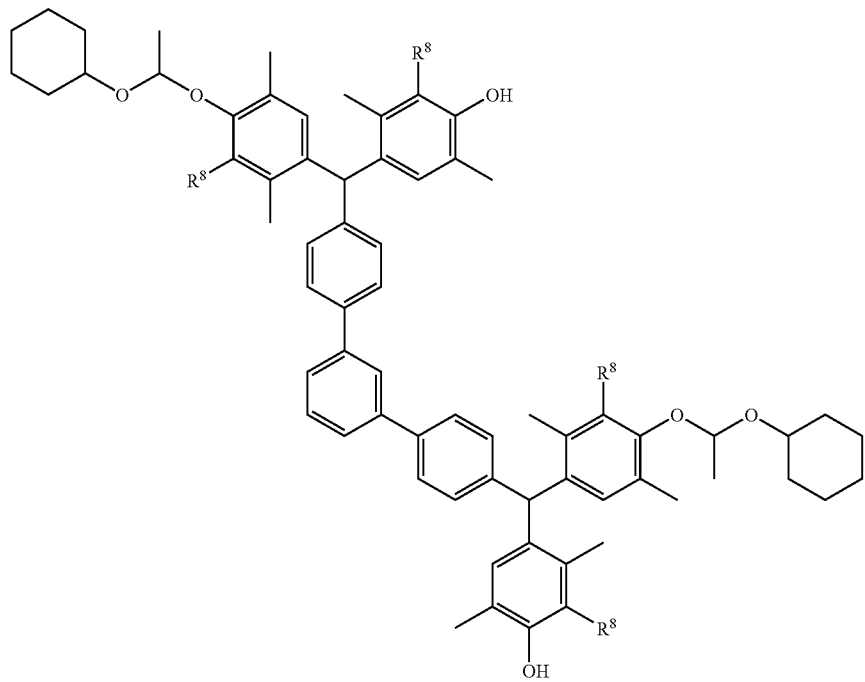
(21-4)

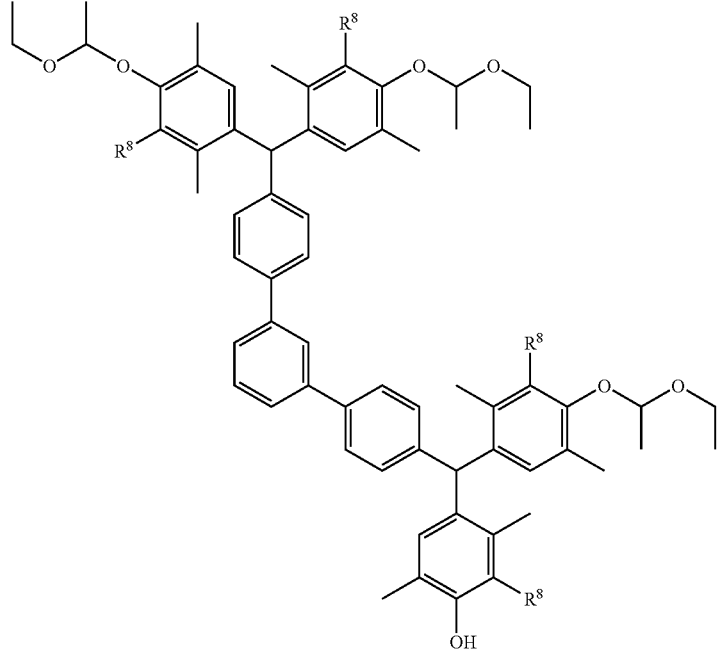
(21-5)
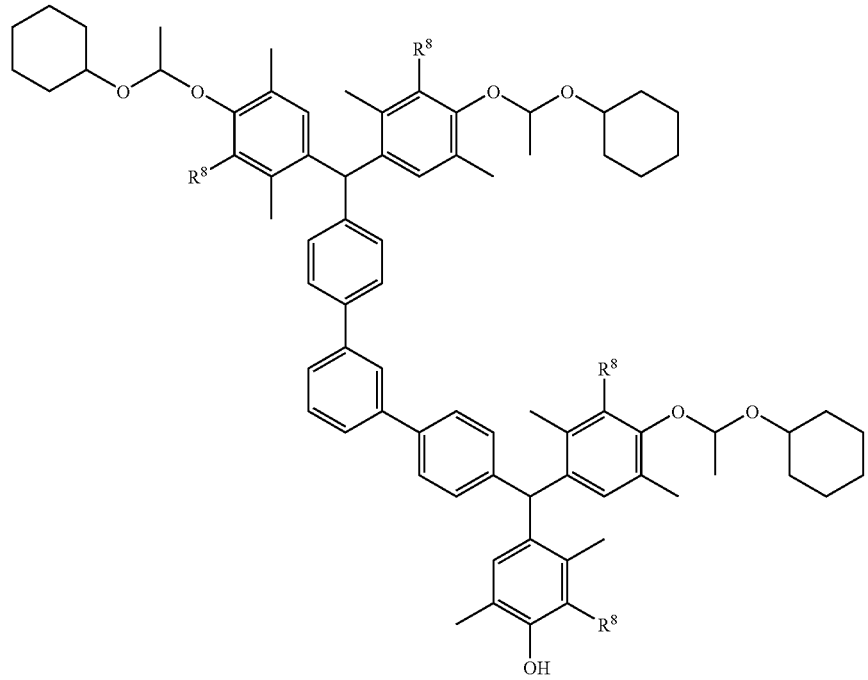
(21-6)

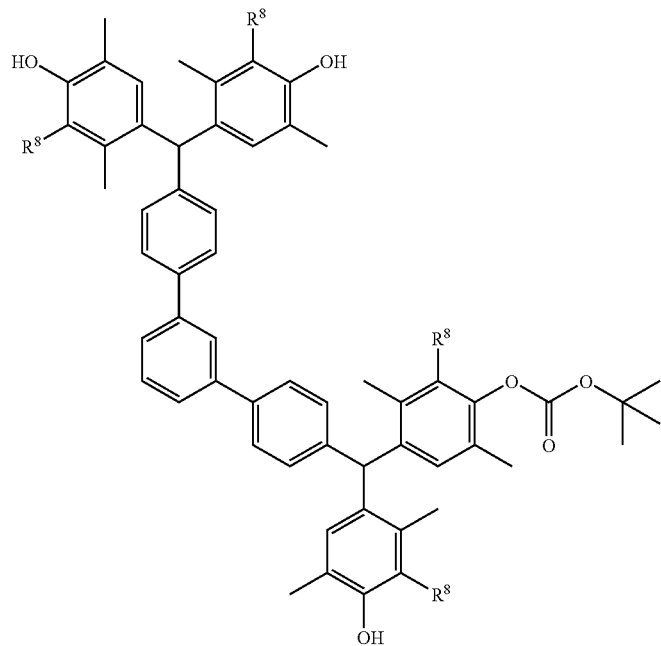
(21-7)
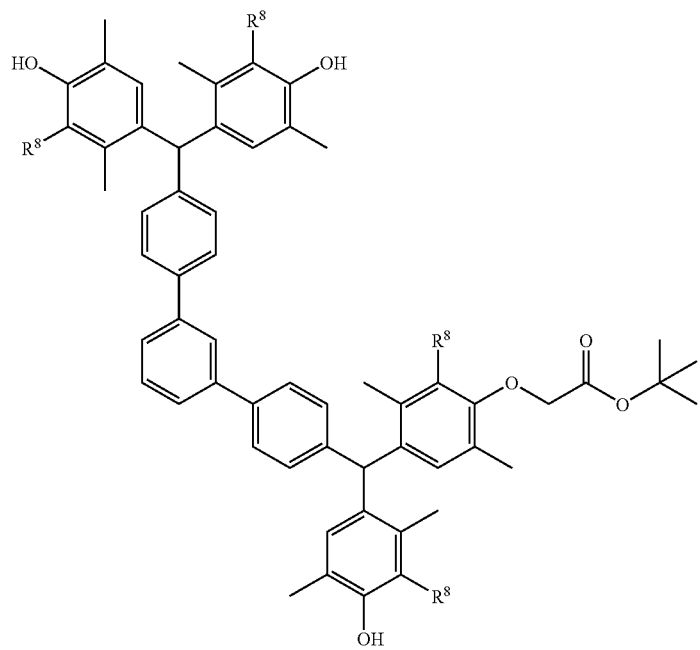
(21-8)

wherein $R^8$ is the same as defined above. The compounds of the above formulae are excellent in the resolution.

The compound of the formula 18-2 is preferably represented by the following formula 22:

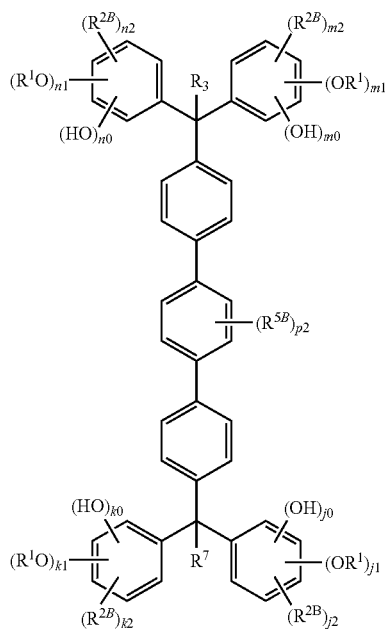
(22)

wherein $R^1$, $R^{2B}$, $R^3$, $R^{5B}$, $R^7$, p2, k0, j0, m0, n0, k1, j1, m1, n1, k2, j2, m2, and n2 are the same as defined above. The compound of the formula 22 is excellent in the sensitivity, heat resistance, and resolution. The compound can be produced from relatively cheap phenols and can be easily separated and purified.

The compound of the formula 22 is preferably represented by the following formula 23:

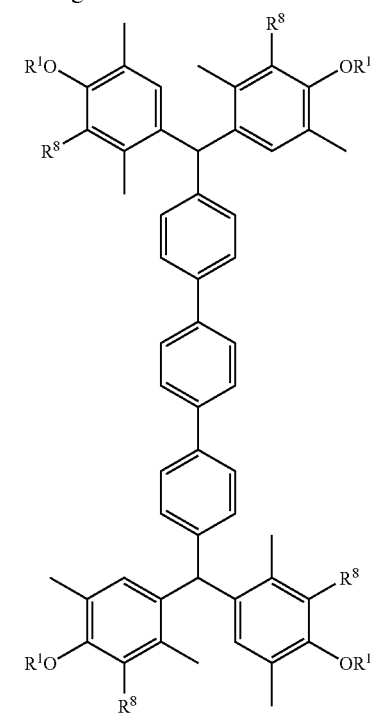
(23)

wherein $R^1$ and $R^8$ are the same as defined above. The compound of the above formula is excellent in the sensitivity, heat resistance, and resolution. The compound can be produced from relatively cheap phenols and can be easily separated and purified.

The compound of the formula 22 is preferably represented by the following formulae 24-1 to 24-8:

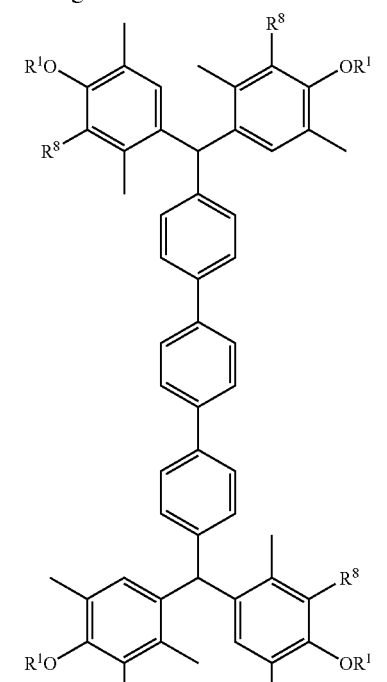
(24-1)

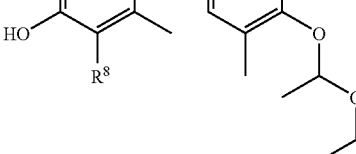
(24-2)

(24-3)
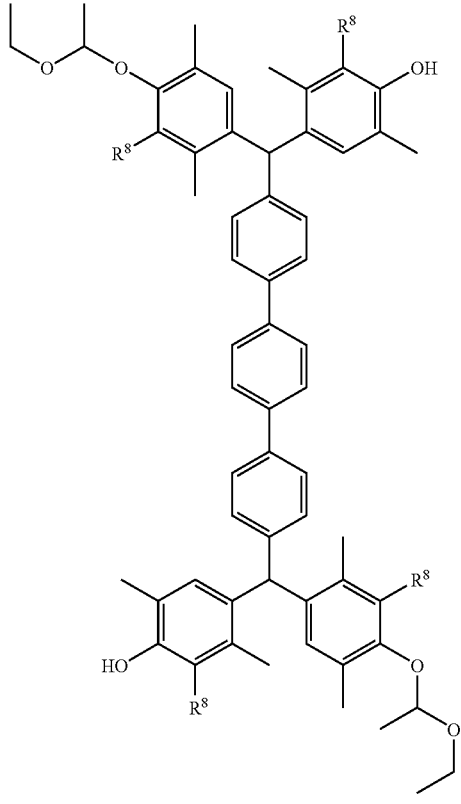
(24-4)
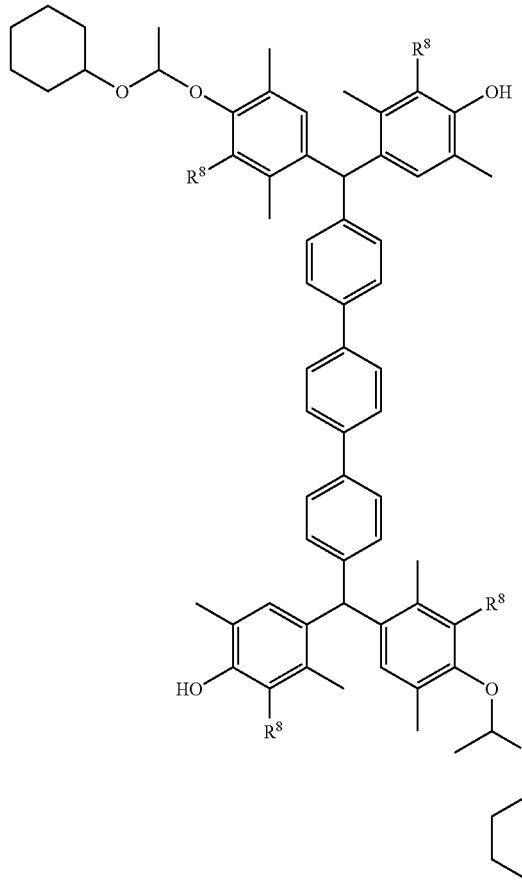
(24-5)
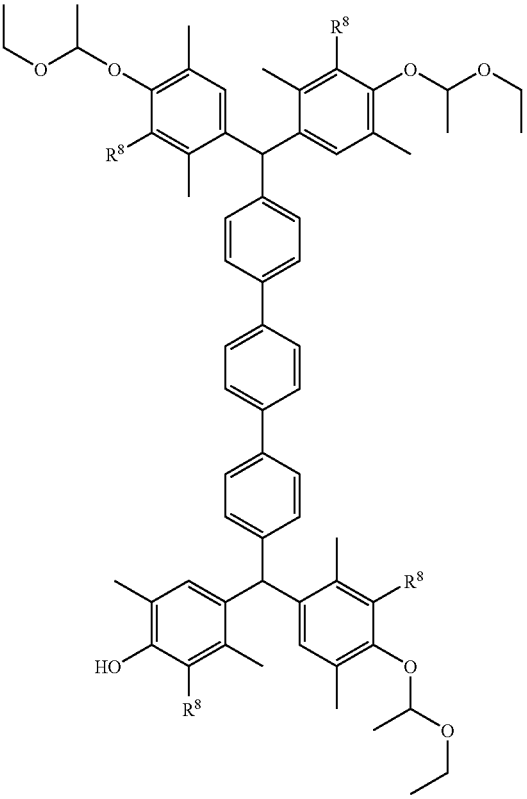
(24-6)
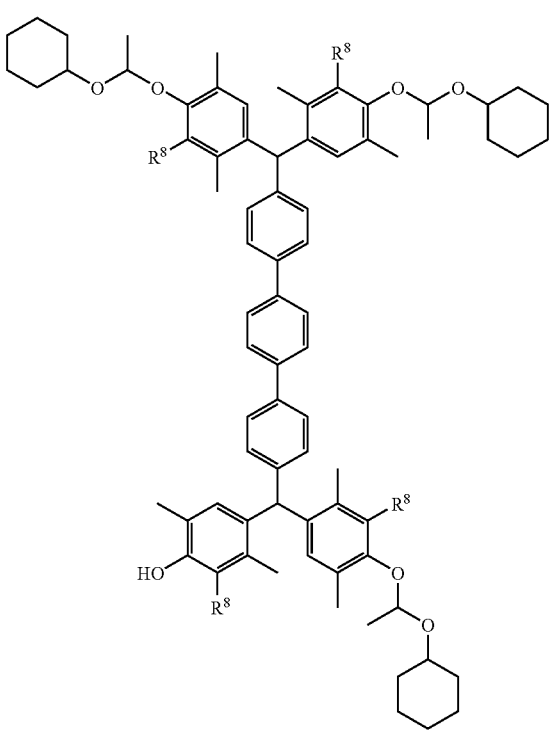

-continued
(24-7)
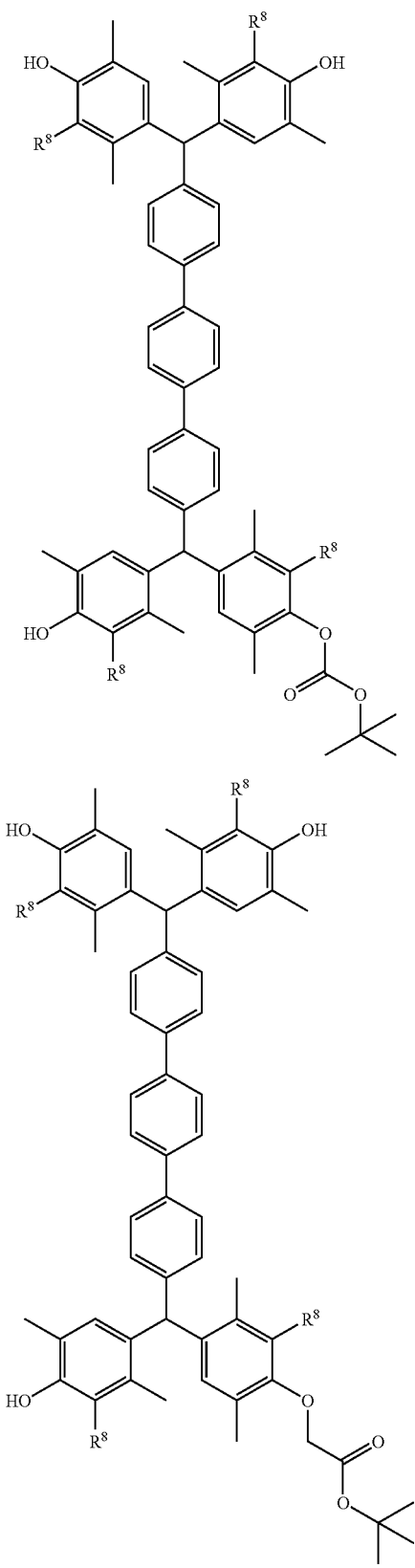
(24-8)
wherein R⁸ is the same as defined above. The compounds of the above formula are excellent in the resolution.
Preferred compounds of the formula 1 are listed below.
(25-1)
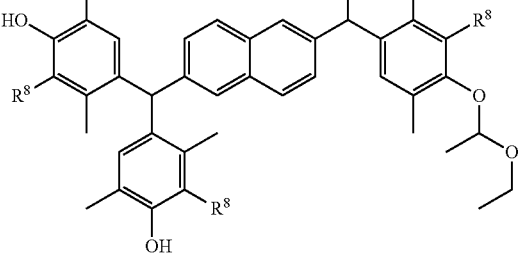
(25-2)
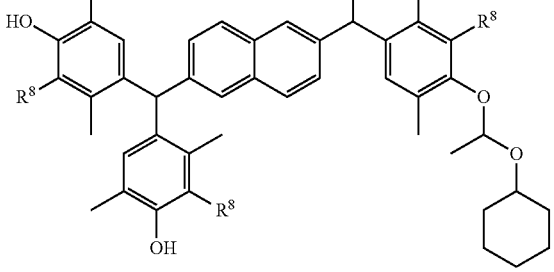
(12-7)
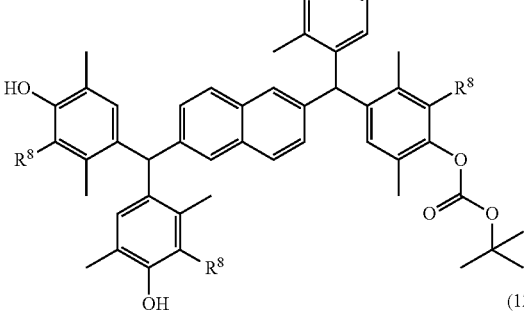
(12-8)
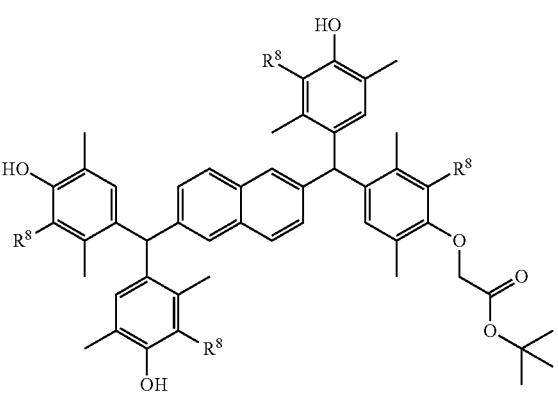

49
-continued
(25-3)
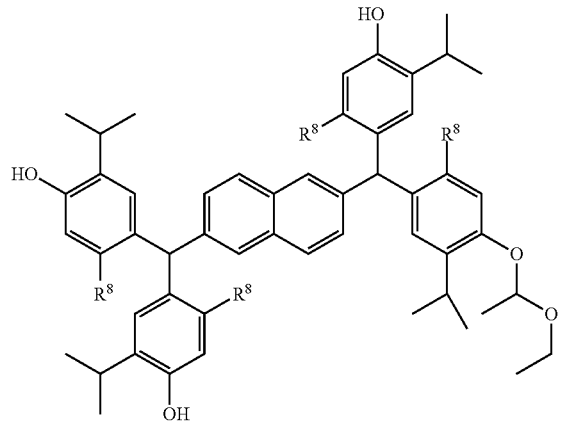
(25-4)
(25-5)
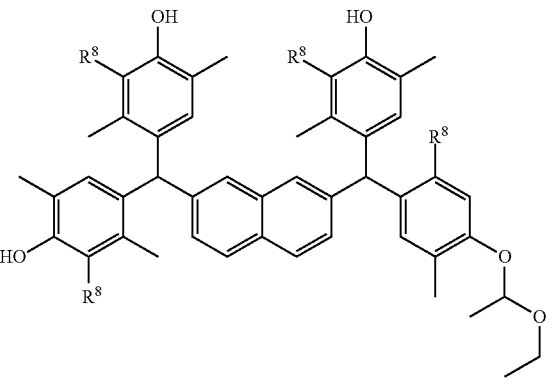
(25-6)
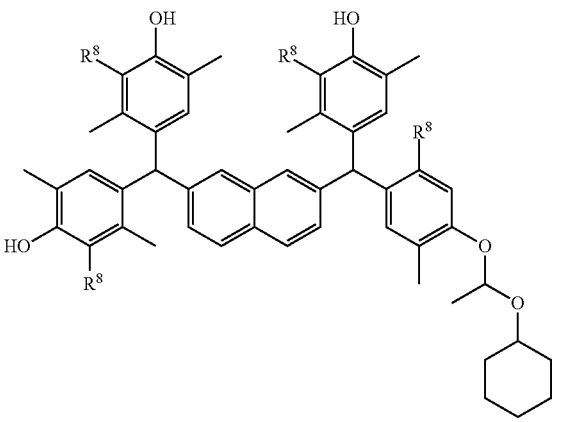
(14-7)
(17-7)
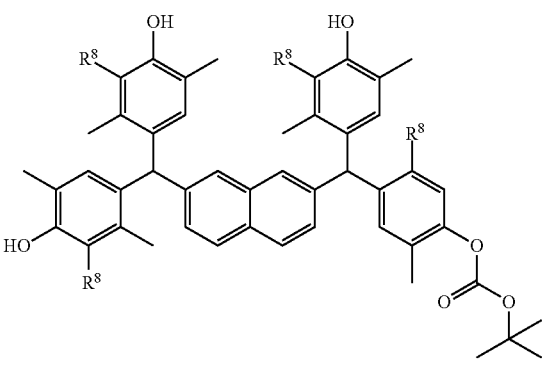
(14-8)
(17-8)
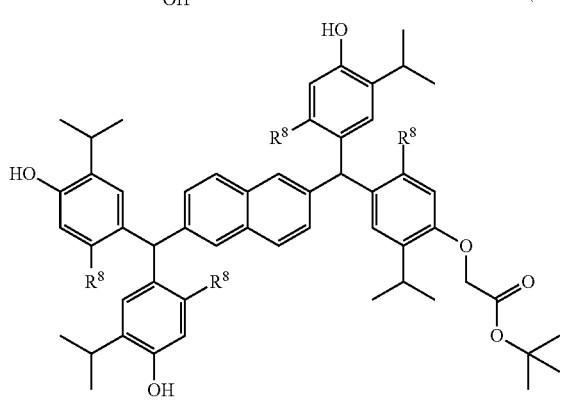

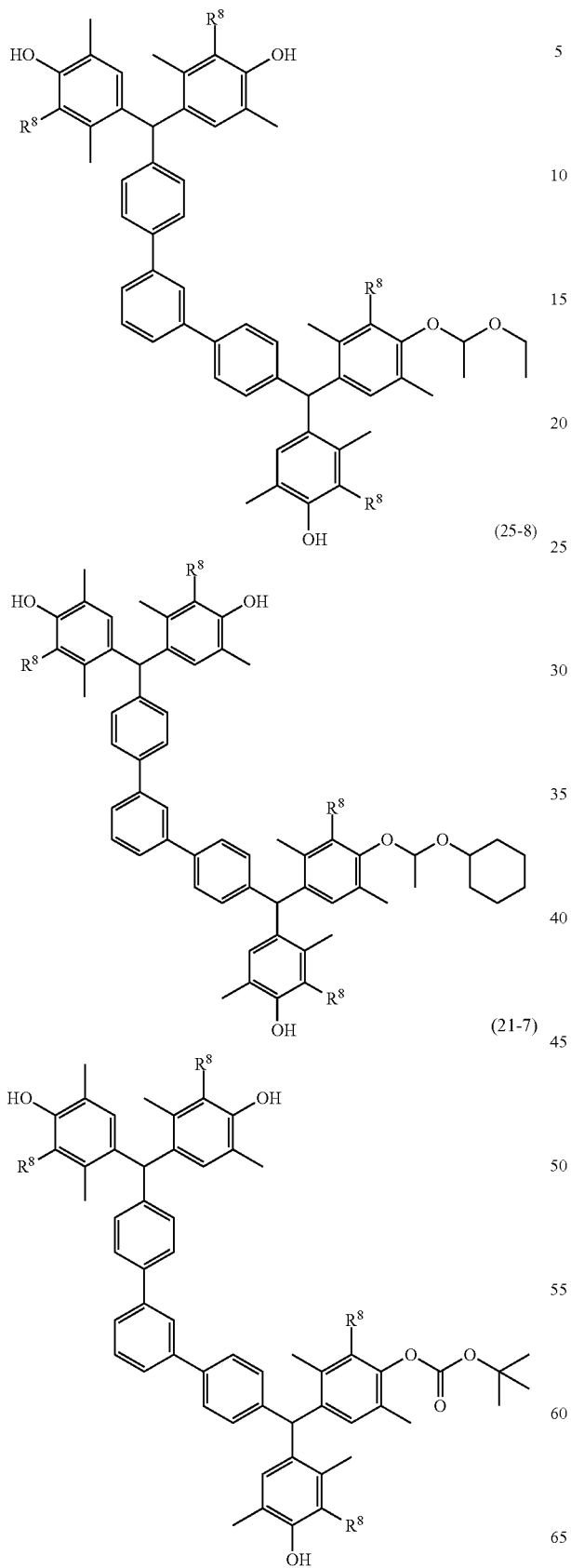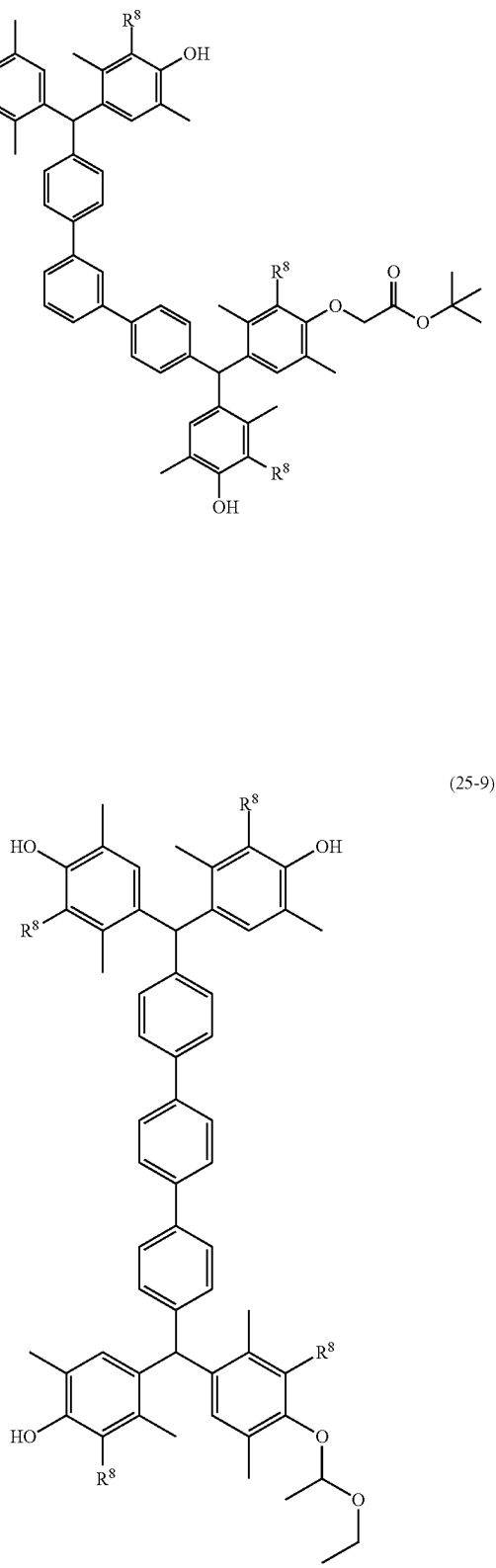

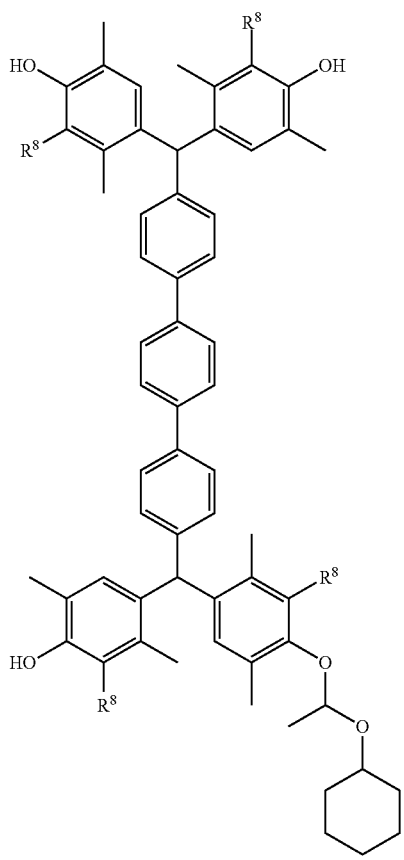
(25-10)
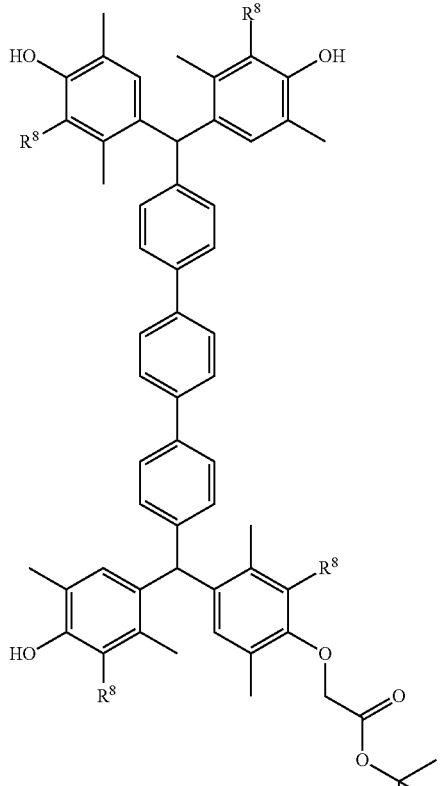
(24-8)
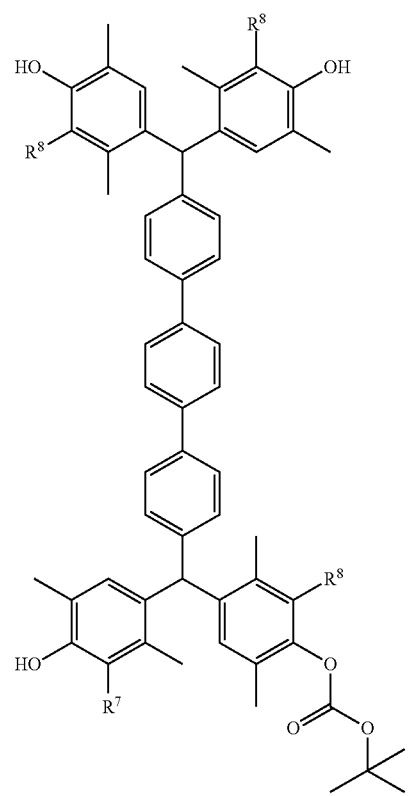
(24-7)
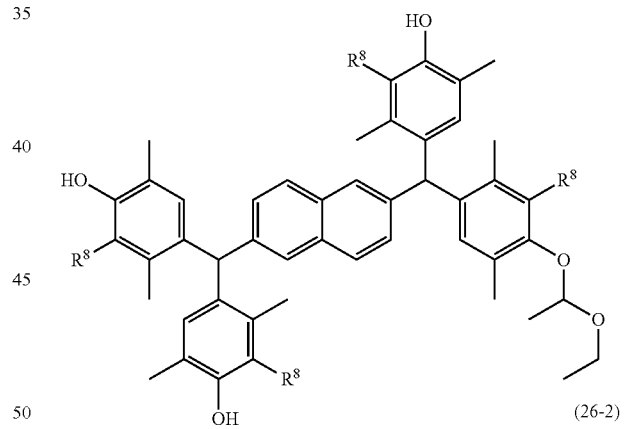
(26-1)
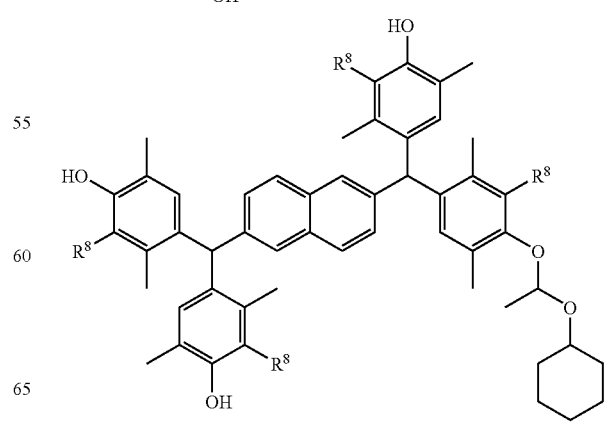
(26-2)

In the above formulae, $R^1$ and $R^8$ are the same as defined above.

In another preferred embodiment of the present invention, the compound B is represented by the following formula 28:

(28)

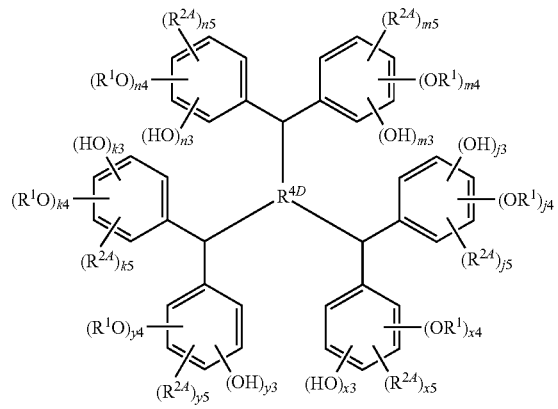

wherein $R^1$ and $R^{2A}$ are the same as defined above; $R^{4D}$ is a trivalent group having 6 to 20 carbon atoms which includes a benzene structure, naphthalene structure, terphenyl structure or phenanthrene structure; each of k3, j3, m3, n3, x3, and y3 is an integer of 0 to 3; each of k4, j4, m4, n4, x4, and y4 is an integer of 0 to 3; and each of k5, j5, m5, n5, x5, and y5 is an integer of 0 to 4, satisfying $1 \leq k3+k4+k5 \leq 5$, $1 \leq j3+j4+j5 \leq 5$, $1 \leq m3+m4+m5 \leq 5$, $1 \leq n3+n4+n5 \leq 5$, $1 \leq x3+x4+x5 \leq 5$, $1 \leq y3+y4+y5 \leq 5$, $1 \leq k4+j4+m4+n4+x4+y4 \leq 18$, $1 \leq k3+k4 \leq 3$, $1 \leq j3+j4 \leq 3$, $1 \leq m3+m4 \leq 3$, $1 \leq n3+n4 \leq 3$, $1 \leq x3+x4 \leq 3$, and $1 \leq y3+y4 \leq 3$.

The compound of the formula 28 is preferably represented by the following formula 29:

(29)

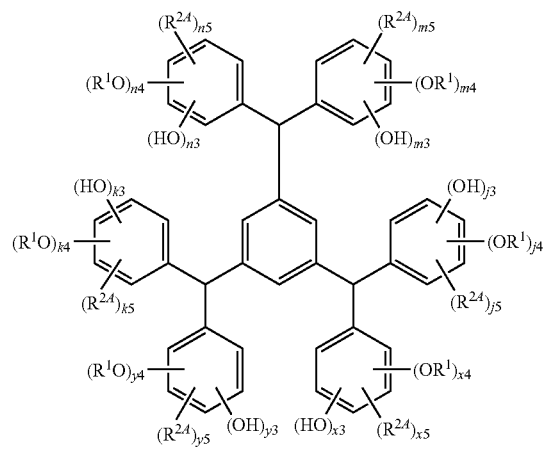

wherein $R^1$, $R^{2A}$, k3, j3, m3, n3, x3, y3, k4, j4, m4, n4, x4, y4, k5, j5, m5, n5, x5, and y5 are the same as defined above.

The compound of the formula 29 is preferably represented by the following formula 30-1:

(30-1)

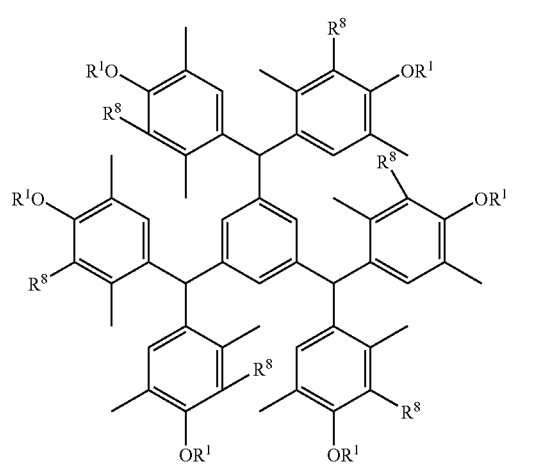

wherein $R^1$ and $R^8$ are the same as defined above.

The compound of the formula 29 is also preferably represented by the following formulae 31-1 to 31-3:

(31-1)

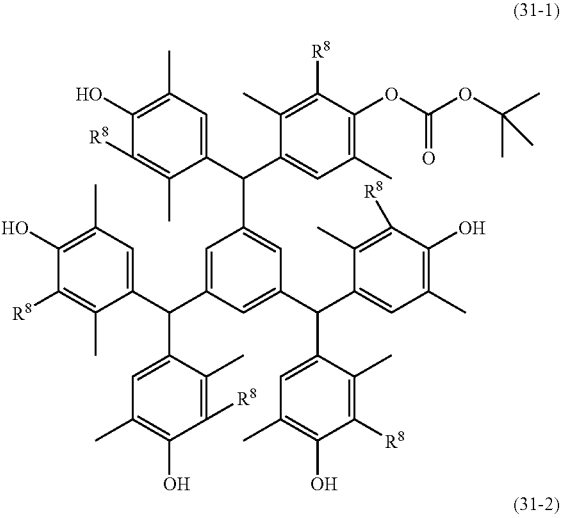

(31-2)

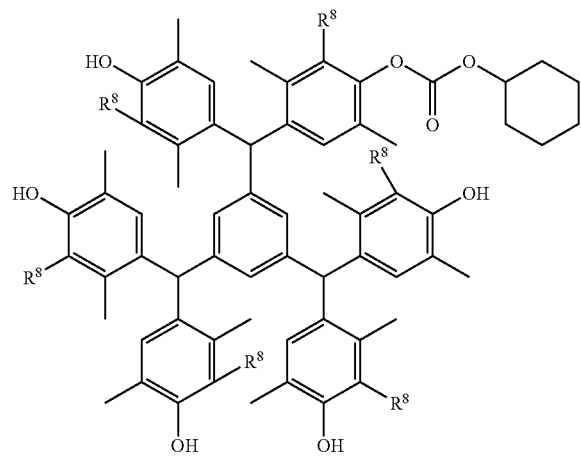

-continued (31-3)

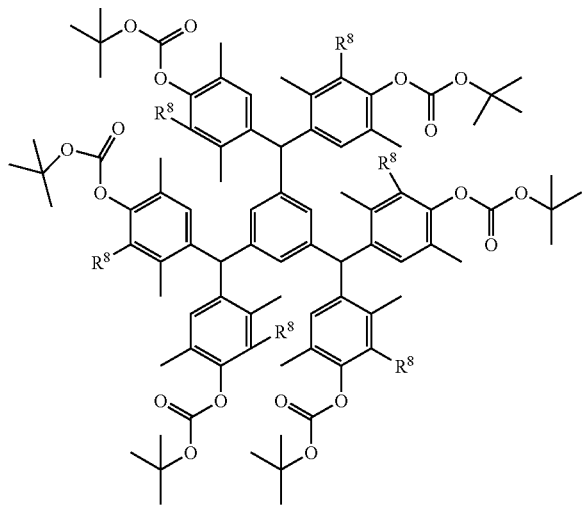

wherein $R^8$ is the same as defined above. The compounds of the formulae 30-1 and 31-1 to 31-3 are excellent in the sensitivity, heat resistance, and resolution. The compounds can be produced from relatively cheap phenols and can be easily separated and purified.

The production method of the compound B will be described below. One mole of the di- to tetrafunctional aromatic ketone or aromatic aldehyde and 1 mol to excess of the compound having a phenolic hydroxyl group are allowed to react in the presence of an acid catalyst (hydrochloric acid or sulfuric acid) and a co-catalyst (thioacetic acid or β-mercaptopropionic acid) for preventing the production of by-products at 60 to 150° C. for about 0.5 to 20 h. The amount of the aromatic ketone or aromatic aldehyde remaining unreacted is monitored by a known method such as a liquid chromatography, gas chromatography, thin layer chromatography, IR analysis, and $^1$H-NMR analysis. The reaction is taken as completed when the area of the peak attributable to the remaining amount is no longer reduced. After the reaction, the reaction production solution is added with methanol or isopropyl alcohol, heated to 60 to 80° C., and stirred for 0.5 to 2 h. Then, the reaction product is precipitated by adding an adequate amount of pure water. After cooling to room temperature, the precipitate is separated by filtration and dried, to obtain the polyphenol compound A. Alternatively, the polyphenol compound A is produced by converting the aromatic ketone or aromatic aldehyde into a dihalide using hydrogen chloride or halogen gas, and allowing the separated dihalide to react with the compound having 1 to 3 phenolic hydroxyl groups.

The acid-dissociating group is introduced into at least one phenolic hydroxyl group of the polyphenol compound A, for example, by the following method. Into a solution or suspension of the polyphenol compound A in an aprotic solvent such as acetone, tetrahydrofuran, and 1,3-dioxolane, a compound for introducing the acid-dissociating group such as tert-butoxycarbonyl group and tetrahydropyranyl group is added. Then the reaction is allowed to proceed in the presence of an amine catalyst such as triethylamine and dimethylaminopyridine or an acid catalyst such as pyridinium citrate under ordinary pressure at 20 to 60° C. for 6 to 24 h. The reaction product solution is added with distilled water to precipitate a white solid matter. The separated white solid matter is washed with distilled water and then dried, to obtain the compound B.

As the aprotic solvent, most preferred is 1,3-dioxolane, because the polyphenol compound A and the acid catalyst are well dissolved therein to increase the productivity.

The compound for introducing the acid-dissociating group is selected from, but not limited to, active carboxylic acid derivatives such as acid chloride, acid anhydride, and dicarbonate, alkyl halide, vinyl alkyl ether, and dihydropyran, each having the acid-dissociating group.

The acid-dissociating group referred to in the present invention is a characteristic group which generates an alkali-soluble group by dissociation in the presence of an acid. Examples of the alkali-soluble group include phenolic hydroxyl group, carboxyl group, sulfonic acid group, and hexafluoroisopropyl group, with the phenolic hydroxyl group and carboxyl group being preferred and the phenolic hydroxyl group being particularly preferred. To form a pattern with a high sensitivity and resolution, it is preferred that the acid-dissociating group is successively dissociated in the presence of acid.

Since a metal catalyst is not needed in the production of the compound B, the amount of residual metal in the compound B is small. To further reduce the amount of residual metal, the compound B may be purified, if necessary. If the basic compound used as the catalyst remains, the sensitivity of the radiation-sensitive composition is generally lowered. To reduce the remaining amount of the basic compound, the compound B may be purified. The purification may be carried out by any of known methods without limitation as long as the compound B is not unfavorably changed, for example, by a washing with water, a washing with an acidic aqueous solution, a treatment with an ion exchange resin, and a silica gel column chromatography. The purification is preferably conducted in a combination of two or more of the above methods. Taking the amount and kind of the metal and/or basic compound to be removed and the kind of the compound B to be purified into consideration, an optimum acidic aqueous solution, ion exchange resin or silica gel column chromatography are suitable selected. For example, hydrochloric acid, aqueous solution of nitric acid and aqueous solution of acetic acid, each having a concentration of 0.01 to 10 mol/L, are used as the acidic aqueous solution, and a cation exchange resin such as Amberlyst 15J-HG Dry manufactured by Organo Corporation is used as the ion exchange resin. The purified product may be dried by a known method such as, but not limited to, a vacuum drying and a hot-air drying under the conditions not changing the compound B.

The solubilizer C adequately increases the dissolving speed of the compound B in a developing solution such as alkalis by increasing the solubility, if the solubility is excessively low. Examples of the solubilizer C include low-molecular phenol compounds such as bisphenols and tris(hydroxyphenyl)methane. The solubilizers may be used singly or in combination of two or more. The blending amount of the solubilizer C varies depending upon the kind of the resist compound B to be used, and the solubilizer C is blended so that the total weight of the compound B and solubilizer C is 50 to 99.999% by weight, preferably 60 to 99% by weight, more preferably 70 to 99% by weight, and still more preferably 80 to 99% by weight, each based on the total weight of the solid component. The solubilizer C has an effect for increasing the solubility, but increases the line edge roughness (LER) in some cases. In such cases, it is rather preferred to avoid the use of the solubilizer C.

The solubilizer C is preferably a compound selected from the polyphenol compounds A described above. The polyphenol compound A is highly heat-resistant, highly amorphous, and highly compatible with the compound B, considering its low molecular weight, and provides a uniform resist film with a high resolution and a small LER. The polyphenol compound A for the solubilizer C is preferably the same as the polyphenol compound A which is used to produce the compound B, because the compatibility between the compound B and solubilizer C is more enhanced to enable the formation of a more uniform resist film with a high resolution and a small LER.

The solubilizer C is more preferably selected from the polyphenol compounds A represented by the following formulae 32-1 to 32-5 and 33-1:

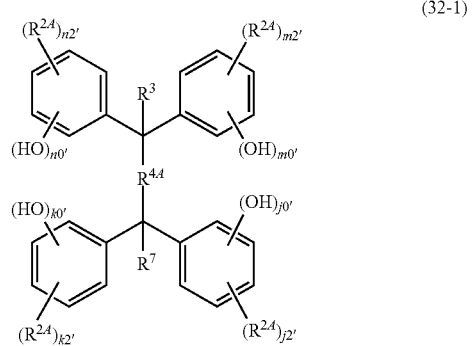

(32-1)

wherein $R^{2A}$, $R^3$, $R^{4A}$, and $R^7$ are the same as defined above, each of k0', j0', m0', and n0' is an integer of 1 to 3, and each of k2', j2', m2', and n2' is an integer of 0 to 4, satisfying $1 \leq k0'+k2' \leq 5$, $1 \leq j0'+j2' \leq 5$, $1 \leq m0'+m2' \leq 5$, and $1 \leq n0'+n2' \leq 5$;

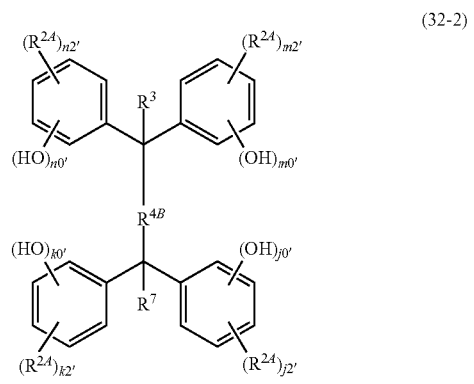

(32-2)

wherein $R^{2A}$, $R^3$, $R^{4B}$, $R^7$, k0', j0', m0', n0', k2', j2', m2', and n2' are the same as defined above, and two or more $R^{2A}$ may be the same or different;

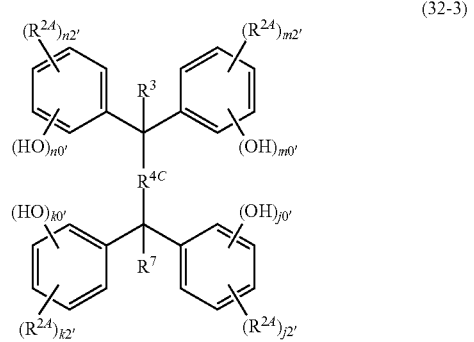

(32-3)

wherein $R^{2A}$, $R^3$, $R^{4C}$, $R^7$, k0', j0', m0', n0', k2', j2', m2', and n2' are the same as defined above, and two or more $R^{2A}$ may be the same or different;

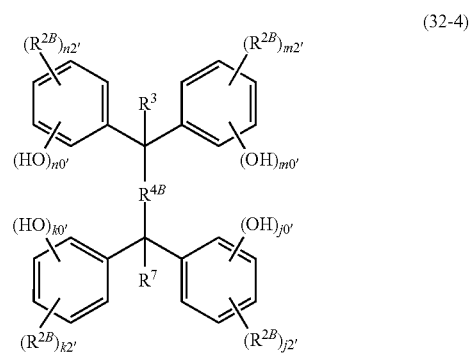

(32-4)

wherein $R^{2B}$, $R^3$, $R^{4B}$, $R^7$, k0', j0', m0', n0', k2', j2', m2', and n2' are the same as defined above, and two or more $R^{2B}$ may be the same or different;

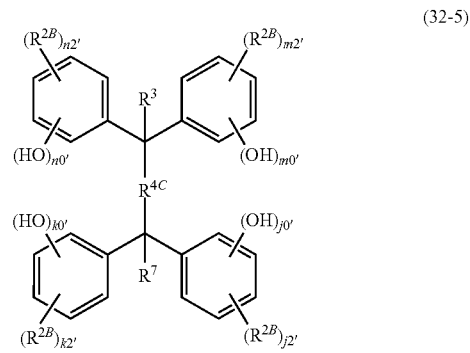

(32-5)

wherein $R^{2B}$, $R^3$, $R^{4C}$, $R^7$, k0', j0', m0', n0', k2', j2', m2', and n2' are the same as defined above, and two or more $R^{2B}$ may be the same or different; and

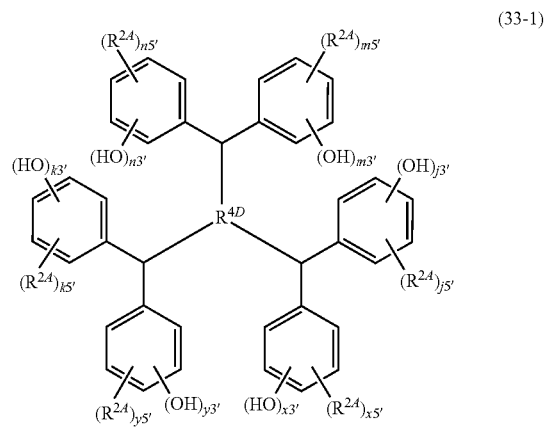

(33-1)

wherein $R^{2A}$ and $R^{4D}$ are the same as defined above, each of k3', j3', m3', n3', x3', and y3' is an integer of 1 to 3, and each of k5', j5', m5', n5', x5', and y5' is an integer of 0 to 4, satisfying $1 \leq k3'+k5' \leq 5$, $1 \leq j3'+j5' \leq 5$, $1 \leq m3'+m5' \leq 5$, $1 \leq n3'+n5' \leq 5$, $1 \leq x3'+x5' \leq 5$, and $1 \leq y3'+y5' \leq 5$.

More preferred for the solubilizer C are compounds represented by the following formulae 32-10, and 32-12 to 33-21:

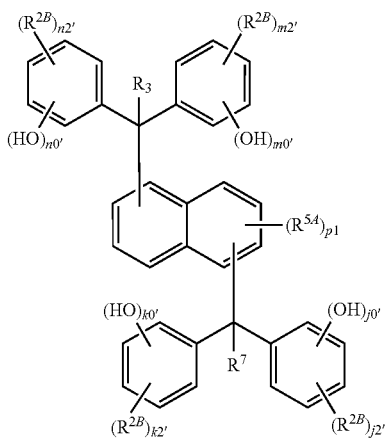

(32-10)

wherein $R^{2B}$, $R^3$, $R^{5A}$, $R^7$, p1, k0', j0', m0', n0', k2', j2', m2', and n2' are the same as defined above;

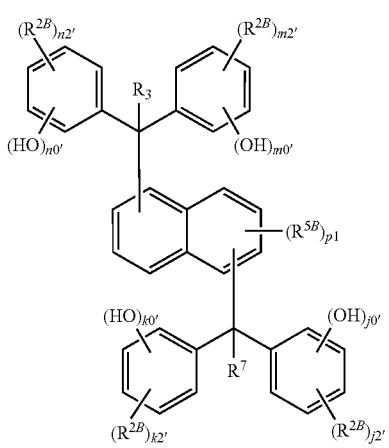

(32-12)

wherein $R^{2B}$, $R^3$, $R^{5B}$, $R^7$, p1, k0', j0', m0', n0', k2', j2', m2', and n2' are the same as defined above;

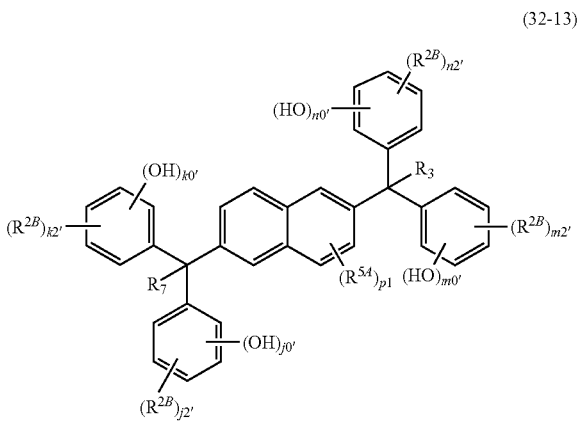

(32-13)

wherein $R^{2B}$, $R^3$, $R^{5A}$, $R^7$, p1, k0', j0', m0', n0', k2', j2', m2', and n2' are the same as defined above;

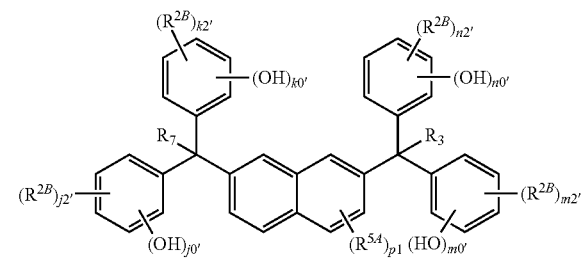

(32-14)

wherein $R^{2B}$, $R^3$, $R^{5A}$, $R^7$, p1, k0', j0', m0', n0', k2', j2', m2', and n2' are the same as defined above;

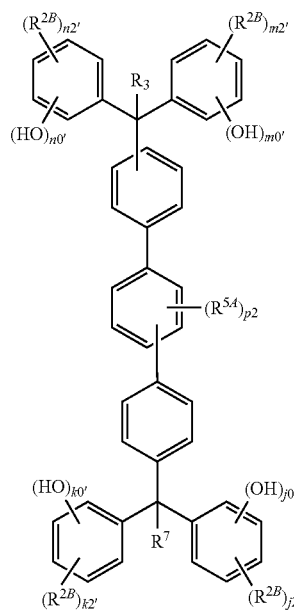

(32-15)

wherein $R^{2B}$, $R^3$, $R^{5A}$, $R^7$, k0', j0', m0', n0', k2', j2', m2', and n2' are the same as defined above, and p2 is an integer of 0 to 2;

(32-16)

wherein $R^{2B}$, $R^3$, $R^{5B}$, $R^7$, p2, k0', j0', m0', n0', k2', j2', m2', and n2' are the same as defined above;

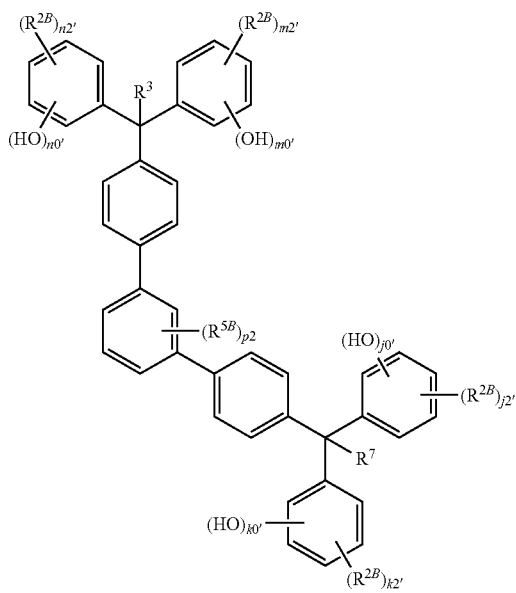

(32-17)

wherein $R^{2B}$, $R^3$, $R^{5B}$, $R^7$, p2, k0', j0', m0', n0', k2', j2', m2', and n2' are the same as defined above;

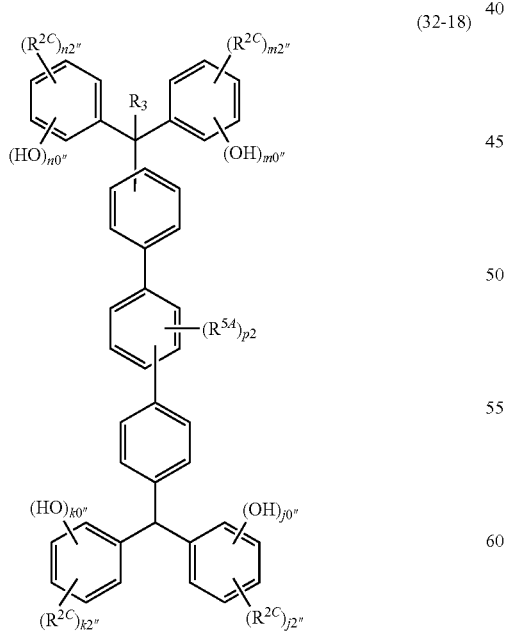

(32-18)

wherein $R^{5A}$ and p2 are the same as defined above, $R^{2C}$ is an alkyl group having 1 to 6 carbon atoms, each of k0", j0", m0", and n0" is an integer of 1 to 3, and each of k2", j2", m2", and n2" is an integer of 0 to 3, satisfying $1 \leq k0''+k2'' \leq 5$, $1 \leq j0''+j2'' \leq 5$, $1 \leq m0''+m2'' \leq 5$, and $1 \leq n0''+n2'' \leq 5$;

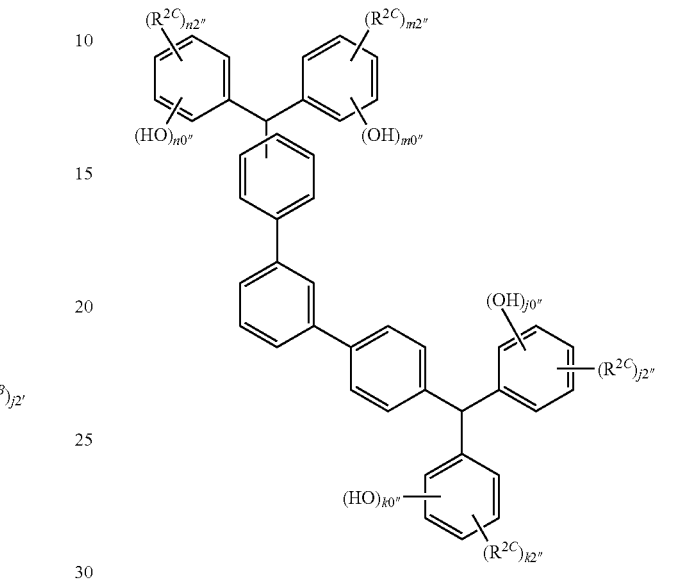

(32-19)

wherein $R^{2C}$, k0", j0", m0", n0", k2", j2", m2", and n2" are the same as defined above;

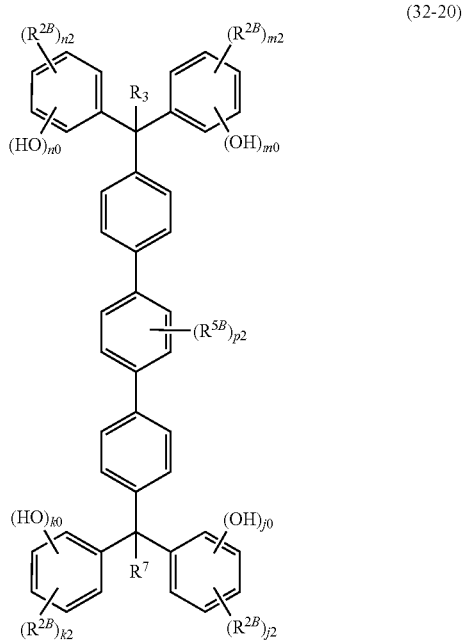

(32-20)

wherein $R^{2B}$, $R^3$, $R^{5B}$, $R^7$, p2, k0, j0, m0, n0, k2, j2, m2, and n2 are the same as defined above; and

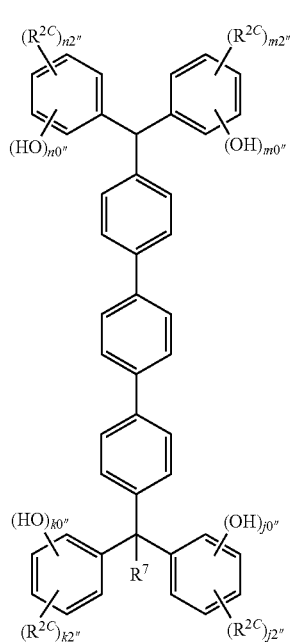
(32-21)
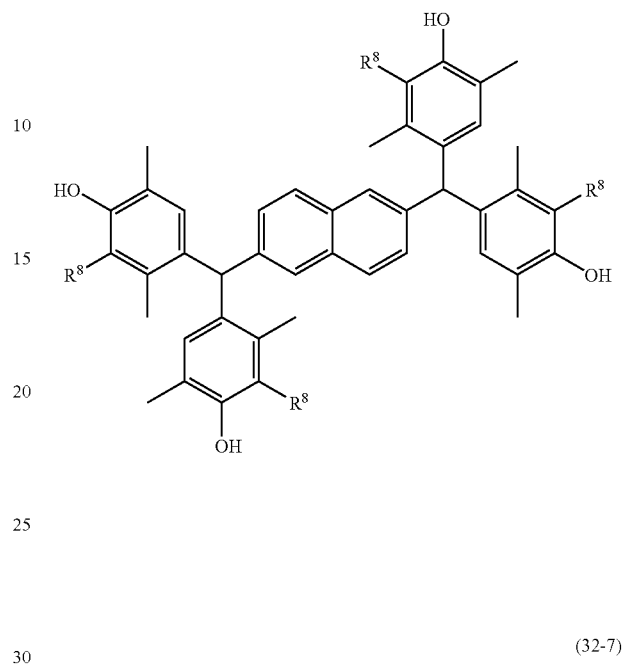
(32-6)
wherein $R^{2C}$, k0'', j0'', m0'', n0'', k2'', j2'', m2'', and n2'' are the same as defined above.
Other preferred compounds for the solubilizer C are represented by the following formulae 33-2, 32-6 to 32-10 and 33-3:
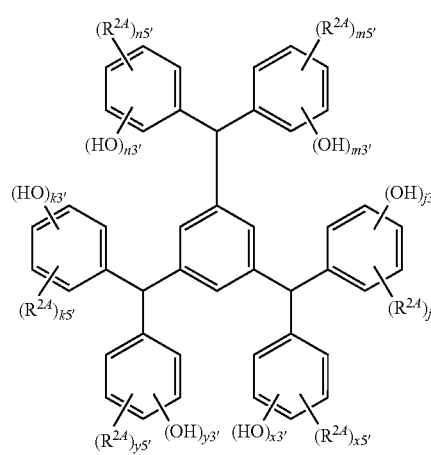
(33-2)
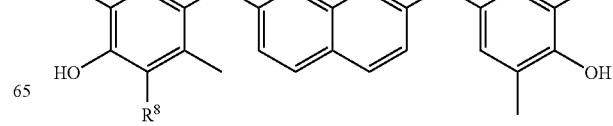
(32-7)
(32-8)
wherein $R^{2A}$, k3', j3', m3', n3', x3', y3', k5', j5', m5', n5', x5', and y5' are the same as defined above; and

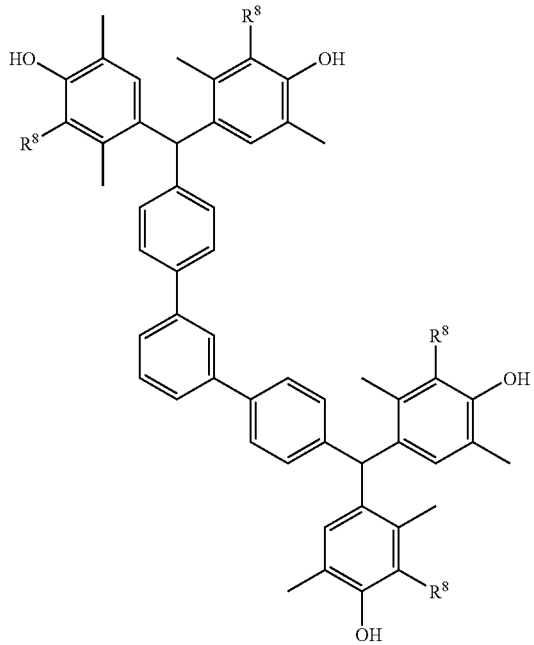
(32-9)

(32-10)

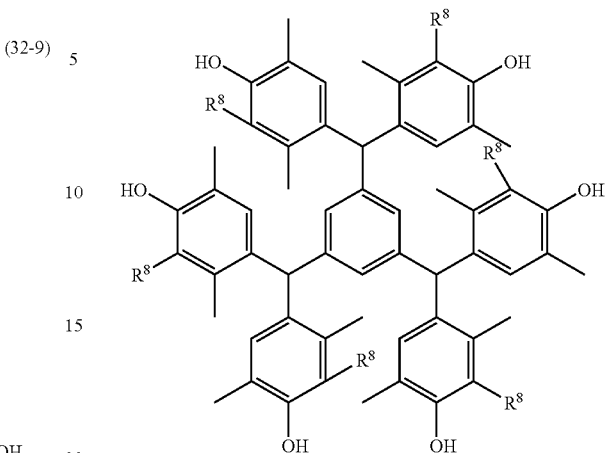
(33-3)

wherein $R^8$ are the same as defined above.

The blending ratio of the solid component and solvent is 1 to 80% by weight of the solid component to 20 to 99% by weight of the solvent, preferably 1 to 50% by weight of the solid component to 50 to 99% by weight of the solvent, more preferably 1 to 25% by weight of the solid component to 75 to 99% by weight of the solvent, and still more preferably 1 to 10% by weight of the solid component to 90 to 99% by weight of the solvent.

The solid component is preferably contains at least one acid generator which generates acid by the irradiation with radiation such as KrF excimer lasers, extreme ultraviolet rays, electron beams and X-rays. The amount of the acid generator to be used is preferably 0.001 to 50% by weight, more preferably 1 to 40% by weight, and still more preferably 3 to 30% by weight based on the total weight of the solid component (total of the compound B, solubilizer C, and optional components such as acid generator and acid-diffusion controller, the same being applied below). Within the above ranges, a pattern profile with a high sensitivity and small edge roughness is obtained. In the present invention, the acid can be generated by any method as long as the acid is suitably generated within the system. The use of excimer lasers in place of ultraviolet rays such as g-rays and i-rays enables a finer processing. If high-energy rays such as electron beams, extreme ultraviolet rays, X-rays and ion beams are used, the resist composition can be still more finely processed.

The amount of the acid generator to be used is particularly preferably 20 to 30% by weight of the total weight of the solid component. In the known resist compositions, it has been difficult to contain the acid generator as much as 20 to 30% by weight of the total weight of the solid component, and therefore, the amount has been generally 3 to 10% by weight. Since the radiation-sensitive composition of the present invention can contain the acid generator in an amount of 20 to 30% by weight, a high sensitivity and resolution which have been difficult to achieve by know resists can be obtained.

The acid generator is not particularly limited and is preferably at least one compound selected from the group consisting of the compounds represented by the following formulae 34 to 41.

In the formula 34:

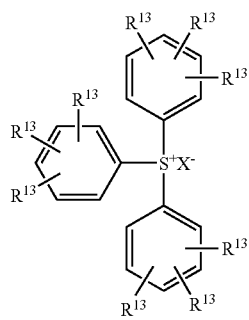

(34)

R$^{13}$ may be the same or different, and each independently a hydrogen atom, linear, branched or cyclic alkyl group, linear, branched or cyclic alkoxy group, hydroxyl group or halogen atom; and X$^-$ is a sulfonic acid ion having an alkyl group, aryl group, halogen-substituted alkyl group, or halogen-substituted aryl group or a halide ion.

The compound of the formula 34 is preferably at least one compound selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenyl-p-toluenesulfonate, diphenyl-2,4,6-trimethylphenylsulfonium 2-trifluoromethylbenzenesulfonate, diphenyl-2,4,6-trimethylphenylsulfonium 4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium p-toluenesulfonate, triphenylsulfonium 10-camphorsulfonate, diphenyl-4-hydroxyphenylsulfonium 10-camphorsulfonate, and cyclo(1,3-perfluoropropanedisulfon) imidate.

In the formula 35:

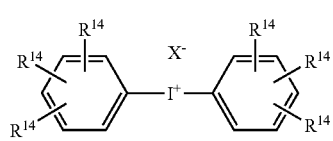

(35)

R$^{14}$ may be the same or different, and each independently a hydrogen atom, linear, branched or cyclic alkyl group, linear, branched or cyclic alkoxy group, hydroxyl group or halogen atom, and X$^-$ is the same as defined above.

The compound of the formula 35 is preferably at least one compound selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethylbenzenesulfonate, bis(4-t-butylphenyl)iodonium 4-trifluoromethylbenzenesulfonate, bis(4-t-butylphenyl)iodonium 2,4-difluorobenzenesulfonate, bis(4-t-butylphenyl)iodonium hexafluorobenzenesulfonate, bis(4-t-butylphenyl)iodonium 10-camphorsulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphorsulfonate, diphenyliodonium 2-trifluoromethylbenzenesulfonate, diphenyliodonium 4-trifluoromethylbenzenesulfonate, diphenyliodonium 2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium p-toluenesulfonate, di(4-trifluoromethylphenyl)iodonium benzenesulfonate, and di(4-trifluoromethylphenyl)iodonium 10-camphorsulfonate.

In the formula 36:

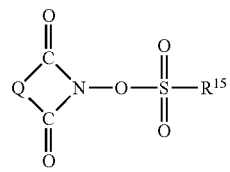

(36)

Q is an alkylene group, arylene group or alkoxylene group, and R$^{15}$ is an alkyl group, aryl group, halogen-substituted alkyl group or halogen-substituted aryl group.

The compound of the formula 36 is preferably at least one compound selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-ene-2,3-dicarboxylmide, N-(trifluoromethylsulfonyloxy)naphthylimide, N-(10-camphorsulfonyloxy)succinimide, N-(10-camphorsulfonyloxy)phthalimide, N-(10-camphorsulfonyloxy)diphenylmaleimide, N-(10-camphorsulfonyloxy)bicyclo[2.2.1]hept-5-ene-2,3-dicarboxylmide, N-(10-camphorsulfonyloxy)naphthylimide, N-(n-octanesulfonyloxy)bicyclo[2.2-1]hept-5-ene-2,3-dicarboxylmide, N-(n-octanesulfonyloxy)naphthylimide, N-(p-toluenesulfonyloxy)bicyclo[2.2.1]hept-5-ene-2,3-dicarboxylmide, N-(p-toluenesulfonyloxy)naphthylimide, N-(2-trifluoromethylbenzenesulfonyloxy)bicyclo[2.2.1]hept-5-ene-2,3-dicarboxylmide, N-(2-trifluoromethylbenzenesulfonyloxy)naphthylimide, N-(4-trifluoromethylbenzenesulfonyloxy)bicyclo[2.2.1]hept-5-ene-2,3-dicarboxylmide, N-(4-trifluoromethylbenzenesulfonyloxy)naphthylimide, N-(perfluorobenzenesulfonyloxy)bicyclo[2.2.1]hept-5-ene-2,3-dicarboxylmide, N-(perfluorobenzenesulfonyloxy)naphthylimide, N-(1-naphthalenesulfonyloxy)bicyclo[2.2.1]

hept-5-ene-2,3-dicarboxylmide, N-(1-naphthalenesulfonyloxy)naphthylimide, N-(nonafluoro-n-butanesulfonyloxy)bicyclo[2.2.1]hept-5-ene-2,3-dicarboxylmide, N-(nonafluoro-n-butanesulfonyloxy)naphthylimide, N-(perfluoro-n-octanesulfonyloxy)bicyclo[2.2.1]hept-5-ene-2,3-dicarboxylmide, and N-(perfluoro-n-octanesulfonyloxy)naphthylimide.

In the formula 37:

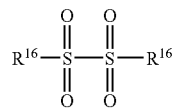
(37)

$R^{16}$ may be the same or different, and each independently an optionally substituted linear, branched or cyclic alkyl group, optionally substituted aryl group, optionally substituted heteroaryl group or optionally substituted aralkyl group.

The compound of the formula 37 is preferably at least one compound selected from the group consisting of diphenyl disulfone, di(4-methylphenyl)disulfone, dinaphthyl disulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone, and di(4-trifluoromethylphenyl)disulfone.

In the formula 38:

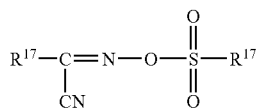
(38)

$R^{17}$ may be the same or different, and each independently an optionally substituted linear, branched or cyclic alkyl group, optionally substituted aryl group, optionally substituted heteroaryl group or optionally substituted aralkyl group.

The compound of the formula 38 is at least one compound selected from the group consisting of α-(methylsulfonyloxyimino)phenylacetonitrile, α-(methylsulfonyloxyimino)-4-methoxyphenylacetonitrile, α-(trifluoromethylsulfonyloxyimino)phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

In the formula 39:

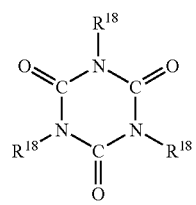
(39)

$R^{18}$ may be the same or different, and each independently a haloalkyl group having one or more chlorine atoms and one or more bromine atoms. The haloalkyl group preferably has 1 to 5 carbon atoms.

In the formulae 40 and 41:

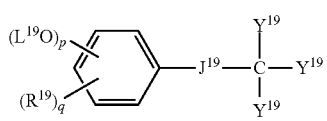
(40)

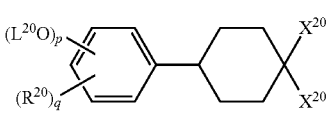
(41)

$R^{19}$ and $R^{20}$ are each independently an alkyl group having 1 to 3-carbon atoms such as methyl group, ethyl group, n-propyl group, and isopropyl group; cycloalkyl group such as cyclopentyl group and cyclohexyl group; alkoxy group having 1 to 3 carbon atoms such as methoxy group, ethoxy group, and propoxy group; or aryl group such as phenyl group, tolyl group, and naphthyl group, preferably aryl group having 6 to 10 carbon atoms. $L^{19}$ and $L^{20}$ are each independently an organic group having a 1,2-naphthoquinonediazido group, preferred examples thereof including 1,2-quinonediazidosulfonyl groups such as 1,2-naphthoquinonediazido-4-sulfonyl group, 1,2-naphthoquinonediazido-5-sulfonyl group, and 1,2-naphthoquinonediazido-6-sulfonyl group, with 1,2-naphthoquinonediazido-4-sulfonyl group and 1,2-naphthoquinonediazido-5-sulfonyl group being particularly preferred. Subscript p is an integer of 1 to 3, and q is an integer of 0 to 4, satisfying $1 \leq p+q \leq 5$. $J^{19}$ is a single bond, polymethylene group having 1 to 4 carbon atoms, cycloalkylene group, phenylene group, group represented by the following formula 42:

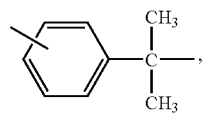
(42)

carbonyl group, ester group, amide group, or ether group; $Y^{19}$ is a hydrogen atom, alkyl group or aryl group; and each $X^{20}$ is independently a group represented by the following formula 43:

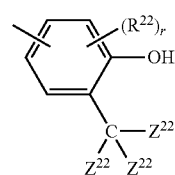
(43)

wherein each $Z^{22}$ is independently an alkyl group, cycloalkyl group or aryl group, $R^{22}$ is an alkyl group, cycloalkyl group or alkoxy group, and r is an integer of 0 to 3.

Examples of other acid generators include bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl) propane, 1,4-bis(phenylsulfonylazomethylsulfonyl)butane, 1,6-bis(phenylsulfonylazomethylsulfonyl)hexane, and 1,10-bis(cyclohexylsulfonylazomethylsulfonyl)decane; and halotriazine derivatives such as 2-(4-methoxyphenyl)-4,6-(bis-trichloromethyl)-1,3,5-triazine, 2-(4-methoxynaphthyl)-4,6-(bistrichloromethyl)-1,3,5-triazine, tris(2,3-dibromopropyl)-1,3,5-triazine, and tris(2,3-dibromopropyl)isocyanurate.

Preferred acid generators are those having an aromatic ring, and more preferred is triphenylsulfonium p-toluenesulfonate. Using the acid generator, LER can be reduced. This may be because of a good dispersibility of the acid generator in the compound B.

The radiation-sensitive composition may contain an acid-diffusion controller which prevents the undesirable chemical reactions in unexposed areas by controlling the diffusion of the acid, which is generated from the acid generator upon the irradiation of radiation, throughout the resist film. Using such an acid-diffusion controller, the storage stability of the radiation-sensitive composition is improved. In addition, the resolution is improved and the change of line width of resist patterns due to the difference in the time delay before and after the irradiation of electron beams is prevented, to ensure the stable production. Examples of the acid-diffusion controller include basic compounds decomposable by the irradiation of electron beams such as nitrogen-containing basic compounds, basic sulfonium compounds, and basic iodonium compounds. These acid-diffusion controllers may be used alone or in combination of two or more.

Preferred acid-diffusion controllers are those having an aromatic ring, with triphenylimidazole being more preferred. Using the acid-diffusion controller, the LER can be reduced, which may be because of the good dispersibility between the compound B and the acid generator.

The blending amount of the acid-diffusion controller is preferably 0 to 10% by weight, more preferably 0.001 to 5% by weight, and still more preferably 0.001 to 3% by weight, each based on the total weight of the solid component. Within the above ranges, the lowering of the resolution and the deterioration of the pattern profiles and dimension accuracy are prevented. In addition, the unfavorable change of the upper profile of pattern is prevented even if the time delay between the irradiation of radiation and the post-irradiation heating is prolonged. If being 10% by weight or less, the reduction of the sensitivity and developability of unexposed area can be prevented.

In the radiation-sensitive composition, the total number of the acid-dissociating groups in both the compound B and solubilizer C is preferably 5 to 95%, more preferably 5 to 50%, and still more preferably 5 to 25%, each based on the total number of the phenolic hydroxyl groups in both the compound B and solubilizer C. Within the above ranges, the sensitivity, resolution, adhesion, and film-forming properties are good.

The amount of the solubilizer C is preferably 80% by weight or less, more preferably 60% by weight or less, still more preferably 30% by weight or less, and particularly preferably zero, each based on the total weight of the compound B and solubilizer C. Within the above ranges, the line edge roughness is reduced.

A particularly preferred radiation-sensitive composition contains 1 to 25% by weight of the solid component and 75 to 99% by weight of the solvent, with the amount of the compound B being 80 to 99% by weight of the solid component. With such radiation-sensitive composition, a high resolution and a small line edge roughness are achieved.

The amount of residual metal in the compound B is preferably less than 10 ppm, more preferably less than 1 ppm, and still more preferably less than 100 ppb. Within the above ranges, the contamination of semiconductor devices can be prevented and the radiation-sensitive composition acquires a high sensitivity. As mentioned above, the compound B is produced using a non-metallic catalyst. Therefore, the amount of residual metal necessarily falls within the above ranges. If needed, the compound B may be purified by a silica gel column chromatography, etc.

In addition to the above additives, the radiation-sensitive composition may contain a resin which is insoluble to water but soluble to an aqueous solution of alkali or an alkali-developable resin which is insoluble to water but becomes soluble to an aqueous solution of alkali by the action of acid as long as the effect of the present invention is adversely affected. Examples of such resins include phenol resins which may be introduced with an acid-dissociating group; novolak resins which may be introduce with an acid-dissociating group; hydrogenated novolak resins which may be introduced with an acid-dissociating group; o-polyhydroxystyrene, m-polyhydroxystyrene, p-polyhydroxystyrene, and copolymers thereof, which may be introduced with an acid-dissociating group; alkyl-substituted polyhydroxystyrenes which may be introduced with an acid-dissociating group; polyhydroxystyrene which may be introduced with an acid-dissociating group; partially o-alkylated polyhydroxystyrene which may be introduced with an acid-dissociating group; styrene-hydroxystyrene copolymer which may be introduced with an acid-dissociating group; α-methylstyrene-hydroxystyrene copolymer which may be introduced with an acid-dissociating group; polyalkyl methacrylate resins which may be introduced with an acid-dissociating group; polyolefins; polyesters; polyamides; polyureas; and polyurethanes.

The above resins are blended in an amount not deteriorating the resist properties, preferably 0 to 49% by weight, more preferably 0 to 29% by weight, and still more preferably 0 to 19% by weight, each based on the total weight of the solid component. Within the above ranges, the resolution is high and resist patterns with a small edge roughness are obtained.

The compound B dissolves in at least one solvent selected from propylene glycol monomethyl ether acetate, propylene glycol monomethyl ether, ethyl lactate, butyl acetate, methyl 3-methoxypropionate, and ethyl propionate at 23° C. in a concentration of preferably 1% by weight or more, more preferably 3% by weight or more, and still more preferably 5% by weight or more. With such solubility, the troubles such as the precipitation of the compound B after made into the composition and the change of the properties of composition can be avoided, and the safety solvent acceptable in the semiconductor factory can be used.

The radiation-sensitive composition containing the compound B as the main ingredient combines a heat resistance withstanding the conductor process; a solubility to safety solvents such as propylene glycol monomethyl ether acetate, propylene glycol monomethyl ether, ethyl lactate, butyl acetate, methyl 3-methoxypropionate, and ethyl propionate; a good film-forming property; a good adhesion to silicon substrates; a good alkali developability, a good etching resistance, a small outgas amount upon exposure to light, a high resolution, and a small edge roughness.

The radiation-sensitive composition containing the polyphenol compound A, compound B and compound C as the main ingredients is usable as the resist for shade mask, because the solid component in the composition has a high absorptivity coefficient to 248 nm light employed in a KrF lithography. The solid component is formed into an amorphous film by a spin coating method and made into a resist pattern for shade mask. The absorptivity coefficient of the resist for shade mask is preferably 15 L/(cm·g) or more, more preferably 30 L/(cm·g) or more and still more preferably 40 L/(cm·g) or more.

The compound B can be formed into an amorphous film by a spin coating method, and then, made in to a resist pattern. The compound B is also applicable to a general semiconductor production process.

The dissolving speed of the amorphous film of the compound B to a 2.38 mass % aqueous solution of TMAH (tetramethylammonium hydroxide) at 23° C. is preferably 5 Å/sec or less, more preferably 0.05 to 5 Å/sec, and still more preferably 0.0005 to 5 Å/sec. If being 5 Å/sec or less, the compound B is insoluble to the alkali developing solution to form a resist. If being 0.0005 Å/sec or more, the resolution may be improved in some cases. This may be because that the micro surface of the compound B is dissolved to reduce LER. In addition, the effect for reducing the defects is obtained.

The polyphenol compound A which is generated by the dissociation of the acid-dissociating group of the compound B preferably has an ability of forming an amorphous film by a spin coating. The dissolving speed of the amorphous film of the polyphenol compound A to a 2.38 mass % aqueous solution of TMAH at 23° C. is preferably 10 Å/sec or more, more preferably 10 to 10000 Å/sec, and still more preferably 100 to 1000 Å/sec. If being 10 Å/sec or more, the polyphenol compound A dissolves to alkali developing solution to leave a resist. If being 10000 Å/sec or less, the resolution may be improved in some cases. This may be because that the contrast between the exposed portion soluble to the alkali developing solution and the non-exposed portion insoluble to the alkali developing solution is enhanced by the change of solubility due to the dissociation of the acid-dissociating group of the compound B. In addition, the effect for reducing LER and the defects is obtained.

The dissolving speed of the amorphous film which is formed by spin-coating the solid component of the radiation-sensitive composition to a 2.38 mass % aqueous solution of TMAH at 23° C. is preferably 5 Å/sec or less. After exposed with a radiation such as KrF excimer lasers, extreme ultraviolet rays, electron beams and X-rays and an optional heating at 20 to 250° C., the amorphous film preferably has a dissolving speed of 10 Å/sec or more to a 2.38 mass % aqueous solution of TMAH at 23° C. By satisfying the above requirements, a pattern with a good shape can be obtained in good yields.

The glass transition temperature of the polyphenol compound A is preferably 130° C. or more, more preferably 140° C. or more, and still more preferably 150° C. or more. Within the above ranges, a heat resistance enough to maintain the shape of pattern during the semiconductor lithography process is obtained, to increase the resolution.

The quantity of crystallization heat of the polyphenol compound A is preferably less than 20 J/g when measured by a differential scanning calorimetry. The difference, (crystallization temperature)−(glass transition temperature), is preferably 70° C. or more, more preferably 80° C. or more, still more preferably 100° C. or more, and particularly preferably 130° C. or more. If the quantity of crystallization heat is less than 20 J/g or the difference, (crystallization temperature)−(glass transition temperature), is within the above ranges, the amorphous film of the radiation-sensitive composition is easy to form by a spin coating and the film-forming properties required for the resist can be maintained for a long period of time, to improve the resolution. The measuring methods for the quantity of crystallization heat, crystallization temperature and glass transition temperature will be described below.

The radiation-sensitive composition may be included with one or more additives such as a solubility controller, sensitizer and surfactant.

The solubility controller is a component for adequately reducing the dissolving speed of the compound B to an alkali developing solution in the developing operation by lowering the solubility, if the solubility is excessively high.

Examples of the solubility controller include aromatic hydrocarbons such as naphthalene, phenanthrene, anthracene, and acenaphthene; ketones such as acetophenone, benzophenone, and phenyl naphthyl ketone; and sulfones such as methyl phenyl sulfone, diphenyl sulfone, and dinaphthyl sulfone. Bisphenols introduced with an acid-dissociating group and tris(hydroxyphenyl)methanes introduced with a t-butylcarbonyl group are also usable as the solubility controller. These solubility controllers may be used alone or in combination of two or more. The blending amount of the solubility controller is preferably 0 to 50% by weight, more preferably 0 to 40% by weight, and still more preferably 0 to 30% by weight, each based on the total weight of the solid component, although depending upon the kind of the compound B to be used.

The sensitizer is a compound for increasing the generation of acid by absorbing the energy of irradiated radiation and transferring the absorbed energy to the acid generator, thereby enhancing the apparent sensitivity of the resist. Examples of the sensitizer include, but not limited to, benzophenones, biacetyls, pyrenes, phenothiazines, and fluorenes. The sensitizer may be used alone or in combination of two or more. The blending amount of the sensitizer is preferably 0 to 50% by weight, more preferably 0 to 20% by weight and still more preferably 0 to 10% by weight, each based on the total amount of the solid component.

The surfactant is a compound for improving the coating properties and striation of the radiation-sensitive composition and the developability of the resist, etc. The surfactant may be any of anionic, cationic, nonionic and ampholytic, with nonionic surfactants being preferred because they are more effective due to a good affinity to solvents to be used for the production of the radiation-sensitive composition. Examples of the nonionic surfactant include, but not limited to, polyoxyethylene higher alkyl ethers, polyoxyethylene higher alkyl phenyl ethers, and higher fatty acid diesters of polyethylene glycol, which are commercially available under the tradenames: "EFTOP" of Jemco Inc.; "MEGAFACE" of Dai-Nippon Ink & Chemicals, Inc.; "FLUORAD" of Sumitomo 3M Ltd.; "ASAHIGUARD" and "SURFLON" of Asahi Glass Co., Ltd.; "PEPOL" of Toho Chemical Industry Co., Ltd.; "KP" of Shin-Etsu Chemical Co., Ltd.; and "POLYFLOW" of Kyoeisha Chemical Co., Ltd.

The blending amount of the surfactant is preferably 0 to 2% by weight, more preferably 0 to 1% by weight and still more preferably 0 to 0.1% by weight, each based on the total weight of the solid component. The latent image of the exposed area can be visualized by blending a dye or pigment, this reducing the influence of the halation during exposure. In addition, the adhesion to the substrate can be improved by blending an adhesive aid.

To prevent the reduction of the sensitivity upon the blending of the acid-diffusion controller or to improve the shape of resist patterns and the stability during the time delay, an organic carboxylic acid or oxo acid of phosphorus or it derivative may be optionally blended alone or in combination with the acid-diffusion controller. Preferred examples of the organic carboxylic acid include malonic acid, citric acid, malic acid, succinic acid, benzoic acid, and salicylic acid. Examples of the oxo acid of phosphorus and its derivative include phosphoric acid and its derivative such as ester, for example, phosphoric acid, di-n-butyl phosphate, and diphenyl phosphate; phosphonic acid and it derivative such as ester, for example, phosphonic acid, dimethyl phosphonate, di-n-butyl phosphonate, phenylphosphonic acid, diphenyl phosphonate, and dibenzyl phosphonate; and phosphinic acid and its derivative such as ester, for example, phosphinic acid and phenylphosphinic acid, with phosphonic acid being particularly preferred.

Examples of the solvent for the radiation-sensitive composition include, but not limited to, ethylene glycol monoalkyl ether acetates such as ethylene glycol monomethyl ether acetate and ethylene glycol monoethyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate (PGMEA) and propylene glycol monoethyl ether acetate; propylene glycol monoalkyl ethers such as propylene glycol monomethyl ether (PGME) and propylene glycol monoethyl ether; lactic esters such as methyl lactate and ethyl lactate (EL); esters of aliphatic carboxylic acid such as methyl acetate, ethyl acetate, propyl acetate, butyl acetate, and ethyl propionate (PE); other esters such as methyl 3-methoxypropionate, 3-methoxyethyl propionate, methyl 3-ethoxypropionate, and 3-ethoxyethyl propionate; aromatic hydrocarbons such as toluene and xylene; ketones such as 2-heptanone, 3-heptanone, 4-heptanone, and cyclohexanone; and cyclic ethers such as tetrahydrofuran and dioxane. These solvents may be used alone or in combination of two or more.

In the formation of a resist pattern, the radiation-sensitive composition of the present invention is first applied on a substrate such as a silicon wafer, a gallium-arsenic wafer and an aluminum-coated wafer by a coating method such as spin coating, cast coating and roll coating to form a resist film. The thickness of the resist film is not critical, and preferably 0.01 to 10 μm, more preferably 0.05 to 1 μm, and still more preferably 0.08 to 0.5 μm.

The substrate may be treated in advance with a surface treating agent such as hexamethylenedisilazane, if necessary. Examples of the surface treating agent include silane coupling agents such as hexamethylenedisilazane (hydrolysis-polymerizable silane coupling agent having a polymerizable group, etc.), anchor coating agents or undercoating agents (polyvinyl acetal, acrylic resin, vinyl acetate resin, epoxy resin, urethane resin, etc.), and mixed coating agents of the undercoating agent and inorganic fine particles.

To prevent the contamination with amine, etc. floating in the surrounding atmosphere, the resist film may be coated with a protecting film, if necessary. The acid generated in the resist film by the irradiation with radiation is generally deactivated by the reaction with the floating amine, etc. which are reactive with the acid, to deteriorate the resist images and reduce the sensitivity. By forming the protecting film, these problems can be avoided. The material for the protecting film is preferably a water-soluble, acidic polymer such as polyacrylic acid and polyvinylsulfonic acid.

To obtain highly accurate fine patterns and reduce the outgas during the exposure, it is preferred to heat the resist film before the irradiation with radiation (before exposure). The heating temperature is preferably 20 to 250° C. and more preferably 40 to 150° C., although depending upon the blending ratio of each component in the radiation-sensitive composition.

Then, the resist film is exposed in a desired pattern with a radiation selected from the group consisting of KrF excimer lasers, extreme ultraviolet rays, electron beams and X-rays. The exposing conditions can be suitably selected according to the blending ratio of each component in the radiation-sensitive composition. In the present invention, it is preferred to conduct a heat treatment after the irradiation of radiation (after exposure) to stably form highly accurate fine patterns. The heating temperature after exposure (PEB) is preferably 20 to 250° C. and more preferably 40 to 150° C., although depending upon the blending ratio of each component in the radiation-sensitive composition.

Then, the exposed resist film is developed with an alkali developing solution to form desired resist patterns. As the alkali developing solution, there may be used an aqueous alkaline solution dissolving, for example, at least one alkaline compound selected from mono-, di- or trialkylamines, mono-, di- or trialkanolamines, heterocyclic amines, tetramethylammonium hydroxide (TMAH) and choline in a concentration of preferably 1 to 10% by weight and more preferably 1 to 5% by weight. The alkali developing solution may contain an appropriate amount of an alcohol such as methanol, ethanol and isopropyl alcohol, or a surfactant mentioned above, with the addition of isopropyl alcohol in 10 to 30% by weight being particularly preferred. After developing with such an aqueous alkaline solution, the developed patterns are generally washed with water.

After forming resist patterns, the substrate is etched to obtain a patterned wiring board. The etching may be performed by known methods such as dry-etching using a plasma gas and wet-etching using an alkali solution, a copper (II) chloride solution, an iron (III) chloride solution, etc. After forming resist patterns, the substrate may be plated, for example, by copper plating, solder plating, nickel plating or gold plating.

The remaining resist patterns after etching may be stripped off by an organic solvent or an alkaline aqueous solution stronger than the alkali developing solution. Examples of the organic solvent include PGMEA, PGME, EL, acetone and tetrahydrofuran. Examples of the strong alkaline aqueous solution include a 1 to 20% by weight aqueous solution of sodium hydroxide and 1 to 20% by weight aqueous solution of potassium hydroxide. The stripping of the resist patterns may be performed by dipping method, spray method, etc. The wiring board having the resist patterns thereon may be a multi-layered wiring board and may be formed with small through-holes.

The wiring board may be produced by a lift-off method in which a metal is vacuum-deposited after forming resist patterns using the radiation-sensitive composition and then the remaining resist patterns are removed by dissolution into a solution.

EXAMPLES

The present invention will be described in more detail with reference to the following examples. However, it should be noted that the scope of the present invention is not limited thereto. The compounds, radiation-sensitive compositions and resist patterns were evaluated by the following methods.
(1) Evaluation of Polyphenol A
(1-1) Glass Transition Temperature, Crystallization Temperature and Quantity of Crystallization Heat A sample (about 10 mg) placed in a non-sealed aluminum container was heated to a temperature higher than the melting point at a temperature rising rate of 20° C./min in a nitrogen gas flow (50 ml/min). After being rapidly cooled, the sample was again heated to a temperature higher than the melting point at a temperature rising rate of 20° C./min in a nitrogen gas flow (30 ml/min). After being rapidly cooled, the sample was again heated to 400° C. at a temperature rising rate of 20° C./min in a nitrogen gas flow (30 ml/min), to conduct a differential scanning calorimetric analysis using DSC/TA-50WS manufactured by Shimadzu Corporation. The middle point of the region at which the base line turned discontinuous (the point at which the specific heat reduced to half) was taken as the glass transition temperature (Tg) and the temperature of the exothermic peak after the discontinuous region was taken as the crystallization temperature. The quantity of crystallization heat was determined by the area of the region which was surrounded by the exothermic peak and the base line. The sample was rated A when meeting Tg≧130° C., and rated C when meeting Tg≦130° C. Also, the sample was rated A when meeting (glass transition temperature)–(crystallization temperature)≧70° C., and rated C when meeting (glass transition temperature)–(crystallization temperature)≦70° C.

(1-2) Amount of Residual Metal

A sample weighed in a Teflon container was added with nitric acid and super pure water, and wet-ashed using a hermetic microwave sample preparation device "Ethos Plus" manufactured by Milestone Inc. The obtained ash was diluted with super pure water, and the amount of residual metal was determined using "ICP-MS HP4500-Shield Torch" manufactured by Hewlett-Packard Company. The sample was rated A when the amount was less than 1 ppm and rated C when 1 ppm or more.

(1-3) Alkali-Dissolving Speed

A 3% by weight solution of polyphenol A in PGME/PE (½ by weight) or acetone when not dissolved in PGME/PE was spin-coated to form a resist film with a thickness of about 0.05 µm. After heating on a hot plate at 11° C. for 3 min, the resist film was immersed in a 2.38% aqueous solution of TMAH at 23° C. The dissolving speed was determined by the change in the thickness of resist film between before and after the immersion. The sample was rated C when the speed was less than 10 Å/s, and rated A when 10 Å/s or higher.

(2) Evaluation of Compound B and Mixture (Compound B and Polyphenol A)

(2-1) Solubility in Safety Solvent

The solubility of the compound B was tested at 23° C. using propylene glycol monomethyl ether acetate, propylene glycol monomethyl ether, ethyl lactate, butyl acetate, methyl 3-methoxypropionate and ethyl propionate. The sample was rated A when dissolved in any one of the above solvents in a concentration of 5 wt % or more, rated B when dissolved in a concentration of 0.1 to 5 wt %, and rated C when dissolved only in a concentration of less than 0.1 wt %.

(2-2) Film-Forming Property

A 3% by weight solution of the compound B or a mixture (compound B and polyphenol A) in PGME/PE (½ by weight) or acetone when not dissolved in PGME/PE was spin-coated on a silicon wafer which had been surface-treated with a silane coupling agent, to form a resist film with a thickness of about 0.05 µm. After heating at 110° C. for 3 min on a hot plate, the resist film was observed for its appearance.

The sample was rated C when the film was clouded or its surface was roughened, rated B when the film was partly clouded or roughened, and rated A when the film had a good surface flatness without causing clouding.

(2-3) Dissolving Speed in Alkali Developing Solution

The resist film obtained in (2-2) was immersed in a 2.38% aqueous solution of TMAH at 23° C. The dissolving speed was determined by the change in the thickness of resist film between before and after the immersion. The sample was rated A when the speed was less than 10 Å/s, and rated C when 10 Å/s or higher.

(2-4) Adhesion to Silicon Substrate

The resist film formed in (2-2) was tested for its adhesion to the silicon wafer which was surface-treated with a silane coupling agent. The sample was rated A when the film was not peeled from the silicon wafer, and rated C when peeled off.

(3) Evaluation of Resist Patterns (3-1) Formation of Resist Film

A blend of the components shown in Table 5 was filtered through a 0.1-µm Teflon (trademark) filter to prepare a radiation-sensitive composition. Each radiation-sensitive composition was spin-coated on a silicon wafer and dried at 110° C. for 90 s on a hot plate, to form a resist film with a thickness of about 0.05 µm.

(3-2) Formation of Resist Patterns

The resist film was irradiated with electron beams using an electron beam lithography system ("ELS-7500" manufactured by Elionix Co., Ltd.; acceleration voltage: 50 keV). After irradiation, each resist film was heated for 90 s at predetermined temperature, immersed in a 2.38% by weight aqueous solution of TMAH for 60 s, rinsed with distilled water for 30 s, and then dried. The resultant line-and-space patterns were observed under a scanning electron microscope ("S-4800" manufactured by Hitachi High-Technologies Corporation). In any samples of the examples, the amount of the outgas during the exposure was small.

(3-3) Sensitivity and Resolution

The resolution limit of the line-and-space patterns was taken as the resolution. The minimum amount of exposure for achieving the resolution limit was taken as the sensitivity.

(3-4) Line Edge Roughness (LER)

The distance between the edge and the base line was measured at 300 points which were randomly selected along the lengthwise direction (1.5 µm) of the 80-nm interval line patterns formed by the minimum amount of exposure for achieving the resolution limit. The measurement was conducted using Hitachi Semiconductor SEM, terminal PC and V5 off-line measuring software (available from Hitachi Science Systems, Ltd.). From the measured results, the standard deviation (3σ) was calculated.

Synthesis Example 1

Synthesis of tetrakis(2,5-xylenol)-2,6-naphthalenedialdehyde (Compound 101)

A mixture of 195 g (1.6 mol) of 2,5-xylenol (Kanto Chemical Co., Inc.) and 20.0 g (0.1 mol) of 2,6-naphthalenedialdehyde (synthesized by the method described in JP 2003-155259A) was made into a solution under heating to about 60° C. After adding 0.2 ml of sulfuric acid (Kanto Chemical Co., Inc.) and 1.6 ml of 3-mercaptopropionic acid (Kanto Chemical Co., Inc.) to the solution, the reaction was allowed to proceed under stirring. After confirming 100% conversion by a liquid chromatography, 100 ml of toluene (Kanto Chemical Co., Inc.) was added. The solid precipitated by cooling was filtered under reduced pressure, washed with a warm water of 60° C. under stirring, and purified by a silica gel column chromatography, to obtain the title compound. The structure of the compound was determined by elemental analysis and $^1$H-NMR measurement (400 MHz, d-DMSO, TMS internal standard). The results are shown in Tables 2 and 3.

Synthesis Examples 2-8

Synthesis of Compounds 102 to 108

Each title compound was synthesized in the same manner as in Synthesis Example 1 except for changing 2,5-xylenol and 2,6-naphthalenedialdehyde to the compounds listed in Table 1.

The structure of each compound was determined by elemental analysis and 1H-NMR measurement (400 MHz, d-DMSO, TMS internal standard). The results are shown in Tables 2 and 3.

TABLE 1

(Synthesis of Polyphenol A)

| Synthesis Examples | Compound Nos. | aromatic polyketone or aromatic polyaldehyde | Compound having phenolic hydroxyl group |
|---|---|---|---|
| 1 | 101 | 2,6-naphthalenedialdehyde*[1] | 2,5-xylenol |
| 2 | 102 | 2,6-naphthalenedialdehyde*[1] | 2,3,6-trimethylphenol |
| 3 | 103 | 2,6-naphthalenedialdehyde*[1] | thymol |
| 4 | 104 | 2,7-naphthalenedialdehyde*[2] | 2,5-xylenol |
| 5 | 105 | 2,7-naphthalenedialdehyde*[2] | 2,3,6-trimethylphenol |
| 6 | 106 | m-terphenyldialdehyde*[3] | 2,5-xylenol |
| 7 | 107 | p-terphenyldialdehyde*[4] | 2,5-xylenol |
| 8 | 108 | 1,3,5-benzenetricarbaldehyde*[5] | 2,3,6-trimethylphenol |

*[1]Synthesized by the method described in JP 2003-155259A.
*[2]Synthesized in the same manner as in *[1] except for changing 2,6-dimethylnaphthalene to 2,7-dimethylnaphthalene. 2,7-Dimethylnaphthalene was synthesized by the method described in Japanese Patent 3115053.
*[3]Synthesized in the same manner as in *[4] except for changing p-terphenyl to m-terphenyl (Tokyo Kasei Kogyo Co., Ltd.).
*[4]Synthesized by the method described in J. Am. Chem. Soc., Vol.114, No.15, 1992.
*[5]Synthesized by the method described in Chem. Ber., 1954, 87, 54.

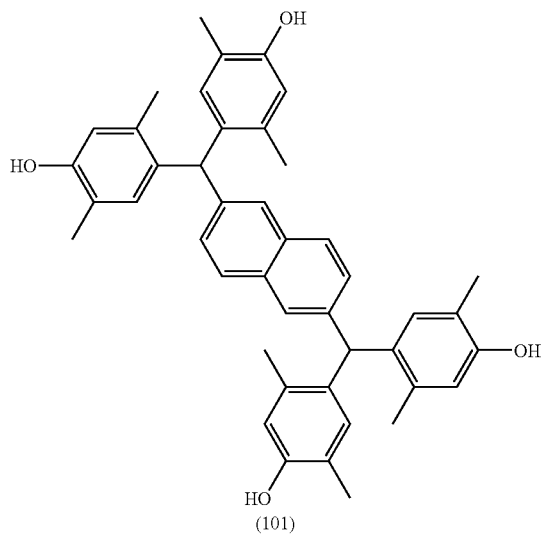
(101)

TABLE 1-continued
(Synthesis of Polyphenol A)
| Synthesis Examples | Compound Nos. | aromatic polyketone or aromatic polyaldehyde | Compound having phenolic hydroxyl group |
|---|---|---|---|
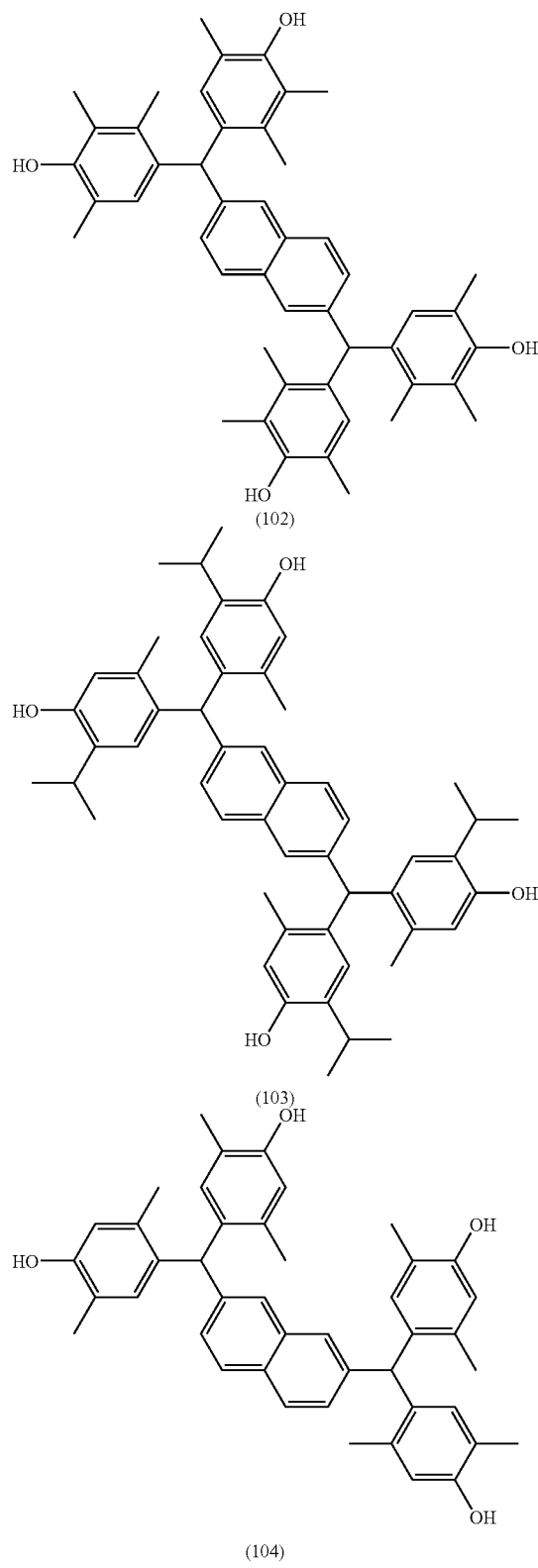
(102)
(103)
(104)

TABLE 1-continued
(Synthesis of Polyphenol A)
| Synthesis Examples | Compound Nos. | aromatic polyketone or aromatic polyaldehyde | Compound having phenolic hydroxyl group |
|---|---|---|---|
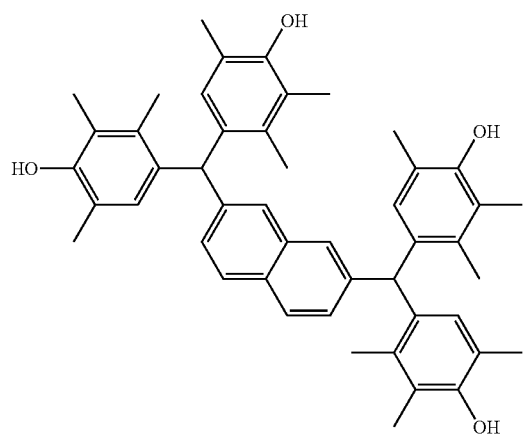
(105)
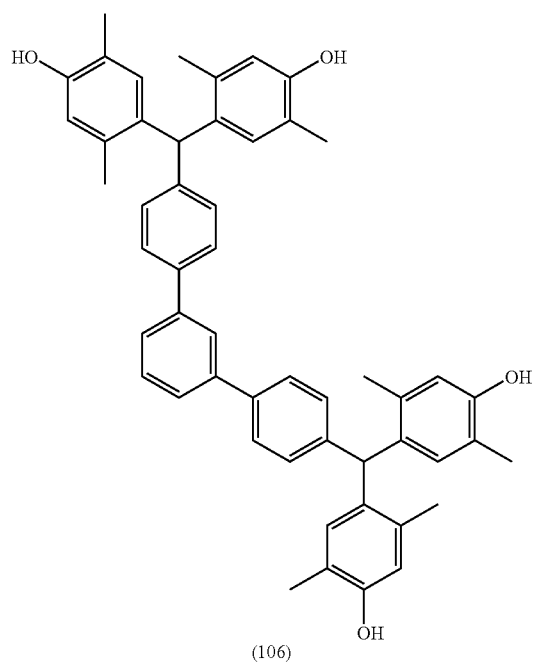
(106)

TABLE 1-continued
(Synthesis of Polyphenol A)
| Synthesis Examples | Compound Nos. | aromatic polyketone or aromatic polyaldehyde | Compound having phenolic hydroxyl group |
|---|---|---|---|
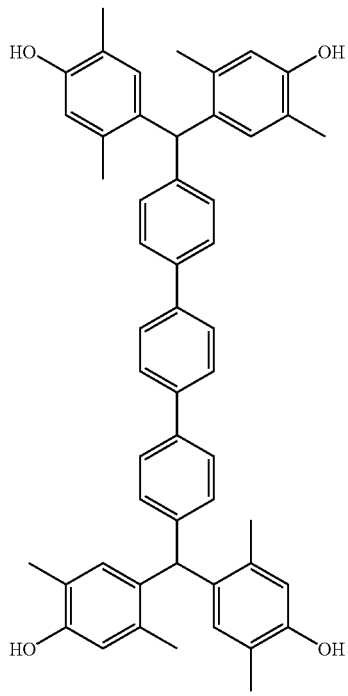
(107)
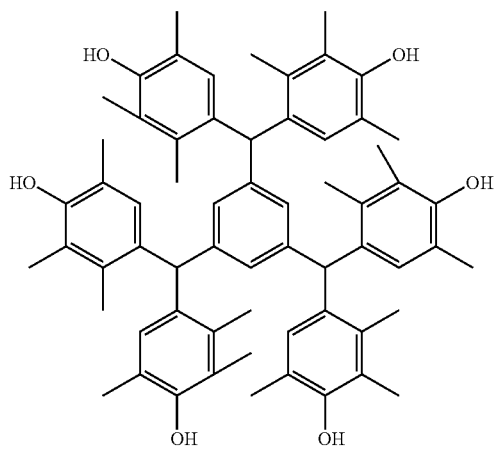
(108)
TABLE 2
(Elemental analysis of polyphenol A)
| Synthesis Example | Compound Nos. | Empirical formula | | | Molecular weight | Calculated | | | Found | |
|---|---|---|---|---|---|---|---|---|---|---|
| | | C | H | O | | C | H | O | C | H |
| 1 | 101 | 44 | 44 | 4 | 636 | 82.99 | 6.96 | 10.05 | 82.9 | 6.9 |
| 2 | 102 | 48 | 52 | 4 | 692 | 83.20 | 7.56 | 9.24 | 83.0 | 7.0 |
| 3 | 103 | 52 | 60 | 4 | 748 | 83.38 | 8.07 | 8.54 | 83.1 | 8.0 |
| 4 | 104 | 44 | 44 | 4 | 636 | 82.99 | 6.96 | 10.05 | 82.9 | 6.9 |
| 5 | 105 | 48 | 52 | 4 | 692 | 83.20 | 7.56 | 9.24 | 83.1 | 7.6 |

TABLE 2-continued (Elemental analysis of polyphenol A)

| Synthesis Example | Compound Nos. | Empirical formula C | H | O | Molecular weight | Calculated C | H | O | Found C | H |
|---|---|---|---|---|---|---|---|---|---|---|
| 6 | 106 | 52 | 50 | 4 | 738 | 84.52 | 6.82 | 8.66 | 84.4 | 6.8 |
| 7 | 107 | 52 | 50 | 4 | 738 | 84.52 | 6.82 | 8.66 | 84.4 | 6.7 |
| 8 | 108 | 63 | 72 | 6 | 924 | 81.78 | 7.84 | 10.38 | 71.8 | 7.7 |

TABLE 3

($^1$H-NMR of Polyphenol A)

| Synthesis Example | Compound Nos. | $^1$H-NMR |
|---|---|---|
| 1 | 101 | 9.0 (4H, —OH), 6.4-7.7 (14H, PhH—), 5.6 (2H, —CH—), 1.9-2.0 (24H, Ph-CH$_3$) |
| 2 | 102 | 7.9 (4H, —OH), 6.3-7.6 (10H, PhH—), 5.7 (2H, —CH—), 1.9-2.0 (36H, Ph-CH$_3$) |
| 3 | 103 | 9.0 (4H, —OH), 6.5-7.7 (14H, PhH—), 5.6 (2H, —CH—), 3.0-3.2 (4H, -Ph-CH(CH$_3$)$_2$), 1.9-2.0 (12H, Ph-CH$_3$), 0.9-1.1 (24H, -Ph-CH(CH$_3$)$_2$) |
| 4 | 104 | 9.1 (4H, —OH), 6.4-7.8 (14H, PhH—), 5.6 (2H, —CH—), 1.9-2.0 (24H, Ph-CH$_3$) |
| 5 | 105 | 7.9 (4H, —OH), 6.3-7.8 (10H, PhH—), 5.7 (2H, —CH—), 1.9-2.0 (36H, Ph-CH$_3$) |
| 6 | 106 | 10.1 (4H, —OH), 6.4-7.7 (20H, PhH), 5.5 (2H, —CH—), 1.9-2.0 (24H, Ph-CH$_3$) |
| 7 | 107 | 9.0 (4H, —OH), 6.4-7.8 (20H, PhH), 5.5 (2H, —CH—), 1.9-2.0 (24H, Ph-CH$_3$) |
| 8 | 108 | 7.8 (6H, —OH), 6.0-6.4 (9H, PhH), 5.3 (3H, —CH—), 1.8-2.1 (54H, Ph-CH$_3$) |

Synthesis Example 9

Synthesis of Compound 109

A solution of 0.6 g (0.9 mmol) of Compound 101, 5 ml of dry acetone, 0.18 g of pyridinium p-toluenesulfonate, and 0.2 g (2.8 mmol) of ethyl vinyl ether was stirred at room temperature for 24 h. The reaction product solution was purified by a silica gel column chromatography (elute: ethyl acetate/hexane=1/2), to obtain the title compound (compound B). The structure of the compound was determined by elemental analysis and $^1$H-NMR measurement (400 MHz, d-DMSO, TMS internal standard). The results are shown in Tables 5 and 6.

Synthesis Examples 10-16 and 18-19

Synthesis of Compounds 110 to 116 and 118 to 119

Each title compound (compound B) was synthesized in the same manner as in Synthesis Example 9 except for changing Compound 101 and ethyl vinyl ether to the compounds listed in Table 4. The structure of each compound was determined by elemental analysis and $^1$H-NMR measurement (400 MHz, d-DMSO, TMS internal standard). The results are shown in Tables 5 and 6.

Synthesis Example 17

A solution of 0.6 g (0.9 mmol) of Compound 108 in 5 ml of dimethylacetamide was added dropwise with 2.34 g (11 mmol) of di-tert-butyldicarbonate and 1.2 g of triethylamine slowly and stirred at 60° C. for 7 h. The reaction product solution was added to a large amount of water and the reprecipitation was repeated, to obtain a white powder which was then dried under reduced pressure to obtain the aimed compound 117 (compound B). The structure of the compound was determined by elemental analysis and $^1$H-NMR measurement (400 MHz, d-DMSO, TMS internal standard). The results are shown in Tables 5 and 6.

TABLE 4

(Synthesis of Compound B)

| Synthesis Example | Compound Nos. | Polyphenol A | Compound for introducing acid-dissociating group |
|---|---|---|---|
| 9 | 109 | 101 | ethyl vinyl ether |
| 10 | 110 | 101 | cyclohexyloxy vinyl ether |
| 11 | 111 | 102 | ethyl vinyl ether |
| 12 | 112 | 102 | cyclohexyloxy vinyl ether |
| 13 | 113 | 103 | cyclohexyloxy vinyl ether |
| 14 | 114 | 105 | cyclohexyloxy vinyl ether |
| 15 | 115 | 106 | cyclohexyloxy vinyl ether |

TABLE 4-continued
| | (Synthesis of Compound B) | | |
|---|---|---|---|
| Synthesis Example | Compound Nos. | Polyphenol A | Compound for introducing acid-dissociating group |
| 16 | 116 | 107 | cyclohexyloxy vinyl ether |
| 17 | 117 | 108 | di-t-butyldicarbonate |
| 18 | 118 | 104 | cyclohexyloxy vinyl ether |
| 19 | 119 | 108 | cyclohexyloxy vinyl ether |
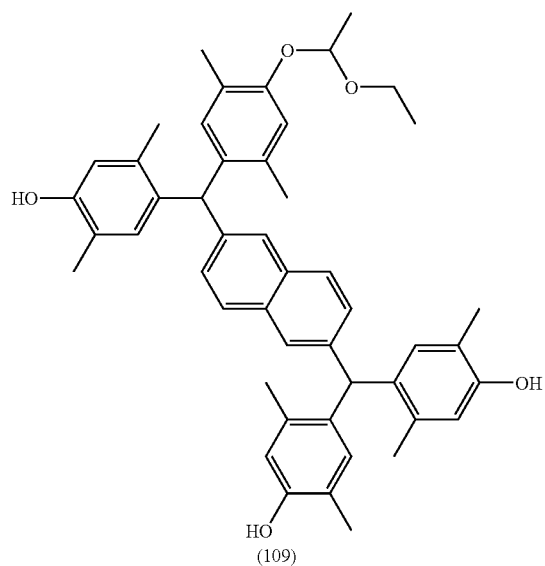
(109)
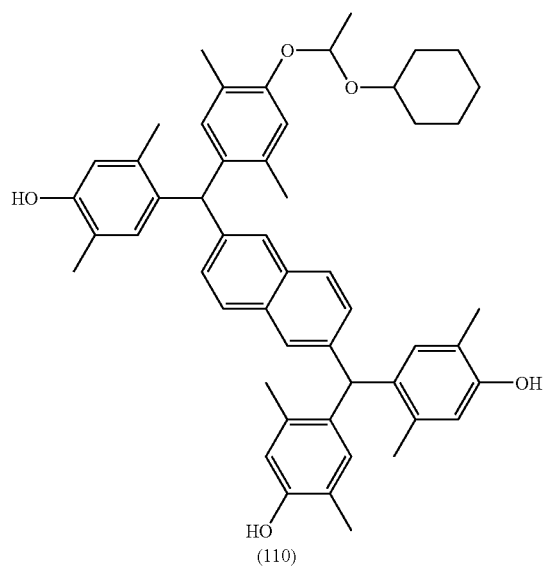
(110)

TABLE 4-continued
(Synthesis of Compound B)
| Synthesis Example | Compound Nos. | Polyphenol A | Compound for introducing acid-dissociating group |
|---|---|---|---|
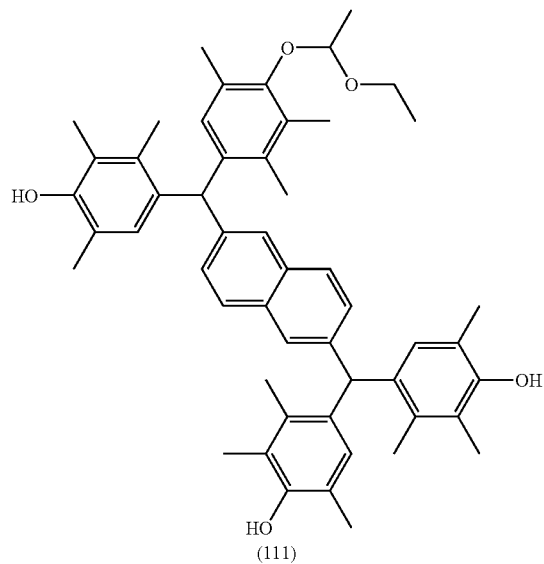
(111)
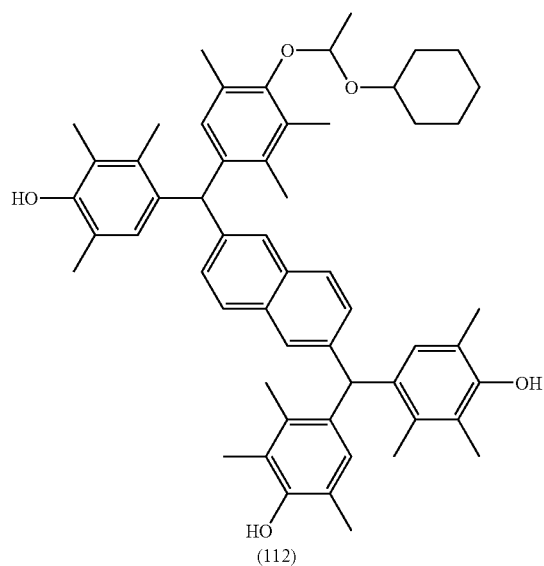
(112)

TABLE 4-continued
(Synthesis of Compound B)
| Synthesis Example | Compound Nos. | Polyphenol A | Compound for introducing acid-dissociating group |
|---|---|---|---|
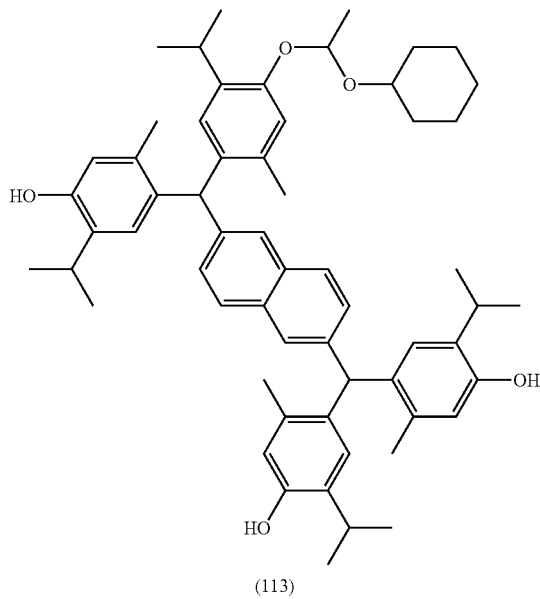
(113)
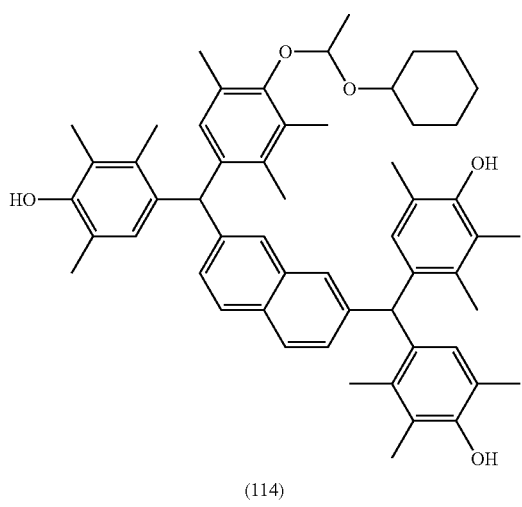
(114)

TABLE 4-continued
| | | (Synthesis of Compound B) | |
|---|---|---|---|
| Synthesis Example | Compound Nos. | Polyphenol A | Compound for introducing acid-dissociating group |
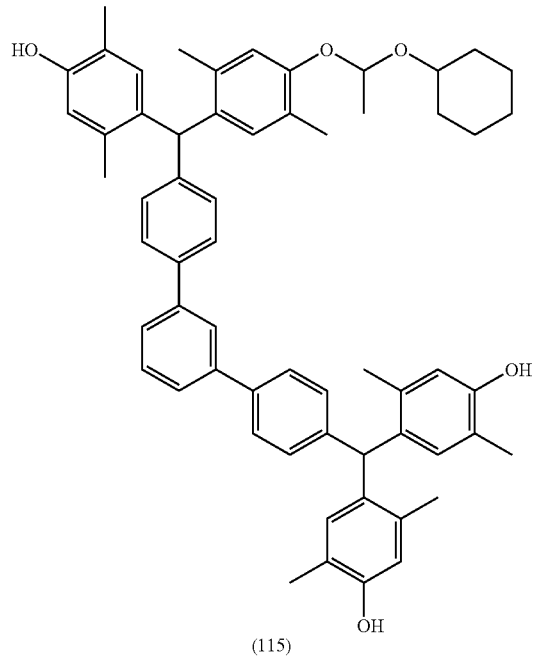
(115)
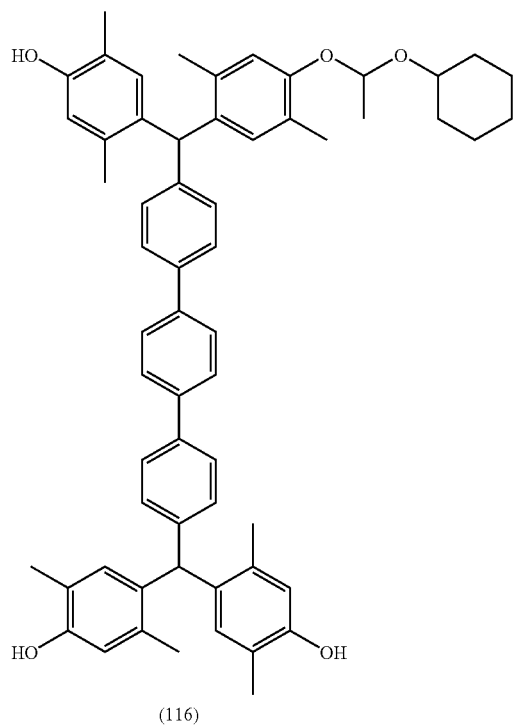
(116)

TABLE 4-continued
(Synthesis of Compound B)
| Synthesis Example | Compound Nos. | Polyphenol A | Compound for introducing acid-dissociating group |
|---|---|---|---|
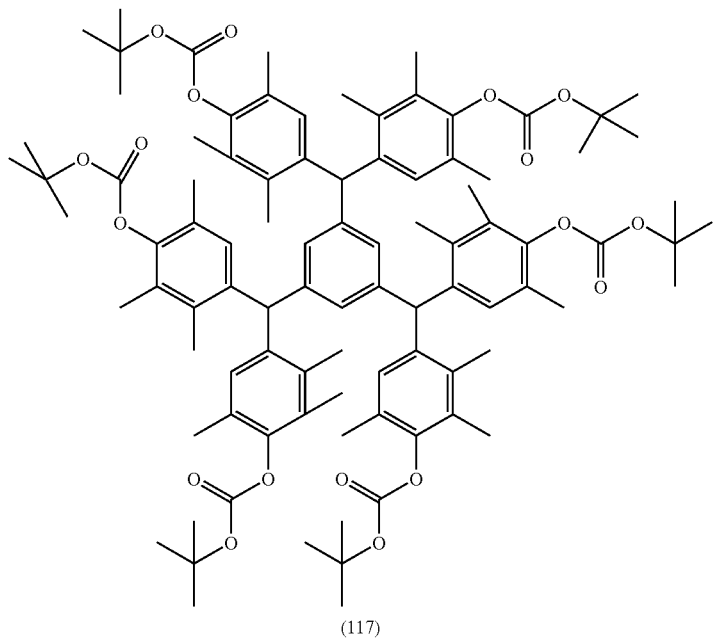
(117)
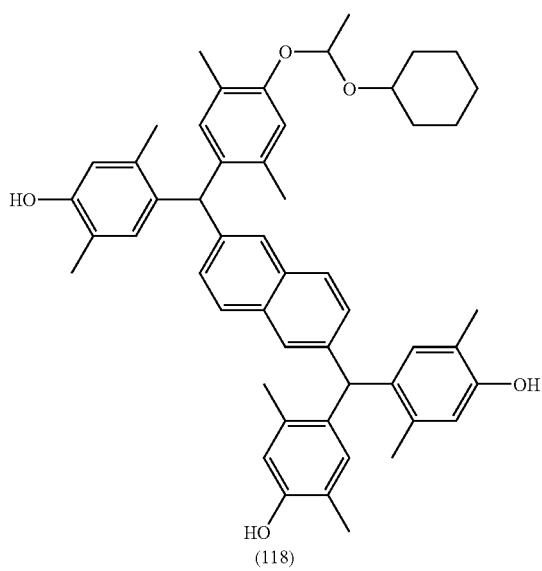
(118)

TABLE 4-continued (Synthesis of Compound B)

| Synthesis Example | Compound Nos. | Polyphenol A | Compound for introducing acid-dissociating group |
|---|---|---|---|

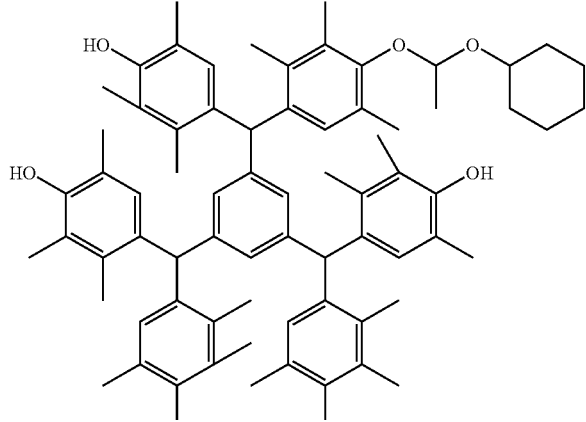

(119)

TABLE 5

(Elemental Analysis of Compound B)

| Synthesis Example | Compound Nos. | Empirical formula C | H | O | Molecular weight | Calculated C | H | O | Found C | H |
|---|---|---|---|---|---|---|---|---|---|---|
| 9 | 109 | 48 | 52 | 5 | 708.9 | 81.32 | 7.39 | 11.28 | 81.0 | 7.3 |
| 10 | 110 | 52 | 58 | 5 | 763.0 | 81.85 | 7.66 | 10.48 | 81.2 | 7.6 |
| 11 | 111 | 52 | 60 | 5 | 765.0 | 81.64 | 7.91 | 10.46 | 81.1 | 7.8 |
| 12 | 112 | 56 | 66 | 5 | 819.1 | 82.11 | 8.12 | 9.77 | 81.3 | 8.1 |
| 13 | 113 | 60 | 74 | 5 | 875.2 | 82.34 | 8.52 | 9.14 | 81.5 | 8.5 |
| 14 | 114 | 56 | 66 | 5 | 819.1 | 82.11 | 8.12 | 9.77 | 81.6 | 8.0 |
| 15 | 115 | 60 | 64 | 5 | 865.2 | 83.30 | 7.46 | 9.25 | 83.0 | 7.4 |
| 16 | 116 | 60 | 64 | 5 | 865.2 | 83.30 | 7.46 | 9.25 | 82.8 | 7.4 |
| 17 | 117 | 93 | 120 | 18 | 1525.9 | 73.20 | 7.93 | 18.87 | 73.2 | 7.9 |
| 18 | 118 | 52 | 58 | 5 | 763.0 | 81.85 | 7.66 | 10.48 | 81.7 | 7.6 |
| 19 | 119 | 71 | 86 | 7 | 1051.4 | 81.10 | 8.24 | 10.65 | 81.0 | 8.2 |

TABLE 6

($^1$H-NMR of Compound B)

| Synthesis Examples | Compound Nos. | $^1$H-NMR |
|---|---|---|
| 9 | 109 | 9.0 (3H, —O$\underline{H}$), 6.4-7.7 (14H, Ph$\underline{H}$—), 5.4-5.6 (3H, —C$\underline{H}$—), 3.5 (2H, CH$_3$C$\underline{H}_2$—), 1.9-2.0 (24H, Ph-C$\underline{H}_3$), 1.4 (3H, —CH(C$\underline{H}_3$)—), 1.1 (3H, —CH$_2$C$\underline{H}_3$) |
| 10 | 110 | 9.0 (3H, —O$\underline{H}$), 6.4-7.7 (14H, Ph$\underline{H}$—), 5.5-5.6 (3H, —C$\underline{H}$—), 3.5 (1H, Ch$\underline{H}$—), 1.9-2.0 (24H, Ph-C$\underline{H}_3$), 1.1-2.1 (10H, Ch$\underline{H}$—), 1.1 (3H, —C$\underline{H}_3$) |
| 11 | 111 | 7.9 (3H, —O$\underline{H}$), 6.2-7.6 (10H, Ph$\underline{H}$—), 5.0 (1H, —C$\underline{H}$—), 5.7-5.8 (2H, —C$\underline{H}$—), 3.3-3.4 (2H, CH$_3$C$\underline{H}_2$—), 1.9-2.0 (36H, Ph-C$\underline{H}_3$), 1.4 (3H, —CH(C$\underline{H}_3$)—), 1.1 (3H, —CH$_2$C$\underline{H}_3$) |
| 12 | 112 | 7.9 (3H, —O$\underline{H}$), 6.2-7.6 (10H, Ph$\underline{H}$—), 5.0 (1H, —C$\underline{H}$—), 5.7-5.8 (2H, —C$\underline{H}$—), 3.5 (1H, Ch$\underline{H}$—), 1.9-2.0 (36H, Ph-C$\underline{H}_3$), 1.1-2.1 (10H, Ch$\underline{H}$—), 1.1 (3H, —C$\underline{H}_3$) |
| 13 | 113 | 9.0 (3H, —O$\underline{H}$), 6.5-7.7 (14H, Ph$\underline{H}$—), 5.4-5.6 (3H, —C$\underline{H}$—), 3.5 (1H, Ch$\underline{H}$—), 3.0-3.2 (4H, -Ph-C$\underline{H}$(CH$_3$)$_2$), 1.9-2.0 (12H, Ph-C$\underline{H}_3$), 1.1-2.1 (10H, Ch$\underline{H}$—), 1.1 (3H, —C$\underline{H}_3$), 0.8-1.0 (24H, -Ph-CH(C$\underline{H}_3$)$_2$) |
| 14 | 114 | 7.9 (3H, —O$\underline{H}$), 6.3-7.8 (10H, Ph$\underline{H}$—), 5.1 (1H, —C$\underline{H}$—), 5.7 (2H, —C$\underline{H}$—), 3.5 (1H, Ch$\underline{H}$—), 1.9-2.0 (36H, Ph-C$\underline{H}_3$), 1.1-2.1 (10H, Ch$\underline{H}$—), 1.1 (3H, —C$\underline{H}_3$) |

TABLE 6-continued ($^1$H-NMR of Compound B)

| Synthesis Examples | Compound Nos. | $^1$H-NMR |
|---|---|---|
| 15 | 115 | 10.1 (3H, —OH), 6.4-7.9 (20H, PhH), 5.5 (3H, —CH—), 3.5 (1H, ChH—), 1.9-2.0 (24H, Ph-CH$_3$), 1.1-2.1 (10H, ChH—), 1.1 (3H, —CH$_3$) |
| 16 | 116 | 9.0 (3H, —OH), 6.4-7.8 (20H, PhH), 5.5 (3H, —CH—), 3.5 (1H, ChH—), 1.9-2.0 (24H, Ph-CH$_3$), 1.1-2.1 (10H, ChH—), 1.1 (3H, —CH$_3$) |
| 17 | 117 | 6.1-6.5 (9H, PhH), 5.6 (3H, —CH—), 1.9-2.0 (54H, Ph-CH$_3$), 1.5 (54H, (CH$_3$)$_3$—) |
| 18 | 118 | 9.0 (3H, —OH), 6.5-7.8 (14H, PhH—), 5.5-5.6 (3H, —CH—), 3.5 (1H, ChH—), 1.9-2.0 (24H, Ph-CH$_3$), 1.1-2.1 (10H, ChH—), 1.1 (3H, —CH$_3$) |
| 19 | 119 | 7.8 (5H, —OH), 6.1-6.5 (9H, PhH), 5.6 (3H, —CH—), 5.0 (1H, —CH—), 3.5 (1H, ChH—), 1.9-2.0 (54H, Ph-CH$_3$), 1.1-2.1 (10H, ChH—), 1.1 (3H, —CH$_3$) |

Synthesis Example 20

Synthesis of Mixture 120

A solution of 0.6 g (0.9 mmol) of Compound 101, 5 ml of dry acetone, 0.18 g of pyridinium p-toluenesulfonate and 0.2 g (2.8 mmol) of ethyl vinyl ether was stirred at room temperature for 24 h. The reaction product solution was purified by a silica gel column chromatography (elute: ethyl acetate/hexane=1/2), to obtain the title mixture. The structure of each compound was determined by $^1$H-NMR measurement (400 MHz, d-DMSO, TMS internal standard). The results are shown in Table 8.

Synthesis Examples 21-27 and 29-30

Synthesis of Mixtures 121-127 and 129-130

Each title mixture was synthesized in the same manner as in Synthesis Example 20 except for changing Compound 101 and ethyl vinyl ether to the compounds listed in Table 7. The structure of each compound was determined by elemental analysis and $^1$H-NMR measurement (400 MHz, d-DMSO, TMS internal standard). The results are shown in Table 8.

Synthesis Example 28

A solution of 0.6 g (0.9 mmol) of Compound 108 in 5 ml of dimethylacetamide was added dropwise with 2.34 g (11 mmol) of di-tert-butyldicarbonate and 1.2 g of triethylamine slowly and stirred at 60° C. for 7 h. The reaction product solution was added to a large amount of water and the reprecipitation was repeated, to obtain a white powder which was then dried under reduced pressure to obtain 1.95 g of the aimed mixture 118. The structure of each compound was determined by elemental analysis and $^1$H-NMR measurement (400 MHz, d-DMSO, TMS internal standard). The results are shown in Table 8.

TABLE 7

(Synthesis of Mixture (compound B + polyphenol A))

| Synthesis Examples | Mixture Nos. | Polyphenol A | Compound for introducing acid-dissociating group |
|---|---|---|---|
| 20 | 120 | 101 | ethyl vinyl ether |
| 21 | 121 | 101 | cyclohexyloxy vinyl ether |
| 22 | 122 | 102 | ethyl vinyl ether |
| 23 | 123 | 102 | cyclohexyloxy vinyl ether |
| 24 | 124 | 103 | cyclohexyloxy vinyl ether |
| 25 | 125 | 105 | cyclohexyloxy vinyl ether |
| 26 | 126 | 106 | cyclohexyloxy vinyl ether |
| 27 | 127 | 107 | cyclohexyloxy vinyl ether |
| 28 | 128 | 108 | di-t-butyldicarbonate |
| 29 | 129 | 104 | cyclohexyloxy vinyl ether |
| 30 | 130 | 108 | cyclohexyloxy vinyl ether |

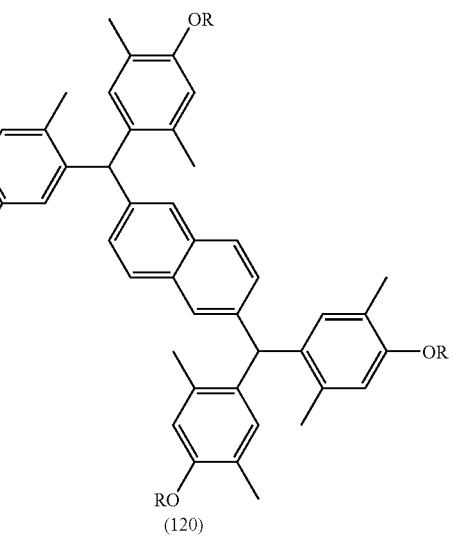

(120)

TABLE 7-continued (Synthesis of Mixture (compound B + polyphenol A))

| Synthesis Examples | Mixture Nos. | Polyphenol A | Compound for introducing acid-dissociating group |
|---|---|---|---|
| | (121) | | |
| | (122) | | |
| | (123) | | |
| | (124) | | |
| | (125) | | |

TABLE 7-continued
(Synthesis of Mixture (compound B + polyphenol A))
| Synthesis Examples | Mixture Nos. | Polyphenol A | Compound for introducing acid-dissociating group |
|---|---|---|---|
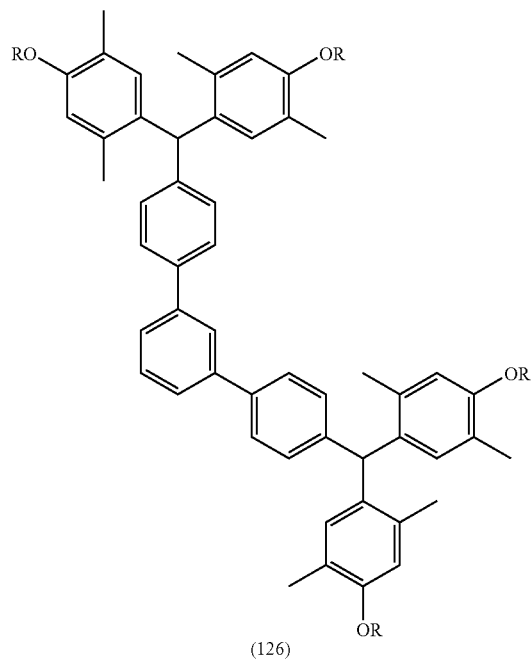
(126)
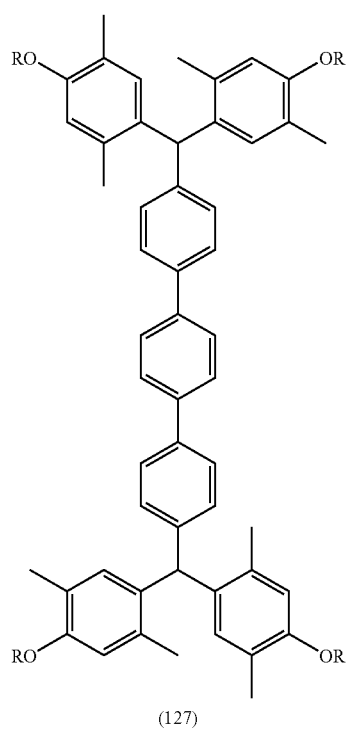
(127)
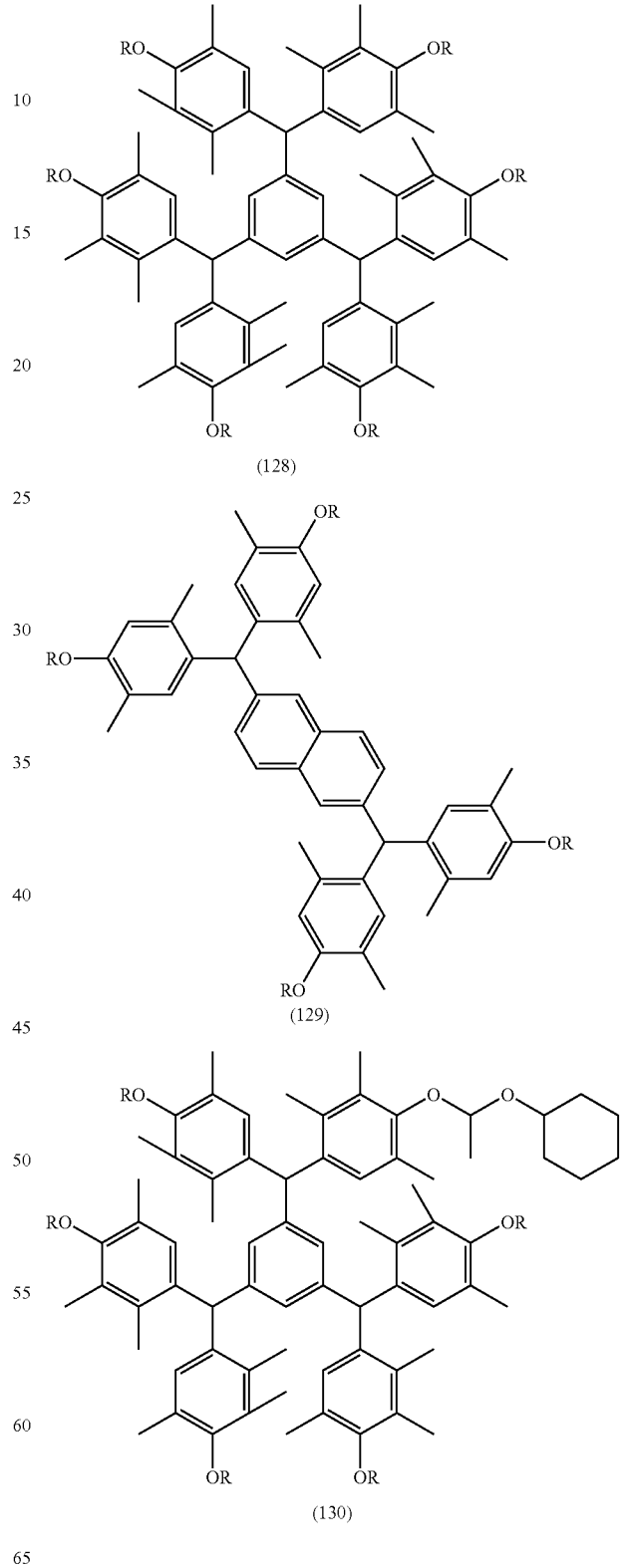
(128)
(129)
(130)
In the formulae 120-130, R is a hydrogen atom or an acid-dissociating group listed in Table 7.

TABLE 8

(¹H-NMR of Mixture)

| Synthesis Example | Mixture Nos. | ¹H-NMR | Introduction of acid-dissociating group (%) |
|---|---|---|---|
| 20 | 120 | 9.0 (1.68H, —O$\underline{H}$), 6.4-7.7 (14H, Ph$\underline{H}$—), 5.4-5.6 (4.32H, —C$\underline{H}$—), 3.5 (4.64H, CH$_3$C$\underline{H}_2$—), 1.9-2.0 (24H, Ph-C$\underline{H}_3$), 1.4 (6.96H, —CH(C$\underline{H}_3$)—), 1.1 (6.96H, —CH$_2$C$\underline{H}_3$) | 58 |
| 21 | 121 | 9.0 (3.2H, —O$\underline{H}$), 6.4-7.7 (14H, Ph$\underline{H}$—), 5.5-5.6 (2.8H, —C$\underline{H}$—), 3.5 (0.8H, Ch$\underline{H}$—), 1.9-2.0 (24H, Ph-C$\underline{H}_3$), 1.1-2.1 (8H, Ch$\underline{H}$—), 1.1 (2.4H, —C$\underline{H}_3$) | 20 |
| 22 | 122 | 7.9 (2.28H, —O$\underline{H}$), 6.2-7.6 (10H, Ph$\underline{H}$—), 5.0 (1.72H, —C$\underline{H}$—), 5.7-5.8 (2H, —C$\underline{H}$—), 3.3-3.4 (3.44H, CH$_3$C$\underline{H}_2$—) 19-2.0 (36H, Ph-C$\underline{H}_3$) 1.4 (5.16H, —CH(CH$_3$)—), 1.1 (5.16H, —CH$_2$CH$_3$) | 43 |
| 23 | 123 | 7.9 (3.48H, —O$\underline{H}$), 6.2-7.6 (10H, Ph$\underline{H}$—), 5.0 (0.52H, —C$\underline{H}$—), 5.7-5.8 (2H, —C$\underline{H}$—), 3.5 (0.52H, Ch$\underline{H}$—), 1.9-2.0 (36H, Ph-C$\underline{H}_3$), 1.1-2.1 (5.2H, Ch$\underline{H}$—), 1.1 (1.56H, —C$\underline{H}_3$) | 13 |
| 24 | 124 | 9.0 (2.16H, —O$\underline{H}$), 6.5-7.7 (14H, Ph$\underline{H}$—), 5.4-5.6 (3.84H, —C$\underline{H}$—), 3.5 (1.84H, Ch$\underline{H}$—), 3.0-3.2 (4H, -Ph-C$\underline{H}$(CH$_3$)$_2$), 1.9-2.0 (12H, Ph-C$\underline{H}_3$), 1.1-2.1 (18.4H, Ch$\underline{H}$—), 1.1 (5.52H, —C$\underline{H}_3$), 0.8-1.0 (24H, -Ph-CH(C$\underline{H}_3$)$_2$) | 46 |
| 25 | 125 | 7.9 (2.8H, —O$\underline{H}$), 6.3-7.8 (10H, Ph$\underline{H}$), 5.1 (1.2H, —C$\underline{H}$—), 5.7 (2H, —C$\underline{H}$—), 3.5 (1.2H, Ch$\underline{H}$—), 1.9-2.0 (36H, Ph-C$\underline{H}_3$), 1.1-2.1 (12H, Ch$\underline{H}$—), 1.1 (3.6H, —C$\underline{H}_3$) | 30 |
| 26 | 126 | 10.1 (3H, —O$\underline{H}$), 6.4-7.9 (20H, Ph$\underline{H}$), 5.5 (3H, —C$\underline{H}$—), 3.5 (1H, Ch$\underline{H}$—), 1.9-2.0 (24H, Ph-C$\underline{H}_3$), 1.1-2.1 (10H, Ch$\underline{H}$—), 1.1 (3H, —C$\underline{H}_3$) | 25 |
| 27 | 127 | 9.0 (3.28H, —O$\underline{H}$), 6.4-7.8 (20H, Ph$\underline{H}$), 5.5 (2.72H, —C$\underline{H}$—), 3.5 (0.72H, Ch$\underline{H}$—), 1.9-2.0 (24H, Ph-C$\underline{H}_3$), 1.1-2.1 (10H, Ch$\underline{H}$—), 1.1 (3H, —C$\underline{H}_3$) | 18 |
| 28 | 128 | 6.1-6.5 (9H, Ph$\underline{H}$), 5.6 (3H, —C$\underline{H}$—), 1.9-2.0 (54H, Ph-C$\underline{H}_3$), 1.5 (54H, (C$\underline{H}_3$)$_3$—) | 100 |
| 29 | 129 | 9.0 (2.48H, —O$\underline{H}$), 6.4-7.7 (14H, Ph$\underline{H}$—), 5.5-5.6 (3.52H, —C$\underline{H}$—), 3.5 (1.52H, Ch$\underline{H}$—), 1.9-2.0 (24H, Ph-C$\underline{H}_3$), 1.1-2.1 (15.2H, Ch$\underline{H}$—), 1.1 (4.56H, —C$\underline{H}_3$) | 38 |
| 30 | 130 | 7.8 (5.68H, —O$\underline{H}$), 6.1-6.5 (9H, Ph$\underline{H}$), 5.6 (3H, —C$\underline{H}$—), 5.0 (0.32H, —CH—), 3.5 (0.32H, ChH—), 1.9-2.0 (54H, Ph-C$\underline{H}_3$), 1.1-2.1 (3.2H, ChH—), 1.1 (0.96H, —CH$_3$) | 8 |

Synthesis Examples 31-40

Synthesis of Mixtures 131 to 140

Each of the mixtures 131 to 140 was prepared by mixing the compound A and compound B so that the introduction of acid-dissociating group described in Table 9 was obtained.

Synthesis Example 41

Synthesis of Compound 109

The compound 109 (compound B) was obtained in the same manner as in Synthesis Example 9 except for changing dry acetone to 1,3-dioxolane and shortening the reaction time to 12 h.

TABLE 9

(Praparation of Mixutuer)

| Synthesis Examples | Mixture Nos. | Polyphenol A | Compound B | Introduction of acid-dissociating group (%) |
|---|---|---|---|---|
| 31 | 131 | 102 | 122 | 15 |
| 32 | 132 | 103 | 124 | 10 |
| 33 | 133 | 105 | 126 | 5 |
| 34 | 134 | 108 | 128 | 10 |
| 35 | 135 | 110 | 129 | 20 |
| 36 | 136 | 107 | 122 | 15 |
| 37 | 137 | 102 | 111 | 15 |
| 38 | 138 | 102 | 112 | 13 |
| 39 | 139 | 108 | 119 | 8 |
| 40 | 140 | 108 | 119 | 15 |

Comparative Synthesis Example 1

A solution containing 1.14 g (5 mmol) of bisphenol A (Kanto Chemical Co., Inc.), 5 ml of dry acetone and 1.2 mg of dimethylaminopyridine was added dropwise with 2.62 g (12 mmol) of di-tert-butyldicarbonate over 10 min and stirred at 40° C. for 24 h. The reaction product solution was added to a large amount of water to precipitate the solid matter. The obtained white powder was washed with distilled water three times, filtered by suction, and dried under reduced pressure to obtain the aimed compound. The structure of the compound was determined by elemental analysis and $^1$H-NMR measurement (400 MHz, CDCl$_3$, TMS internal standard). The results are shown in Tables 10 and 11.

Comparative Synthesis Example 2

The aimed compound was synthesized in the same manner as in Comparative Synthesis Example 1 except for changing 1.14 g (5 mmol) of bisphenol A to 1.34 g (5 mmol) of bisphenol Z (Kanto Chemical Co., Inc.). The structure of each compound was determined by elemental analysis and $^1$H-NMR measurement (400 MHz, CDCl$_3$, TMS internal standard). The results are shown in Tables 10 and 11.

Comparative Synthesis Example 3

The aimed compound was synthesized in the same manner as in Comparative Synthesis Example 1 except for changing 1.14 g (5 mmol) of bisphenol A to 1.46 g (5 mmol) of tris(4-hydroxyphenyl)methane (Honshu Chemical Industry Co., Ltd.) and changing the amount of di-tert-butyldicarbonate used to 3.93 g (16 mmol). The structure of each compound was determined by elemental analysis and $^1$H-NMR measurement (400 MHz, CDCl$_3$, TMS internal standard). The results are shown in Tables 10 and 11.

Comparative Synthesis Example 4

The aimed compound was synthesized in the same manner as in Comparative Synthesis Example 1 except for changing 1.14 g (5 mmol) of bisphenol A to 1.77 g (5 mmol) of tris(4-hydroxyphenyl)benzene (Aldrich Chemical Co., Inc.) and changing the amount of di-tert-butyldicarbonate used to 3.93 g (16 mmol). The structure of each compound was determined by elemental analysis and 1H-NMR measurement (400 MHz, CDCl$_3$, TMS internal standard). The results are shown in Tables 10 and 11.

Comparative Synthesis Example 5

The aimed compound ("PHS-2 (205)") was synthesized in the same manner as in Comparative Synthesis Example 1 except for changing 1.14 g (5 mmol) of bisphenol A to 0.74 g (5 mmol) of polyhydroxystyrene having a weight average molecular weight of 8000 ("PHS-1" available from Aldrich Chemical Co., Inc.) and changing the amount of di-tert-butyldicarbonate used to 0.37 g (1.5 mmol). The t-butoxycarbonylation was 30% when measured by $^1$H-NMR (400 MHz, CDCl$_3$, TMS internal standard).

Comparative Synthesis Example 6

Synthesis of 1-(2-naphthyl)-1,1-bis(3-methyl-4-hydroxyphenyl)ethane

A mixture of 43.2 g (0.4 mol) of o-cresol and 17.1 g (0.1 mol) of β-acetonaphthone was made into a solution by heating at about 30° C. After adding 0.1 ml of sulfuric acid, 0.8 ml of 3-mercaptopropionic acid and 10 ml of toluene to the solution, the reaction was allowed to proceed under stirring. After confirming that the conversion reached 100% by a gas chromatographic analysis, 100 ml of toluene was added. The solid precipitated by cooling was filtered under reduced pressure, washed with a warm water of 60° C. under stirring, and purified by a silica gel column chromatography, to obtain 24 g of the title compound.

Comparative Synthesis Example 7

Synthesis of Compound 207

A solution containing 1.84 g (5 mmol)of 1-(2-naphthyl)-1,1-bis(3-methyl-4-hydroxyphenyl)ethane, 5 ml of dry acetone, 0.073 g (0.29 mmol) of pyridinium p-toluenesulfonate (Kanto Chemical Co., Inc.), and 0.43 g (6 mmol) of ethyl vinyl ether (Kanto Chemical Co., Inc.) was stirred at room temperature for 24 h. The reaction product solution was purified by a silica gel column chromatography (elute: ethyl acetate/hexane=1/3), to obtain the title compound. The structure of the compound was determined by elemental analysis and $^1$H-NMR measurement (400 MHz, CDCl$_3$, TMS internal standard). The results are shown in Tables 10 and 11.

Comparative Synthesis Example 8

Synthesis Compound 208

A solution containing 1.84 g (5 mmol) of 1-(2-naphthyl)-1,1-bis(3-methyl-4-hydroxyphenyl)ethane, 5 ml of dry acetone, 0.073 g (0.29 mmol) of pyridinium p-toluenesulfonate, and 0.76 g (6 mmol) of cyclohexyl vinyl ether was stirred at room temperature for 24 h. The reaction product solution was purified by a silica gel column chromatography (elute: ethyl acetate/hexane=1/3), to obtain the title compound. The structure of each compound was determined by elemental analysis and $^1$H-NMR measurement (400 MHz, CDCl$_3$, TMS internal standard). The results are shown in Tables 10 and 11.

TABLE 10

| Comparative Synthesis Examples | Compound Nos. | Empirical formula | | | Molecular weight | Calculated | | | Found | |
|---|---|---|---|---|---|---|---|---|---|---|
| | | C | H | O | | C | H | O | C | H |
| 1 | 201 | 25 | 32 | 6 | 428 | 70.07 | 7.53 | 22.40 | 70.0 | 7.6 |
| 2 | 202 | 28 | 36 | 6 | 468 | 71.77 | 7.74 | 20.49 | 71.7 | 7.6 |
| 3 | 203 | 34 | 40 | 9 | 592 | 68.97 | 6.80 | 24.30 | 69.2 | 6.7 |
| 4 | 204 | 39 | 42 | 9 | 654 | 71.54 | 6.47 | 21.99 | 71.7 | 6.3 |
| 6 | 206 | 26 | 24 | 2 | 368 | 84.75 | 6.57 | 8.68 | 84.7 | 6.5 |
| 7 | 207 | 30 | 32 | 3 | 440 | 81.78 | 7.32 | 10.89 | 81.7 | 7.3 |
| 8 | 208 | 34 | 38 | 3 | 494 | 82.55 | 7.74 | 9.70 | 82.7 | 7.6 |

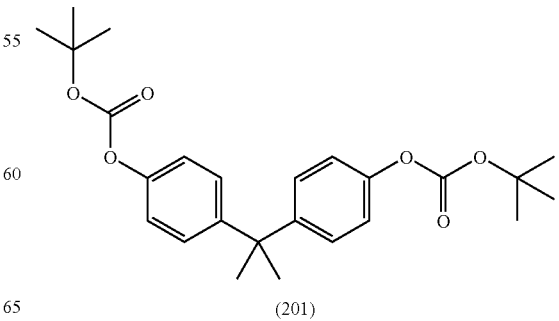

(201)

TABLE 10-continued
(Elemental Analysis)
| Comparative Synthesis Examples | Compound Nos. | Empirical formula | | | Molecular weight | Calculated | | | Found | |
|---|---|---|---|---|---|---|---|---|---|---|
| | | C | H | O | | C | H | O | C | H |
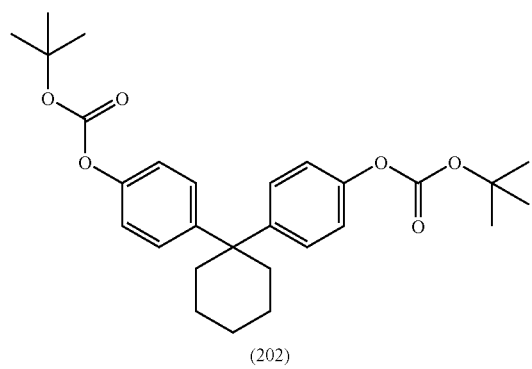
(202)
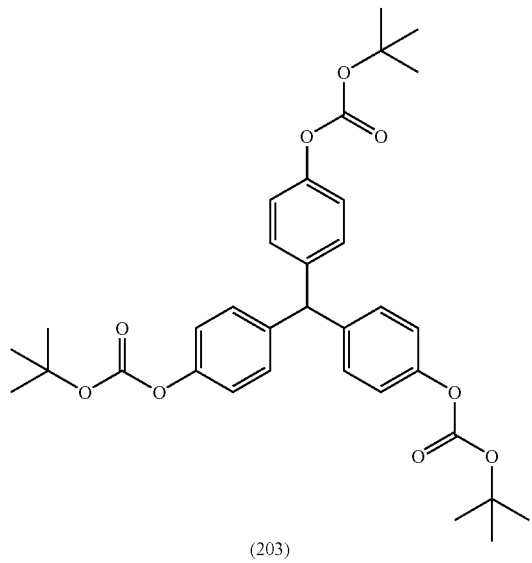
(203)
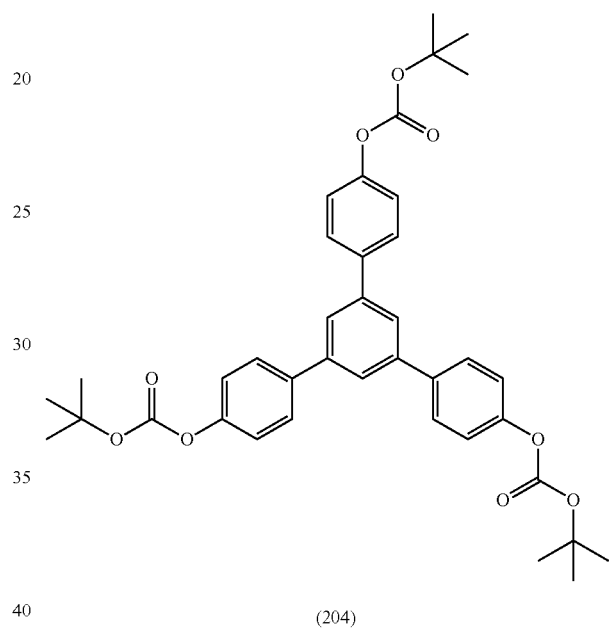
(204)
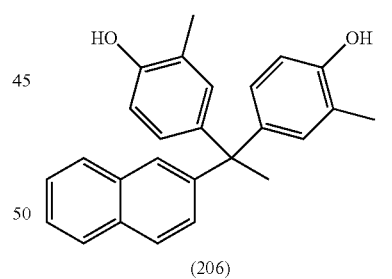
(206)
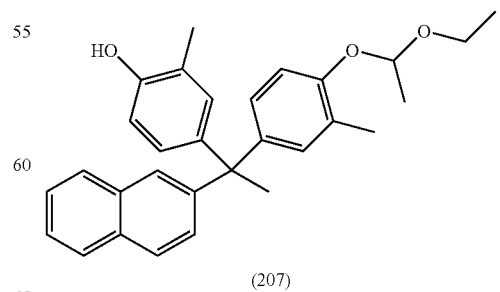
(207)

TABLE 10-continued (Elemental Analysis)

| Comparative Synthesis Examples | Compound Nos. | Empirical formula C H O | Molecular weight | Calculated C H O | Found C H |
|---|---|---|---|---|---|

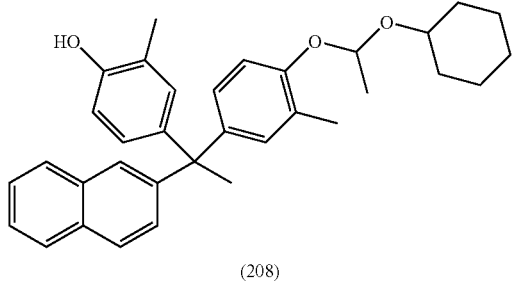

(208)

TABLE 11

(¹H-NMR)

| Comparative Synthesis Examples | Compound Nos. | ¹H-NMR |
|---|---|---|
| 1 | 201 | 7.3 (2H), 7.1 (2H), 2.2 (4H), 1.5 (18H) |
| 2 | 202 | 7.3 (2H), 7.1 (2H), 2.2 (4H), 2.2-1.5 (28H) |
| 3 | 203 | 7.3 (12H), 1.5 (27H) |
| 4 | 204 | 7.7 (9H), 7.3 (6H), 1.5 (27H) |
| 6 | 206 | 7.8-6.6 (13H), 5.5 (2H), 2.3-2.2 (9H) |
| 7 | 207 | 7.8-6.5 (13H), 5.4 (1H), 4.7 (1H), 3.7-3.4 (2H), 2.2 (9H), 2.1-1.8 (6H) |
| 8 | 208 | 7.8-6.6 (13H), 5.5 (1H), 3.5 (1H), 2.3-1.5 (22H) |

Examples 1-8 and Comparative Examples 1-3

The properties of the compounds synthesized in Synthesis Examples and Comparative Synthesis Examples, bisphenol fluorene (Osaka Gas Chemicals Co., Ltd.), and bisphenol anthraquinone (Honshu Chemical Industry Co., Ltd.) were evaluated. The results are shown in Table 12.

TABLE 12

| Compound Nos. | Glass transition temperature ° C. | Rating | Crystallization temperature ° C. |
|---|---|---|---|
| Examples | | | |
| 1 | 101 | 144 | A | not detected |
| 2 | 102 | 136 | A | not detected |
| 3 | 103 | 116 | C | 190 |
| 4 | 104 | 145 | A | 287 |
| 5 | 105 | 156 | A | not detected |
| 6 | 106 | 137 | A | not detected |
| 7 | 107 | 147 | A | not detected |
| 8 | 108 | 125 | A | not detected |
| Comparative Examples | | | |
| 1 | 206 | 72 | C | not detected |
| 2 | 209 | 101 | C | 157.7 |
| 3 | 210 | 119 | C | 162.3 |

TABLE 12-continued

| | Glass transition temperature- Crystallization temperature | Residual metal | Alkali dissolving speed |
|---|---|---|---|
| Examples | | | |
| 1 | A | A | A |
| 2 | A | A | A |
| 3 | A | A | A |
| 4 | A | A | A |
| 5 | A | A | A |
| 6 | A | A | A |
| 7 | A | A | A |
| 8 | A | A | A |
| Comparative Examples | | | |
| 1 | A | A | A |
| 2 | C | A | A |
| 3 | C | A | A |

TABLE 12-continued

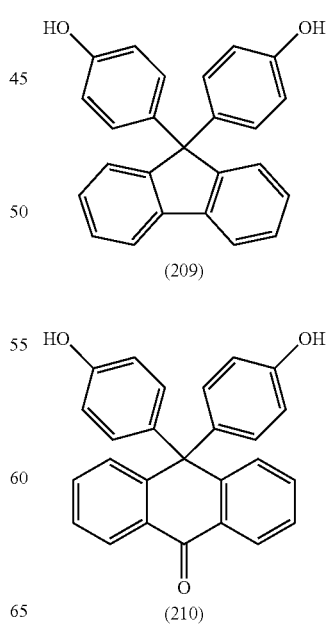

(209)

(210)

Examples 51-82 and Comparative Examples 51-57

The properties of the compounds and mixtures obtained in Synthesis Examples and Comparative Synthesis Examples were evaluated. The results are shown in Table 13.

TABLE 13

| | Compound or mixture | Solubility to safety solvent | film-forming property | Prevention of dissolution to alkali | Adhesion to silicon substrate |
|---|---|---|---|---|---|
| Examples | | | | | |
| 51 | 109 | A | A | A | A |
| 52 | 110 | A | A | A | A |
| 53 | 111 | A | A | A | A |
| 54 | 112 | A | A | A | A |
| 55 | 113 | A | A | A | A |
| 56 | 114 | A | A | A | A |
| 57 | 115 | A | A | A | A |
| 58 | 116 | A | A | A | A |
| 59 | 117 | A | A | A | A |
| 60 | 118 | A | A | A | A |
| 61 | 119 | A | A | A | A |
| 62 | 120 | A | A | A | A |
| 63 | 121 | A | A | A | A |
| 64 | 122 | A | A | A | A |
| 65 | 123 | A | A | A | A |
| 66 | 124 | A | A | A | A |
| 67 | 125 | A | A | A | A |
| 68 | 126 | A | A | A | A |
| 69 | 127 | A | A | A | A |
| 70 | 128 | A | A | A | A |
| 71 | 129 | A | A | A | A |
| 72 | 130 | A | A | A | A |
| 73 | 131 | A | A | A | A |
| 74 | 132 | A | A | A | A |
| 75 | 133 | A | A | A | A |
| 76 | 134 | A | A | A | A |
| 77 | 135 | A | A | A | A |
| 78 | 136 | A | A | A | A |
| 79 | 137 | A | A | A | A |
| 80 | 138 | A | A | A | A |
| 81 | 139 | A | A | A | A |
| 82 | 140 | A | A | A | A |
| Comparative Examples | | | | | |
| 51 | 201 | C | — | — | — |
| 52 | 202 | C | — | — | — |
| 53 | 203 | C | A | A | A |
| 54 | 204 | A | B | A | A |
| 55 | 205 | A | A | A | A |
| 56 | 207 | A | A | A | A |
| 57 | 208 | A | A | A | A |

Examples 101-142 and Comparative Examples 101-104

Evaluation of Resist Patterns

Each radiation-sensitive composition was prepared by filtering a mixture of the compound or mixture obtained in Synthesis Examples 1-32 and a component listed in Table 14 through a 0.1-μm Teflon (trademark) filter. The resolution and sensitivity of resist patterns made from each radiation-sensitive composition were evaluated. The results are shown in Table 15. The amount of outgas generated upon the exposure to light was small in any of Examples. The change of film thickness after irradiation with an exposure twice as much as the optimum exposure was less than 5 nm in any of Examples.

TABLE 14

| | Compound or mixture (g) | Resin (g) | Acid generator (g) | Acid-diffusion controller (g) | Solvent (g) | Surfactant (g) |
|---|---|---|---|---|---|---|
| Examples | | | | | | |
| 101 | 109 (0.5) | — | PAG-1 (0.05) | Q-1 (0.005) | S-3/S-4 (3.2/6.3) | — |
| 102 | 110 (0.5) | — | PAG-1 (0.1) | Q-1 (0.01) | S-3/S-4 (3.2/6.3) | — |
| 103 | 111 (0.5) | — | PAG-1 (0.1) | Q-1 (0.01) | S-3/S-4 (3.2/6.3) | — |
| 104 | 112 (0.5) | — | PAG-1 (0.1) | Q-1 (0.01) | S-3/S-4 (3.2/6.3) | — |
| 105 | 113 (0.5) | — | PAG-1 (0.1) | Q-1 (0.01) | S-3/S-4 (3.2/6.3) | — |
| 106 | 114 (0.5) | — | PAG-1 (0.1) | Q-1 (0.01) | S-3/S-4 (3.2/6.3) | — |
| 107 | 115 (0.5) | — | PAG-1 (0.1) | Q-1 (0.01) | S-3/S-4 (3.2/6.3) | — |
| 108 | 116 (0.5) | — | PAG-1 (0.1) | Q-1 (0.01) | S-3/S-4 (3.2/6.3) | — |
| 109 | 117 (0.5) | — | PAG-1 (0.1) | Q-1 (0.01) | S-3/S-4 (3.2/6.3) | — |
| 110 | 118 (0.5) | — | PAG-1 (0.1) | Q-1 (0.01) | S-3/S-4 (3.2/6.3) | — |
| 111 | 119 (0.5) | — | PAG-1 (0.1) | Q-1 (0.01) | S-3/S-4 (3.2/6.3) | — |
| 112 | 120 (0.5) | — | PAG-1 (0.05) | Q-1 (0.005) | S-3/S-4 (3.2/6.3) | — |
| 113 | 121 (0.5) | — | PAG-1 (0.1) | Q-1 (0.01) | S-3/S-4 (3.2/6.3) | — |
| 114 | 122 (0.5) | — | PAG-1 (0.1) | Q-1 (0.01) | S-3/S-4 (3.2/6.3) | — |

TABLE 14-continued

| | Compound or mixture (g) | Resin (g) | Acid generator (g) | Acid-diffusion controller (g) | Solvent (g) | Surfactant (g) |
|---|---|---|---|---|---|---|
| 115 | 123 (0.5) | — | PAG-1 (0.1) | Q-1 (0.01) | S-3/S-4 (3.2/6.3) | — |
| 116 | 124 (0.5) | — | PAG-1 (0.1) | Q-1 (0.01) | S-3/S-4 (3.2/6.3) | — |
| 117 | 125 (0.5) | — | PAG-1 (0.1) | Q-1 (0.01) | S-3/S-4 (3.2/6.3) | — |
| 118 | 126 (0.5) | — | PAG-1 (0.1) | Q-1 (0.01) | S-3/S-4 (3.2/6.3) | — |
| 119 | 127 (0.5) | — | PAG-1 (0.1) | Q-1 (0.01) | S-3/S-4 (3.2/6.3) | — |
| 120 | 128 (0.5) | — | PAG-1 (0.1) | Q-1 (0.01) | S-3/S-4 (3.2/6.3) | — |
| 121 | 129 (0.5) | — | PAG-1 (0.1) | Q-1 (0.01) | S-3/S-4 (3.2/6.3) | — |
| 122 | 130 (0.5) | — | PAG-1 (0.1) | Q-1 (0.01) | S-3/S-4 (3.2/6.3) | — |
| 123 | 131 (0.5) | — | PAG-1 (0.1) | Q-1 (0.01) | S-3/S-4 (3.2/6.3) | — |
| 124 | 132 (0.5) | — | PAG-1 (0.1) | Q-1 (0.01) | S-3/S-4 (3.2/6.3) | — |
| 125 | 133 (0.5) | — | PAG-1 (0.1) | Q-1 (0.01) | S-3/S-4 (3.2/6.3) | — |
| 126 | 134 (0.5) | — | PAG-1 (0.1) | Q-1 (0.01) | S-3/S-4 (3.2/6.3) | — |
| 127 | 135 (0.5) | — | PAG-1 (0.1) | Q-1 (0.01) | S-3/S-4 (3.2/6.3) | — |
| 128 | 136 (0.5) | — | PAG-1 (0.1) | Q-1 (0.01) | S-3/S-4 (3.2/6.3) | — |
| 129 | 137 (0.5) | — | PAG-1 (0.1) | Q-1 (0.01) | S-3/S-4 (3.2/6.3) | — |
| 130 | 138 (0.5) | — | PAG-1 (0.1) | Q-1 (0.01) | S-3/S-4 (3.2/6.3) | — |
| 131 | 139 (0.5) | — | PAG-1 (0.1) | Q-1 (0.01) | S-3/S-4 (3.2/6.3) | — |
| 132 | 140 (0.5) | — | PAG-3 (0.15) | Q-3 (0.015) | S-3/S-4 (3.2/6.3) | D-1 (0.0015) |
| 133 | 124 (0.5) | — | PAG-1 (0.15) | Q-1 (0.015) | S-3/S-4 (3.2/6.3) | — |
| 134 | 124 (0.5) | — | PAG-4 (0.15) | Q-1 (0.015) | S-3/S-4 (3.2/6.3) | — |
| 135 | 124 (0.5) | — | PAG-5 (0.15) | Q-1 (0.015) | S-3/S-4 (3.2/6.3) | — |
| 136 | 124 (0.5) | — | PAG-6 (0.15) | Q-1 (0.015) | S-3/S-4 (3.2/6.3) | — |
| 137 | 124 (0.5) | — | PAG-3 (0.15) | Q-1 (0.015) | S-3/S-4 (3.2/6.3) | — |
| 138 | 124 (0.5) | — | PAG-3 (0.15) | Q-4 (0.015) | S-3/S-4 (3.2/6.3) | — |
| 139 | 124 (0.5) | — | PAG-3 (0.15) | Q-5 (0.015) | S-3/S-4 (3.2/6.3) | — |
| 140 | 124 (0.5) | — | PAG-3 (0.15) | Q-3 (0.015) | S-3/S-4 (3.2/6.3) | — |
| 141 | 124 (0.5) | 105 (0.3) | PAG-1 (0.1) | Q-1 (0.01) | S-3/S-4 (3.2/6.3) | — |
| 142 | 124 (0.5) | 105 (0.6) | PAG-1 (0.1) | Q-1 (0.01) | S-3/S-4 (3.2/6.3) | — |
| Comparative Examples | | | | | | |
| 101 | 203 (0.5) | — | PAG-1 (0.05) | Q-1 (0.005) | S-1/S-2 (1.3/3.2) | — |
| 102 | 203 (0.5) | — | PAG-2 (0.05) | Q-2 (0.005) | S-1/S-2 (1.3/3.2) | — |
| 103 | 208 (0.5) | — | PAG-2 (0.05) | Q-2 (0.005) | S-1/S-2 (1.3/3.2) | — |
| 104 | 208 (0.5) | 105 (0.3) | PAG-2 (0.05) | Q-2 (0.005) | S-1/S-2 (1.3/3.2) | — |

PAG-1: diphenyltolylsulfonium nonafluorobutanesulfonate
PAG-2: triphenylsulfonium trifluoromethanesulfonate
PAG-3: triphenylsulfonium p-toluenesulfonate
PAG-4: triphenylsulfonium p-trifluoromethylbenzenesulfonate
PAG-5: triphenylsulfonium p-perfluorobenzenesulfonate
PAG-6: triphenylsulfonium perfluorooctanesulfonate
Q-1: trioctylamine
Q-2: diazabicyclooctane TABLE 14-continued

| | Compound or mixture (g) | Resin (g) | Acid generator (g) | Acid-diffusion controller (g) | Solvent (g) | Surfactant (g) |
|---|---|---|---|---|---|---|

Q-3: triphenylimidazole
Q-4: m-xylenediamine
Q-5: terpyridine
S-1: PGMEA
S-2: EL
S-3: EP
S-4: PGME
D-1: Megaface R08 (Dainippon Ink & Chemicals, Inc.)

TABLE 15

| | PEB (° C.) | Sensitivity (μC/cm$^2$) | Resolution (nm) | LER (3σ) (nm) |
|---|---|---|---|---|
| Examples | | | | |
| 101 | 110 | 10 | 50 | 4.3 |
| 102 | 110 | 10 | 45 | 4.2 |
| 103 | 110 | 10 | 45 | 4.3 |
| 104 | 110 | 10 | 40 | 4.2 |
| 105 | 110 | 10 | 40 | 4.2 |
| 106 | 60 | 10 | 40 | 4.5 |
| 107 | 110 | 10 | 45 | 4.5 |
| 108 | 110 | 10 | 45 | 4.6 |
| 109 | 110 | 20 | 50 | 4.4 |
| 110 | 90 | 10 | 45 | 4.5 |
| 111 | 110 | 10 | 40 | 4.5 |
| 112 | 110 | 20 | 50 | 4.8 |
| 113 | 110 | 10 | 45 | 4.9 |
| 114 | 110 | 20 | 45 | 4.8 |
| 115 | 110 | 10 | 40 | 4.8 |
| 116 | 110 | 10 | 40 | 4.9 |
| 117 | 60 | 13 | 40 | 4.8 |
| 118 | 110 | 13 | 45 | 4.7 |
| 119 | 110 | 13 | 45 | 4.8 |
| 120 | 110 | 20 | 50 | 4.9 |
| 121 | 90 | 13 | 45 | 4.8 |
| 122 | 110 | 10 | 40 | 4.8 |
| 123 | 110 | 8 | 40 | 4.8 |
| 124 | 110 | 10 | 40 | 4.8 |
| 125 | 60 | 8 | 40 | 4.9 |
| 126 | 110 | 20 | 50 | 4.8 |
| 127 | 90 | 8 | 45 | 4.9 |
| 128 | 110 | 13 | 45 | 4.9 |
| 129 | 110 | 10 | 45 | 4.6 |
| 130 | 110 | 10 | 40 | 4.6 |
| 131 | 110 | 20 | 50 | 4.8 |
| 132 | 110 | 5 | 35 | 3.5 |
| 133 | 110 | 8 | 35 | 4.8 |
| 134 | 110 | 8 | 35 | 4.8 |
| 135 | 110 | 8 | 35 | 4.8 |
| 136 | 110 | 8 | 35 | 4.8 |
| 137 | 110 | 8 | 35 | 4.4 |
| 138 | 110 | 8 | 35 | 4.4 |
| 139 | 110 | 8 | 35 | 4.4 |
| 140 | 110 | 8 | 35 | 3.6 |
| 141 | 110 | 10 | 35 | 5.2 |
| 142 | 110 | 20 | 80 | 6.2 |
| Comparative Examples | | | | |
| 101 | 80 | 60 | 100 | 7.1 |
| 102 | 80 | 60 | 100 | 7.3 |
| 103 | 80 | 10 | 50 | 7.1 |
| 104 | 80 | 20 | 80 | 8.8 |

Examples 201-212

Dry Etching Resistance

Each of the radiation-sensitive compositions of Examples 101-111 and 138 was applied on a silicon wafer substrate to form a resist film with a film thickness of 100 nm. The dry etching with tetrafluoromethane (etching gas) was conducted using RIE etching machine under the conditions of 70 sccm, 50 W, and 20 Pa. The etching rate was less than 200 Å/min in any of the resist films, to show a high etching resistance.

Comparative Example 201

The composition of Comparative Example 205 was applied on a silicon wafer substrate to form a resist film with a film thickness of 100 nm. The dry etching was conducted in the same manner as in Example 201. The etching rate was 200 Å/min, to show a lower etching resistance than that of the resist films made of the radiation-sensitive composition of the present invention.

Example 251

Ultraviolet-Visible Absorption Spectra

From the ultraviolet-visible absorption spectra of a 0.01 g/L methanol solution of each of Compounds 103, 105 and 108 measured by an autographic spectrophotometer "UV-3100PC" manufactured by Shimadzu Corporation, the absorptivity coefficient at 248 nm of each compound was determined. The absorptivity coefficient was 43.4 L/(cm·g) for Compound 103, 47.4 L/(cm·g) for Compound 105, and 16.9 L/(cm·g) for Compound 108. The absorptivity coefficient is sufficiently larger than 15 L/(cm·g) in any of the compounds, to indicate that the compounds, particularly Compounds 103 and 105, are useful as the raw material of the compound B for forming shade masks. The compounds B produced from these compounds and the radiation-sensitive composition containing such compounds B also have a high absorptivity and are useful for forming shade masks.

Comparative Example 251

From the ultraviolet-visible absorption spectra of a 0.01 g/L methanol solution of poly(4-vinylphenol) (Mw=8000, available from Aldrich Chemical Co., Inc.) measured in the same manner as in Example 251, the absorptivity coefficient at 248 nm was determined. The absorptivity coefficient was 1.7 L/(cm·g). Since the absorptivity coefficient is far smaller than 15 L/(cm·g), poly(4-vinylphenol) is not applicable to the raw material of the compound B for forming shade masks.

INDUSTRIAL APPLICABILITY

The compound B of the present invention and the radiation-sensitive composition are highly sensitive to radiations such as KrF excimer lasers, extreme ultraviolet rays, electron beams and X-rays, to provide resist patterns with a high resolution. Therefore, the present invention enables the production of highly integrated semiconductor devices with a high productivity.

What is claimed is:

1. A radiation-sensitive composition containing 1 to 80% by weight of a solid component and 20 to 99% by weight of a solvent, wherein the radiation sensitive composition contains a compound B which satisfies the following requirements of:
   (a) having a structure derived from a polyphenol compound A by introducing an acid-dissociating group to at least one phenolic hydroxyl group of the polyphenol compound A which is synthesized by a condensation between a di- to tetrafunctional aromatic ketone or aromatic aldehyde each having 5 to 36 carbon atoms with a compound having 1 to 3 phenolic hydroxyl groups and 6 to 15 carbon atoms, and
   (b) having a molecular weight of 400 to 2000,
   wherein a total content of the compound B and a solubilizer C is 50 to 99.999% by weight of a total weight of the solid component,
   wherein the solubilizer C is the same compound as the polyphenol compound A which is used to produce the compound B, and
   wherein the solid component further comprises at least one acid generator which generates acid upon exposure to KrF excimer lasers, extreme ultraviolet rays, electron beams or X rays.

2. The radiation-sensitive composition according to claim 1, wherein the compound B has a conjugated structure which is formed by at least two benzene rings and/or nonbonding electron pair of hetero atom.

3. The radiation-sensitive composition according to claim 1, wherein the aromatic ketone or aromatic aldehyde is trifunctional or tetrafunctional.

4. The radiation-sensitive composition according to claim 2, wherein the conjugated structure is at least one structure selected from the group consisting of biphenyl structure, naphthalene structure, terphenyl structure, anthracene structure, phenanthrene structure, pyrene structure, fluorene structure, acenaphthene structure, 1-ketoacenaphthene structure, benzophenone structure, xanthene structure, anthraquinone structure, and thioxanthene structure.

5. The radiation-sensitive composition according claim 1, wherein the aromatic ketone or aromatic aldehyde has at least one structure selected from the group consisting of biphenyl structure, naphthalene structure, terphenyl structure, anthracene structure, phenanthrene structure, pyrene structure, fluorene structure, acenaphthene structure, 1-ketoacenaphthene structure, benzophenone structure, xanthene structure, anthraquinone structure, and thioxanthene structure.

6. The radiation-sensitive composition according to claim 5, wherein the aromatic ketone or aromatic aldehyde has a naphthalene structure having 10 to 20 carbon atoms.

7. The radiation-sensitive composition according to claim 5, wherein the aromatic ketone or aromatic aldehyde has a terphenyl structure having 18 to 28 carbon atoms.

8. The radiation-sensitive composition according to claim 1, wherein the compound B is represented by the following formula 1:

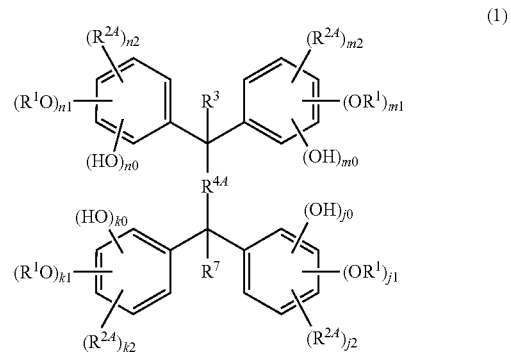

(1)

wherein
each $R^1$ is an acid-dissociating group selected from the group consisting of substituted methyl groups, 1-substituted ethyl groups, 1-substituted n-propyl groups, 1-branched alkyl groups, silyl groups, acyl groups, 1-substituted alkoxymethyl groups, cyclic ether groups and alkoxycarbonyl groups, and two or more R' may be the same or different;
each $R^{2A}$ is group selected from the group consisting of halogen atom, alkyl group, cycloalkyl group, aryl group, aralkyl group, alkoxy group, aryloxy group, alkenyl group, acyl group, alkoxycarbonyl group, alkyloyloxy group, aryloyloxy group, cyano group, and nitro group, and two or more $R^{2A}$ may be the same or different;
each of $R^3$ and $R^7$ is a hydrogen atom or alkyl group having 1 to 6 carbon atoms;
$R^{4A}$ is a divalent group having 10 to 28 carbon atoms which includes a biphenyl structure, terphenyl structure, naphthalene structure, phenanthrene structure, or pyrene structure, or $R^{4A}$ together with $R^3$ and $R^7$ optionally represents a tetravalent group having 10 to 28 carbon atoms which includes a fluorene structure or benzophenone structure; and
each of k0, j0, m0, and n0 is an integer of 0 to 3 each of k1, j1, m1, and n1 is an integer of 0 to 3; and each of k2, j2, m2, and n2 is an integer of 0 to 4, satisfying $1 \leq k0+k1+k2 \leq 5$, $1 \leq j0+j1+j2 \leq 5$, $1 \leq m0+m1+m2 \leq 5$, $1 \leq n0+n1+n2 \leq 5$, $1 \leq k1+j1+m1+n1 \leq 12$, $1 \leq k0+k1 \leq 3$, $1 \leq j0+j1 \leq 3$, $1 \leq m0+m1 \leq 3$, and $1 \leq n0+n1 \leq 3$.

9. The radiation-sensitive composition according to claim 8, wherein the compound B is represented by the following formula 7-1:

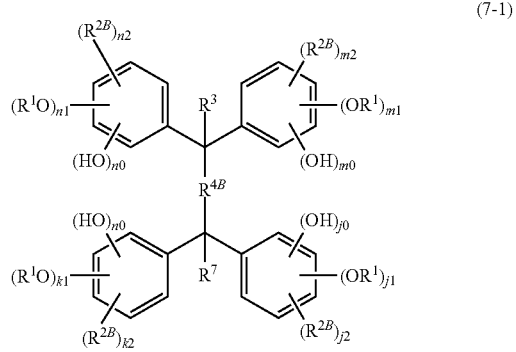

(7-1)

wherein $R^1$, $R^3$, $R^7$, k0, j0, m0, n0, k1, j1, m1, n1, k2, j2, m2, and n2 are the same as defined above; each $R^{2B}$ is a group selected from the group consisting of halogen atom, alkyl group, aryl group, aralkyl group, alkoxy group, alkenyl group, acyl group, alkoxycarbonyl group, alkyloyloxy group, aryloyloxy group, cyano group and nitro group, and two or more $R^{2B}$ may be the same or different; and $R^{4B}$ is a divalent group having 10 to 20 carbon atoms which includes a naphthalene structure.

10. The radiation-sensitive composition according to claim 8, wherein the compound B is represented by the following formula 7-2:

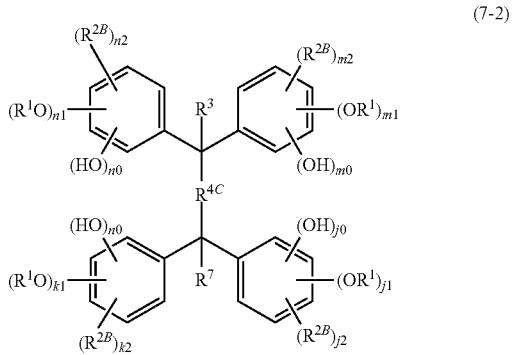

(7-2)

wherein $R^1$, $R^3$, $R^7$, k0, j0, m0, n0, k1, j1, m1, n1, k2, j2, m2, and n2 are the same as defined above; each $R^{2B}$ is a group selected from the group consisting of halogen atom, alkyl group, aryl group, aralkyl group, alkoxy group, alkenyl group, acyl group, alkoxycarbonyl group, alkyloyloxy group, aryloyloxy group, cyano group, and nitro group, and two or more $R^{2B}$ may be the same or different; and $R^{4C}$ is a divalent group having 18 to 28 carbon atoms which includes a terphenyl structure.

11. The radiation-sensitive composition according to claim 9, wherein the compound B is represented by the following formula 9-1:

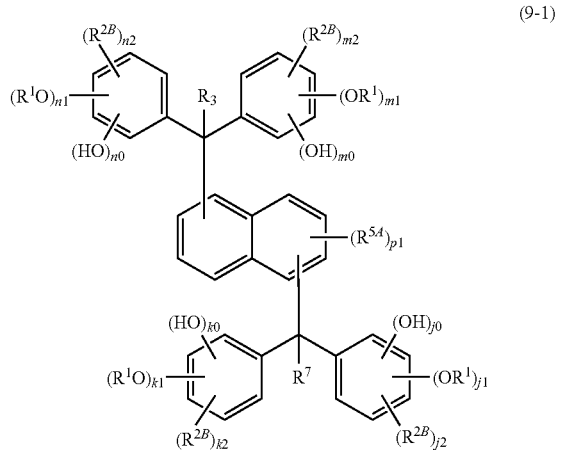

(9-1)

wherein $R^1$, $R^{2B}$, $R^3$, $R^7$, k0, j0, m0, n0, k1, j1, m1, n1, k2, j2, m2, and n2 is the same as defined above; each $R^{5A}$ is independently a group selected from the group consisting of alkyl groups having 1 to 10 carbon atoms, cycloalkyl groups having 3 to 10 carbon atoms and aryl groups having 6 to 10 carbon atoms, and two or more $R^{5A}$ may be the same or different; and p1 is an integer of 0 to 6.

12. The radiation-sensitive composition according to claim 11, wherein the compound B is represented by the following formula 9-2:

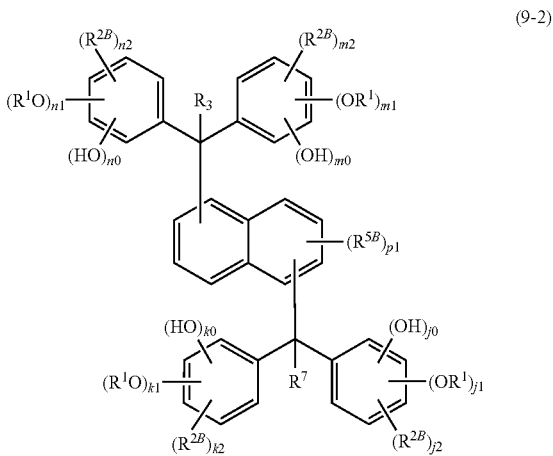

(9-2)

wherein $R^1$, $R^{2B}$, $R^3$, $R^7$, p1, k0, j0, m0, n0, k1, j1, m1, n1, k2, j2, m2, and n2 are the same as defined above; and each $R^{5B}$ is an alkyl group having 1 to 6 carbon atoms, and two or more $R^{5B}$ may be the same or different.

13. The radiation-sensitive composition according to claim 10, wherein the compound B is represented by the following formula 18-1:

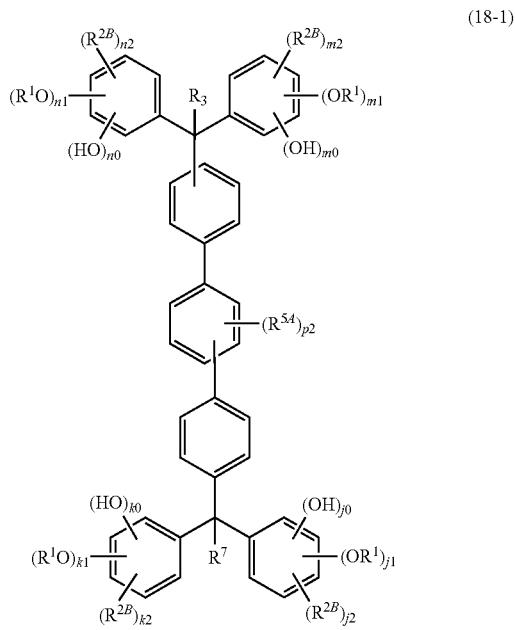

(18-1)

wherein $R^1$, $R^{2B}$, $R^3$, $R^7$, k0, j0, m0, n0, k1, j1, m1, n1, k2, j2, m2, and n2 are the same as defined above; each $R^{5A}$ is a group selected from the group consisting of alkyl groups having 1 to 10 carbon atoms, cycloalkyl groups having 3 to 10 carbon atoms and aryl groups having 6 to 10 carbon atoms, and two or more $R^{5A}$ may be the same or different; and p2 is an integer of 0 to 2.

14. The radiation-sensitive composition according to claim 13, wherein the compound B is represented by the following formula 18-2:

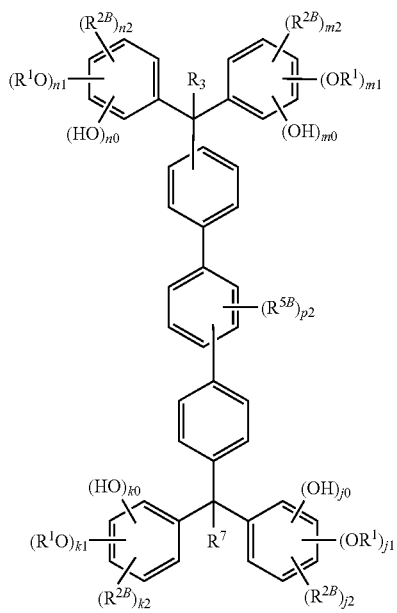

(18-2)

wherein $R^1$, $R^{2B}$, $R^3$, $R^{5B}$, $R^7$, p2, k0, j0, m0, n0, k1, j1, m1, n1, k2, j2, m2, and n2 are the same as defined above; and each $R^{5B}$ is an alkyl group having 1 to 6 carbon atoms, and two or more $R^{5B}$ may be the same or different.

15. The radiation-sensitive composition according to claim 8, wherein the compound B is at least one compound selected from the compounds represented by the following formulae 25-1 to 25-10:

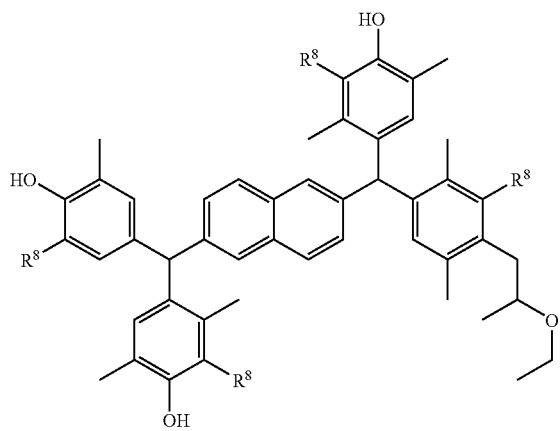

(25-1)

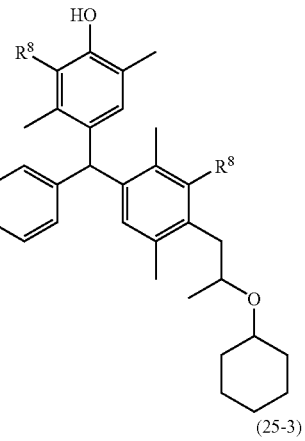

(25-2)

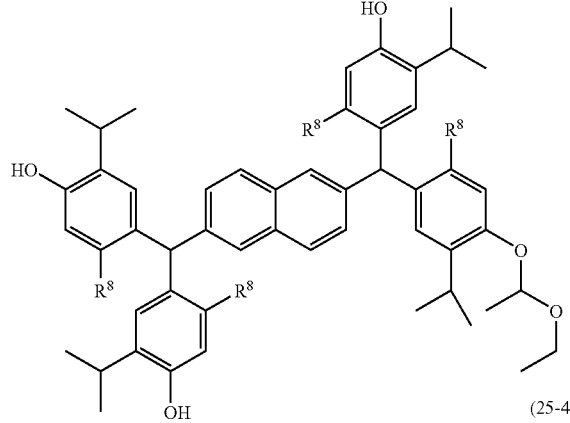

(25-3)

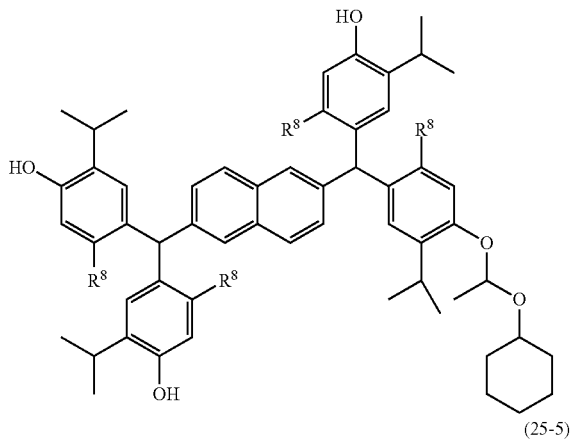

(25-4)

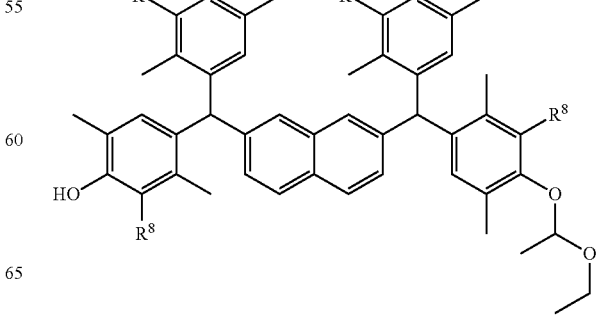

(25-5)

(25-6)
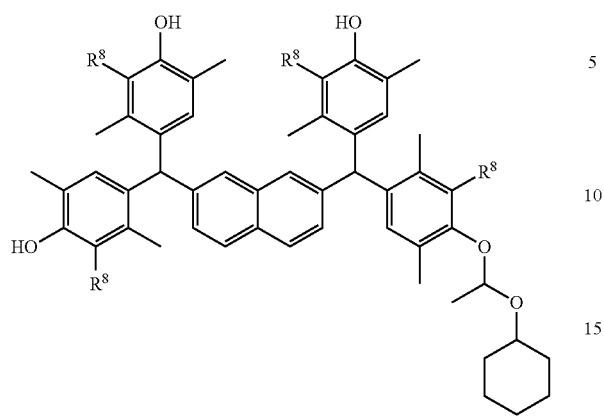
(25-7)
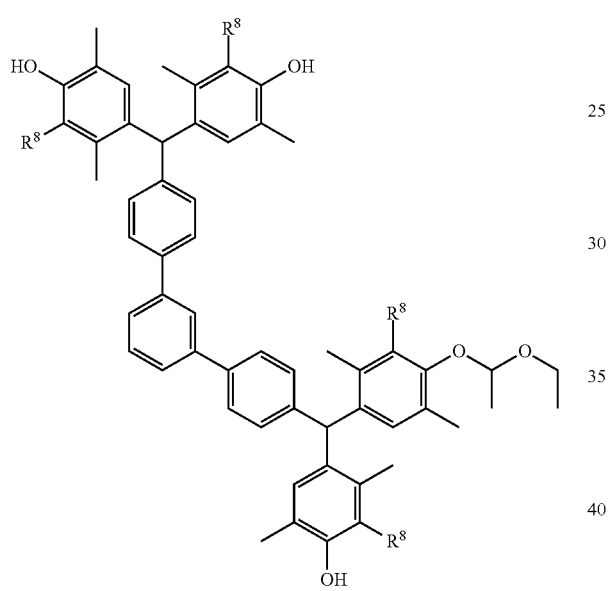
(25-8)
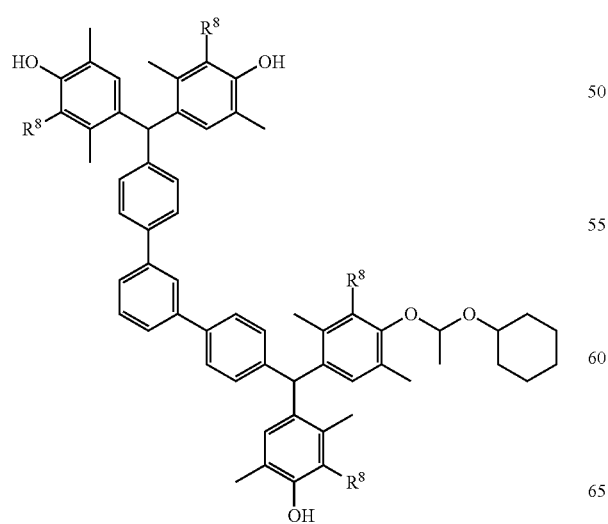
(25-9)
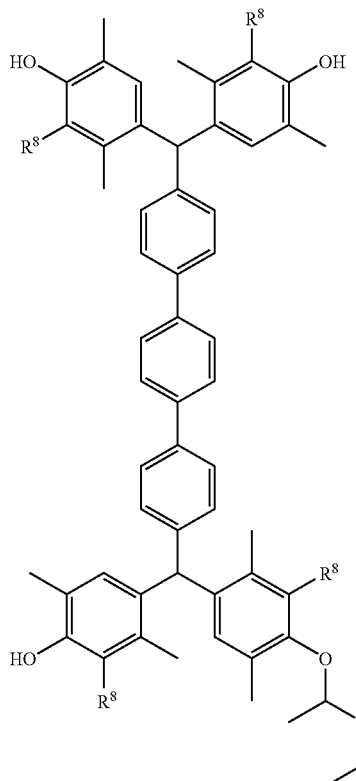
(25-10)
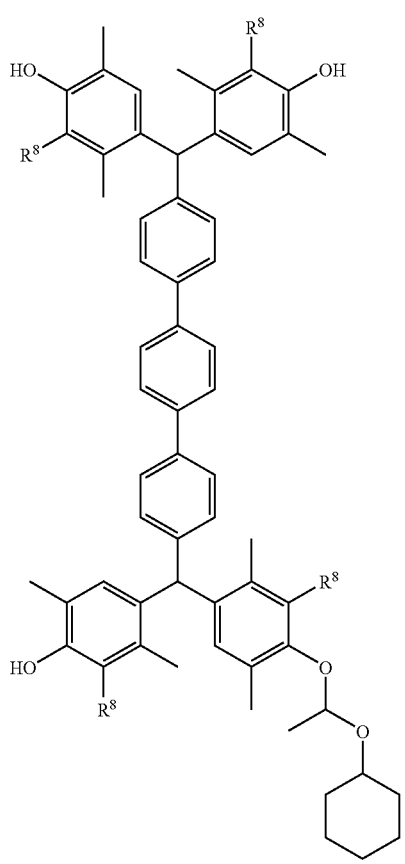

wherein each $R^8$ is a hydrogen atom or methyl group, and two or more $R^8$ may be the same or different in respective formulae.

16. The radiation-sensitive composition according to claim 1, wherein the compound B is represented by the following formula 28:

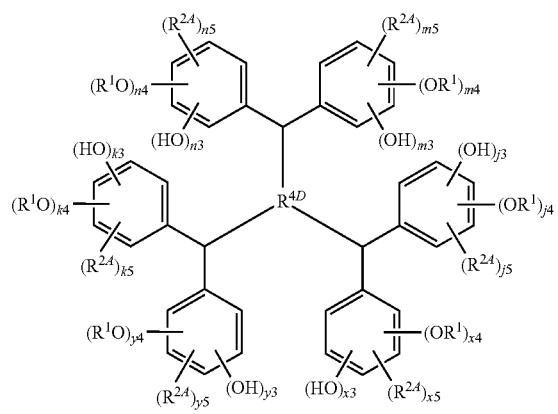

(28)

wherein
each $R^1$ is an acid-dissociating group selected from the group consisting of substituted methyl groups, 1-substituted ethyl groups, 1-substituted n-propyl groups, 1-branched alkyl groups, silyl groups, acyl groups, 1-substituted alkoxymethyl groups, cyclic ether groups and alkoxycarbonyl groups, and two or more $R^1$ may be the same or different;

each $R^{2A}$ is a group selected from the group consisting of halogen atom, alkyl group, cycloalkyl group, aryl group, aralkyl group, alkoxy group, aryloxy group, alkenyl group, acyl group, alkoxycarbonyl group, alkyloyloxy group, aryloyloxy group, cyano group, and nitro group, and two or more $R^{2A}$ may be the same or different;

$R^{4D}$ is a trivalent group having 6 to 20 carbon atoms which includes a benzene structure, naphthalene structure, terphenyl structure or phenanthrene structure;

each of k3, j3, m3, n3, x3, and y3 is an integer of 0 to 3; each of k4, j4, m4, n4, x4, and y4 is an integer of 0 to 3; and each of k5, j5, m5, n5, x5, and y5 is an integer of 0 to 4, satisfying $1 \leq k3+k4+k5 \leq 5$, $1 \leq j3+j4+j5 \leq 5$, $1 \leq m3+m4+m5 \leq 5$, $1 \leq n3+n4+n5 \leq 5$, $1 \leq x3+x4+x5 \leq 5$, $1 \leq y3+y4+y5 \leq 5$, $1 \leq k4+j4+m4+n4+x4+y4 \leq 18$, $1 \leq k3=K4 \leq 3$, $1 \leq j3+j4 \leq 3$, $1 \leq m3+m4 \leq 3$, $1 \leq n3+n4 \leq 3$, $1 \leq x3+x4 \leq 3$, and $1 \leq y3+y4 \leq 3$.

17. The radiation-sensitive composition according to claim 16, wherein the compound B is represented by the following formula 29:

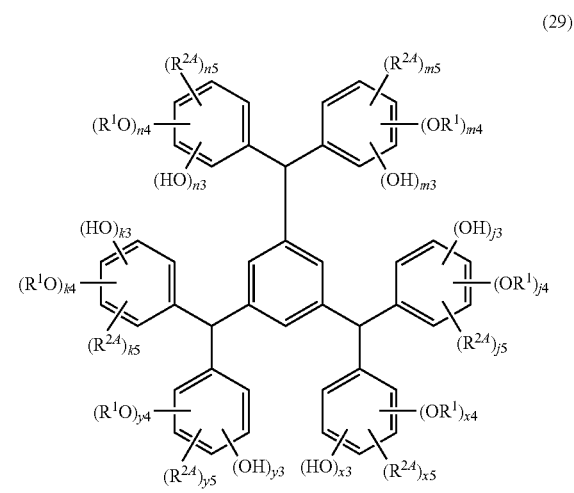

(29)

wherein $R^1$, $R^{2A}$, k3, j3, m3, n3, x3, y3, k4, j4, m4, n4, x4, y4, k5, j5, m5, n5, x5, and y5 are the same as defined above.

18. The radiation-sensitive composition according to claim 17, wherein the compound B is represented by the following formula 30-1:

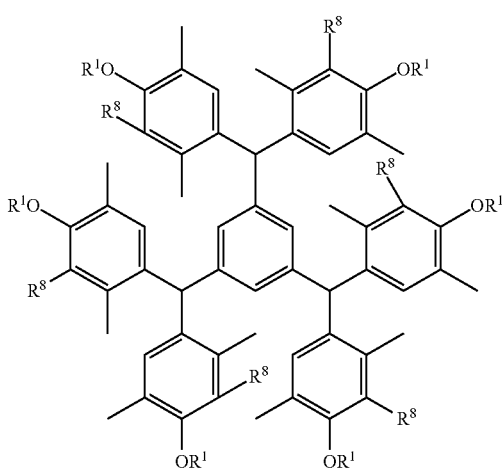

(30-1)

wherein each $R^8$ is a hydrogen atom or methyl group, and two or more $R^8$ may be the same or different.

19. The radiation-sensitive composition according to claim 17, wherein the compound B is selected from the compounds represented by the following formulae 31-1 to 31-3:

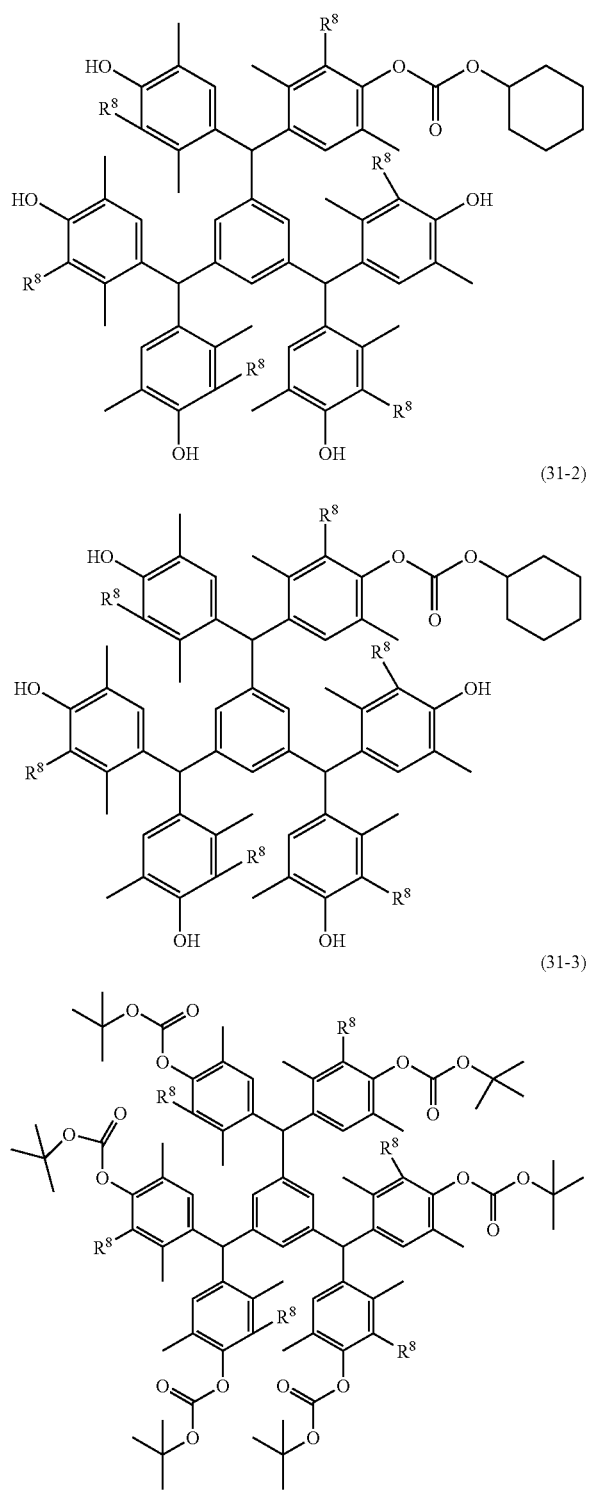

wherein each $R^8$ is a hydrogen atom or methyl group, and two or more $R^8$ may be the same or different in respective formulae.

20. The radiation-sensitive composition according to claim 1, wherein the compound having the phenolic hydroxyl group is selected from the group consisting of 2,5-xylenol, thymol and 2,3,6-trimethylphenol.

21. The radiation-sensitive composition according to claim 1, wherein the compound having the phenolic hydroxyl group is 2,3,6-trimethylphenol.

22. The radiation-sensitive composition according to claim 1, wherein the acid generator is contained in an amount of 20 to 30% by weight of the total weight of the solid component.

23. The radiation-sensitive composition according to claim 1, further comprising an acid-diffusion controller.

24. The radiation-sensitive composition according to claim 1, wherein a number of the acid-dissociating groups in the compound B and solubilizer C is 5 to 95% of a total number of the phenolic hydroxyl groups in the compound B and solubilizer C.

25. The radiation-sensitive composition according to claim 1, wherein an amount of the solubilizer C is 80% by weight or less of a total weight of the compound B and solubilizer C.

26. The radiation-sensitive composition according to claim 1, wherein a content of the solid component is 75 to 99% by weight, a content of the solvent is 1 to 25% by weight, and a content of the compound B in the solid component is 80 to 99% by weight.

27. The radiation-sensitive composition according to claim 1, wherein an amount of residual metals in the compound B is less than 1 ppm.

28. The radiation-sensitive composition according to claim 1, which is free from resins.

29. The radiation-sensitive composition according to claim 1, wherein the compound B dissolves in at least one solvent selected from the group consisting of propylene glycol monomethyl ether acetate, propylene glycol monomethyl ether, ethyl lactate, butyl acetate, methyl 3-methoxypropionate and ethyl propionate in a concentration of 5% by weight or more at 23° C.

30. The radiation-sensitive composition according to claim 1, wherein the solid component is capable of forming an amorphous film by a spin coating.

31. The radiation-sensitive composition according to claim 30, wherein a dissolving speed of the amorphous film into a 2.38% by weight aqueous solution of tetramethylammonium hydroxide is 5 Å/s or less at 23° C.

32. The radiation-sensitive composition according to claim 1, wherein the polyphenol compound A is capable of forming an amorphous film and a dissolving speed of the amorphous film into a 2.38% by weight aqueous solution of tetramethylammonium hydroxide is 10 Å/s or more at 23° C.

33. The radiation-sensitive composition according to claim 31, wherein the amorphous film has a dissolving speed of 10 Å/s or more after exposed to KrF excimer lasers, extreme ultraviolet rays, electron beams and X-rays and optionally heated at 20 to 250° C.

34. The radiation-sensitive composition according to claim 1, wherein the acid generator is triphenylsulfonium p-toluenesulfonate.

35. The radiation-sensitive composition according to claim 23, wherein the acid-diffusion controller is triphenylimidazole.

36. The radiation-sensitive composition according to claim 1, wherein an absorptivity coefficient of the solid component at a wavelength of 248 nm is 40 L/(cm g) or more.

37. The radiation-sensitive composition according to claim 1, wherein the compound B is produced by introducing an acid-dissociating group into at least one phenolic hydroxyl group of the polyphenol compound A in 1,3-dioxolane.

* * * * *